United States Patent
Liang et al.

(10) Patent No.: US 8,513,221 B2
(45) Date of Patent: Aug. 20, 2013

(54) PI3K ISOFORM SELECTIVE INHIBITORS

(75) Inventors: Congxin Liang, Palm Beach Gardens, FL (US); Zhigang Li, Shanghai (CN)

(73) Assignee: Xcovery Holding, LLC, West Palm Beach, FL (US)

( * ) Notice: Subject to any disclaimer, the term of this patent is extended or adjusted under 35 U.S.C. 154(b) by 171 days.

(21) Appl. No.: 12/999,032

(22) PCT Filed: Jul. 7, 2009

(86) PCT No.: PCT/US2009/003979
§ 371 (c)(1),
(2), (4) Date: Feb. 8, 2011

(87) PCT Pub. No.: WO2010/005558
PCT Pub. Date: Jan. 14, 2010

(65) Prior Publication Data
US 2011/0130395 A1 Jun. 2, 2011

Related U.S. Application Data

(60) Provisional application No. 61/134,163, filed on Jul. 7, 2008, provisional application No. 61/214,897, filed on Apr. 28, 2009.

(51) Int. Cl.
*C07D 413/14* (2006.01)
(52) U.S. Cl.
USPC .......................................................... 514/118
(58) Field of Classification Search
USPC .......................................................... 544/118
See application file for complete search history.

(56) References Cited

U.S. PATENT DOCUMENTS

| 4,704,381 A | 11/1987 | Schaumann et al. |
| 5,057,517 A | 10/1991 | Johnston et al. |
| 2007/0185140 A1 | 8/2007 | Bordon-Pallier et al. |

FOREIGN PATENT DOCUMENTS

| EP | 0 152 944 A2 | 8/1985 |
| FR | 2851248 | * 8/2004 |
| GB | 864 145 A | 3/1961 |
| WO | 03/022274 A2 | 3/2003 |
| WO | 03/031405 A2 | 4/2003 |
| WO | 2005/000404 A2 | 1/2005 |
| WO | 2007/115999 A1 | 10/2007 |
| WO | 2009/045174 A1 | 4/2009 |
| WO | 2009/045175 A1 | 4/2009 |
| WO | 2009/157880 A1 | 12/2009 |

OTHER PUBLICATIONS

N.A. Golubeva et al., "The Synthesis of N2,N6-Substituted Diaminopurine Ribosides", Russian Journal of Bioorganic Chemistry, 33(6), pp. 562-568 (2007).
W.K.D. Brill et al., "Catalysis of 2—and 6—Substitution Reactions of Purines on Solid Phase", Synlett 2001, No. 7, pp. 1097-1100 (2001).
H. Huang et al., "Microwave-Assisted Rapid Synthesis of 2,6,9-Substituted Purines", J. Comb. Chem., vol. 9, pp. 197-199 (2007).
S.R. Breschears et al., "Purines. VIII. The Aminolysis of Certain chlorosubstituted Purines", Journal of american Chemical Society, vol. 81, pp. 3789-3792 (1959).
M.T. Fiorini et al., "solution-Phase Synthesis of 2,6,9-Trisubstituted Purines", Tetrahedron Letters 39, pp. 1827-1830 (1998).

* cited by examiner

*Primary Examiner* — Rebecca Anderson
(74) *Attorney, Agent, or Firm* — Edwards Wildman Palmer LLP; Jeffrey D. Hsi; Stephen W. Rafferty

(57) ABSTRACT

2-Morpholin-4-yl-9H-purine and 5-Morpholin-4-yl-3H-[1,2,3]triazolo[4,5-d]pyrimidine derivatives, especially those substituted by 6-heteroaryl, are unexpected PI3 kinase isoform selective inhibitors with good drug properties and are useful in treating disorders related to abnormal PI3K activities such as cancer, immune disorders, cardiovascular disease, viral infection, inflammation, metabolism/endocrine disorders and neurological disorders.

4 Claims, No Drawings

PI3K ISOFORM SELECTIVE INHIBITORS

CROSS-REFERENCE TO RELATED APPLICATIONS

This application claims benefit of U.S. Provisional Application Ser. Nos. 61/134,163, filed Jul. 7, 2008 and 61/214,897, filed Apr. 28, 2009, the contents of which are incorporated by reference in their entirety.

TECHNICAL FIELD OF THE INVENTION

This invention relates to novel 2-Morpholin-4-yl-9H-purine and 5-Morpholin-4-yl-3H-[1,2,3]triazolo[4,5-d]pyrimidine derivatives, their salts, solvates, hydrates and polymorphs thereof. The invention also provides compositions comprising a compound of this invention and the use of such compositions in methods of treating diseases and conditions associated with kinase modulation, especially the phosphatidylinositol-3-kinases (PI3K).

BACKGROUND OF THE INVENTION

Phosphatidylinositol (hereinafter abbreviated as "PI") is one of a number of phospholipids found in cell membranes. In recent years it has become clear that PI plays an important role in intracellular signal transduction. In the late 1980s, a PI3 kinase (PI3K) was found to be an enzyme which phosphorylates the 3-position of the inositol ring of phosphatidylinositol (D. Whitman et al, 1988, Nature, 332, 664).

PI3K was originally considered to be a single enzyme, but it has now been clarified that a plurality of subtypes are present in PI3K. Each subtype has its own mechanism for regulating activity. Three major classes of PI3Ks have been identified on the basis of their in vitro substrate specificity (B. Vanhaesebroeck, 1997, Trend in Biol. Sci, 22, 267). Substrates for class I PI3Ks are PI, PI 4-phosphate (PI4P) and PI 4,5-biphosphate (PI (4,5)P2). Class I PI3Ks are further divided into two groups, class Ia and class Ib, in terms of their activation mechanism. Class Ia PI3Ks include PI3K P110α, p110β and p110δ subtypes, which transmit signals from tyrosine kinase-coupled receptors. Class Ib PI3K includes a p110γ subtype activated by a G protein-coupled receptor. PI and PI(4)P are known as substrates for class II PI3Ks. Class II PI3Ks include PI3K C2α, C2β and C2γ subtypes, which are characterized by containing C2 domains at the C terminus. The substrate for class III PI3Ks is PI only.

In the PI3K subtypes, the class Ia subtype has been most extensively investigated to date. The three subtypes of class Ia are heterodimers of a catalytic 110 kDa subunit and regulatory subunits of 85 kDa or 55 kDa. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Thus, the class Ia subtypes are considered to be associated with cell proliferation and carcinogenesis.

It has been extensively published that the morpholino derivatives shown in Formula I below are PI3K inhibitors:

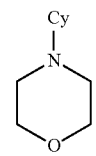

I

Wherein Cy is an unsaturated or aromatic, mono or fused ring. Some of the representative examples are listed below: LY294002 (Vlahos et al. J. Biol. Chem. 1994, 269, 5241-5248), Ia (WO2007/129161), Ib (WO2007/084786), Ic (WO2007/080382), Id (WO2007/042810), TGX221 (WO2004/016607), and Ie (WO2008/018426).

Representative morpholine based PI3K inhibitors

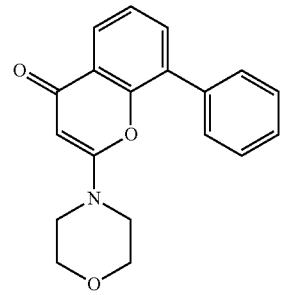

LY294002

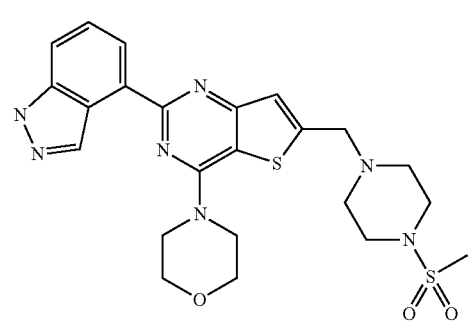

Ia

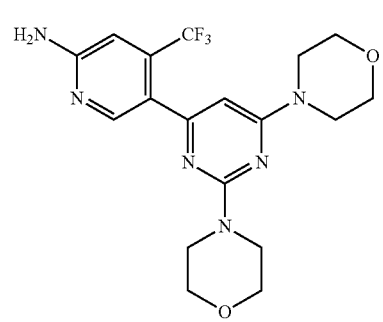

Ib

-continued

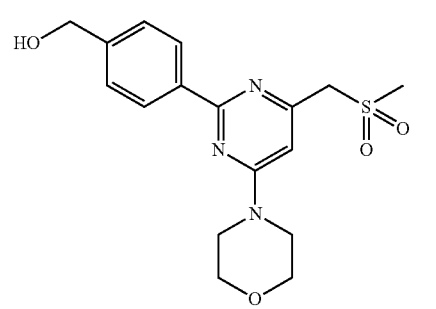

Ic

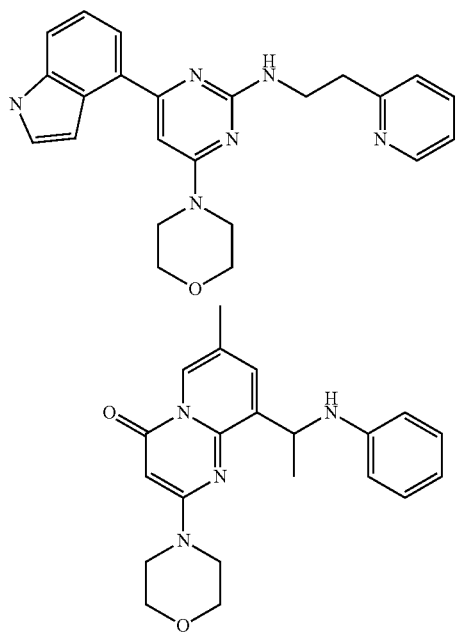

Id

TGX221

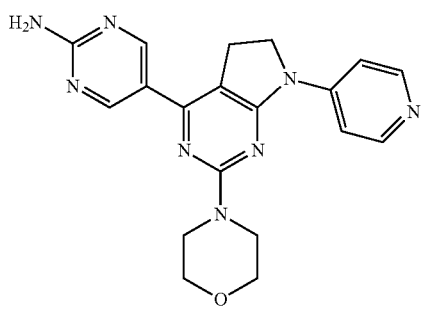

Ie

In the above examples, the morpholine group was considered essential for the PI3K inhibitory activities. In WO2007/132171, the morpholine group was replaced by a heteroaryl group.

SUMMARY OF THE INVENTION

The invention relates to 2-Morpholin-4-yl-9H-purine and 5-Morpholin-4-yl-3H-[1,2,3]triazolo[4,5-d]pyrimidine derivative compounds, compositions comprising the compounds, and methods of using the compounds and compound compositions. The compounds and compositions comprising them are useful for treating or preventing disease or disease symptoms, including those mediated by or associated with PI3K activities.

The present invention provides compounds of Formula II:

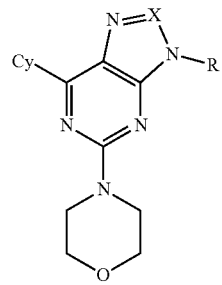

II or a salt thereof; or a prodrug, or a salt of a prodrug thereof; or a hydrate, solvate, or polymorph thereof; wherein X is N or CR'; Cy is cycloalkyl, cycloalkenyl, aryl, heteroaryl, or heterocyclo, each optionally substituted with $Z_1$, $Z_2$ and $Z_3$; R, R' are each independently hydrogen, alkyl, cycloalkyl, or heterocyclo, each optionally substituted with $Z_1$, $Z_2$ and $Z_3$;

$Z_1$, $Z_2$ and $Z_3$ are each independently:

(1) hydrogen or $Z_6$, where $Z_6$ is (i) alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl; (ii) a group (i) which is substituted by one or more groups selected from alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl; or (iii) a group (i) or (ii) which is substituted by one or more of the following groups (2) to (13);

(2) —OH or —$OZ_{16}$;

(3) —SH or —$SZ_{16}$;

(4) —$C(O)_2H$, $C(O)_qZ_{16}$, —$C(O)NZ_{17}Z_{18}$, —$C(O)C(O)NZ_{17}Z_{18}$, or —O—$C(O)_qZ_{16}$, where each q is independently 1 or 2;

(5) —$SO_3H$, —$S(O)_qZ_{16}$, or —$S(O)_qNZ_{17}Z_{18}$;

(6) halo;

(7) cyano;

(8) nitro;

(9) —$Z_4$—$NZ_{17}Z_{18}$;

(10) —$Z_4$—$N(Z_{18})$—$Z_5$—$NZ_{19}Z_{20}$;

(11) oxo;

(12) —O—C(O)—$Z_{16}$;

(13) any two of $Z_1$, $Z_2$, and $Z_3$ may together be alkylene, alkenylene, aryl, heteroaryl, or heterocyclo completing a 3- to 8-membered saturated or unsaturated ring together with the atoms to which they are attached;

$Z_4$ and $Z_5$ are each independently (1) a single bond;

(2) —$Z_{11}$—$S(O)_q$—$Z_{12}$—;

(3) —$Z_{11}$—$C(O)$—$Z_{12}$—;

(4) —$Z_{11}$—O—$Z_{12}$—;

(5) —$Z_{11}$—S—$Z_{12}$—;

(6) —$Z_{11}$—O—C(O)—$Z_{12}$—; or (7) —$Z_{11}$—C(O)—O—$Z_{12}$;

$Z_{11}$ and $Z_{12}$ are each independently (1) a single bond;

(2) alkylene;

(3) alkenylene; or (4) alkynylene;

each $Z_{16}$ is independently alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl, each optionally substituted with one or more of the following groups:
(1) hydrogen;
(2) —OH or —$OZ_{21}$;
(3) —SH or —$SZ_{21}$;
(4) —$C(O)_2H$, $C(O)_qZ_{21}$, —$C(O)NZ_{17}Z_{18}$, —$C(O)C(O)NZ_{17}Z_{18}$, or —O—$C(O)_qZ_{21}$, where each q is independently 1 or 2;
(5) —$SO_3H$, —$S(O)_qZ_{21}$, or —$S(O)_qNZ_{17}Z_{18}$;
(6) halo;
(7) cyano;
(8) nitro;
(9) —$Z_4$—$NZ_{17}Z_{18}$;
(10) —$Z_4$—$N(Z_{18})$—$Z_5$—$NZ_{19}Z_{20}$;
(11) oxo; or
(12) —O—$C(O)$—$Z_{21}$;
each $Z_{17}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;
each $Z_{18}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;
each $Z_{19}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;
each $Z_{20}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;
each $Z_{21}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;
each $Z_{22}$ is independently,
(1) hydrogen;
(2) —OH or —$OZ_{21}$;
(3) —SH or —$SZ_{21}$;
(4) —$C(O)_2H$, $C(O)_qZ_{21}$, —$C(O)NZ_{21}Z_{21}$, —$C(O)C(O)NZ_{21}Z_{21}$, or —$C(O)_qZ_{21}$, where q is 1 or 2;
(5) —$SO_3H$, —$S(O)_qZ_{21}$, or —$S(O)_qNZ_{21}Z_{21}$;
(6) halo;
(7) cyano;
(8) nitro;
(9) —$Z_4$—$NZ_{21}Z_{21}$;
(10) —$Z_4$—$N(Z_{21})$—$Z_5$—$NZ_{21}Z_{21}$;
(11) oxo; or
(12) —O—$C(O)$—$Z_{21}$;
where $Z_{17}$, $Z_{18}$, $Z_{19}$ or $Z_{20}$ may be substituted with 1, 2, or 3 independent $Z_{22}$;
where $Z_{17}$ and $Z_{18}$, or $Z_{19}$ and $Z_{20}$, together with the nitrogen atom to which they are attached may be a heterocycle which is unsubstituted or substituted with 1, 2, or 3 independent $Z_{22}$; and
where any two of $Z_{18}$, $Z_{19}$ or $Z_{20}$ together with the nitrogen atoms to which they are attached may be a 3- to 12-membered saturated or unsaturated mono-, bi-, or tri-heterocyclic ring which is unsubstituted or substituted with 1, 2, or 3 independent $Z_{22}$.

This invention also provides compounds of Formula III:

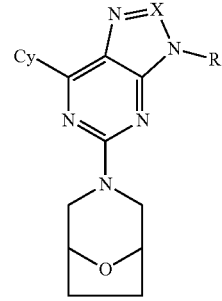

or a salt thereof; or a prodrug, or a salt of a prodrug thereof; or a hydrate, solvate, or polymorph thereof; wherein X, Cy, and R are as defined above for Formula II.

The compounds of this invention, and compositions comprising them, are useful for treating or lessening the severity of PI3K modulated diseases, disorders, or symptoms thereof.

In another aspect, the invention relates to a method of treating a disease or disease symptom in a subject in need thereof including administering to the subject an effective amount of a compound of any formulae herein, or pharmaceutical salt, solvate or hydrate thereof (or composition thereof). The disease or disease symptom can be any of those modulated by a PI3K. The disease or disease symptom can be, for example, cancer, inflammation, or cardiovascular disease or disorder.

DETAILED DESCRIPTION OF THE INVENTION

Definitions

The terms "ameliorate" and "treat" are used interchangeably and both mean decrease, suppress, attenuate, diminish, arrest, or stabilize the development or progression of a disease (e.g., a disease or disorder delineated herein).

By "disease" is meant any condition or disorder that damages or interferes with the normal function of a cell, tissue, or organ.

By "marker" is meant any alteration that is associated with a disease or disorder. For example, any protein or polynucleotide having an alteration in expression level or activity that is associated with a disease or disorder.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "compound" as used herein, is also intended to include salts, prodrugs, and prodrug salts of a compound of formulae herein. The term also includes any solvates, hydrates, and polymorphs of any of the foregoing. The specific recitation of "prodrug," "prodrug salt," "solvate," "hydrate," or "polymorph" in certain aspects of the invention described in this application shall not be interpreted as an intended omission of these forms in other aspects of the invention where the term "compound" is used without recitation of these other forms.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as amides, esters, carbamates, carbonates, and phosphate analogues. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs".

As used herein and unless otherwise indicated, the term "biohydrolyzable moiety" means a functional group (e.g., amide, ester, carbamate, carbonate, or phosphate) analogue, that either: 1) does not destroy the biological activity of the compound and confers upon that compound advantageous properties in vivo, such as uptake, duration of action, or onset of action; or 2) is itself biologically inactive but is converted in vivo to a biologically active compound.

A prodrug salt is a compound formed between an acid and a basic group of the prodrug, such as an amino functional group, or a base and an acidic group of the prodrug, such as a carboxyl functional group. In a one embodiment, the prodrug salt is a pharmaceutically acceptable salt.

Particularly favored prodrugs and prodrug salts are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. Journal of Medicinal Chemistry 1988, 31, 318-322; Bundgaard, H. Design of Prodrugs; Elsevier: Amsterdam, 1985; pp 1-92; Bundgaard, H.; Nielsen, N. M. Journal of Medicinal Chemistry 1987, 30, 451-454; Bundgaard, H. A Textbook of Drug Design and Development; Harwood Academic Publ.: Switzerland, 1991; pp 113-191; Digenis, G. A. et al. Handbook of Experimental Pharmacology 1975, 28, 86-112; Friis, G. J.; Bundgaard, H. A Textbook of Drug Design and Development; 2 ed.; Overseas Publ.: Amsterdam, 1996; pp 351-385; Pitman, I. H. Medicinal Research Reviews 1981, 1, 189-214.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups of prodrugs of this invention include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

As used herein, the term "polymorph" means solid crystalline forms of a compound or complex thereof which may be characterized by physical means such as, for instance, X-ray powder diffraction patterns or infrared spectroscopy. Different polymorphs of the same compound can exhibit different physical, chemical and/or spectroscopic properties. Different physical properties include, but are not limited to stability (e.g., to heat, light or moisture), compressibility and density (important in formulation and product manufacturing), hygroscopicity, solubility, and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X" % of other stereoisomers (wherein X is a number between 0 and 100, inclusive) are present. Methods of obtaining or synthesizing diastereomers are well known in the art and may be applied as practicable to final compounds or to starting material or intermediates. Other embodiments are those wherein the compound is an isolated compound. The term "at least X % enantiomerically enriched" as used herein means that at least X % of the compound is a single enantiomeric form, wherein X is a number between 0 and 100, inclusive.

The term "stable compounds", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"Stereoisomer" refers to both enantiomers and diastereomers.

As used herein, the term "halo" or "halogen" refers to any radical of fluorine, chlorine, bromine or iodine.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms (inclusive). The term "arylalkyl" refers to a moiety in which an alkyl hydrogen atom is replaced by an aryl group. The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkoxy" refers to an —O-alkyl radical. The term "alkylenedioxo" refers to a divalent species of the structure —O—R—O—, in which R represents an alkylene.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a divalent straight chain bridge of 1 to 5 carbon atoms connected by single bonds (e.g., —(CH$_2$)$_x$—, wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH═CH—CH═CH—, —CH$_2$—CH═CH—, —CH$_2$—CH═CH-CH$_2$—, —C(CH$_3$)$_2$CH═CH— and —CH(C$_2$H$_5$)—CH═CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —CH$_2$—C≡C—, —CH(CH$_3$)—C≡C— and —C≡C—CH(C$_2$H$_5$)CH$_2$—.

The terms "cycloalkyl" and "cycloalkenyl" as employed herein includes saturated and partially unsaturated cyclic, respectively, hydrocarbon groups having 3 to 12 carbons, preferably 3 to 8 carbons, and more preferably 3 to 6 carbon.

The terms "Ar" or "aryl" refer to aromatic cyclic groups (for example 6 membered monocyclic, 10 membered bicyclic or 14 membered tricyclic ring systems) which contain 6 to 14 carbon atoms. Exemplary aryl groups include phenyl, naphthyl, biphenyl and anthracene.

Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system, wherein 0, 1, 2, 3, or 4 atoms of each ring may be substituted by a substituent. Examples, without limitation, of heteroaryl groups are pyrrole, furan, thiophene, imidazole, oxazole, thiazole, pyrazole, pyridine, pyrimidine, quinoline, quinazoline, isoquinoline, purine and carbazole.

The terms "heterocycle", "heterocyclic" or "heterocyclo" refer to fully saturated or partially unsaturated cyclic groups, for example, 3 to 7 membered monocyclic, 7 to 12 membered bicyclic, or 10 to 15 membered tricyclic ring systems, which have at least one heteroatom in at least one ring, wherein 0, 1, 2 or 3 atoms of each ring may be substituted by a substituent. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

The term "substituents" refers to a group "substituted" on any functional group delineated herein, e.g., alkyl, alkenyl, alkynyl, cycloalkyl, cycloalkenyl, aryl, heterocyclyl, or heteroaryl group at any atom of that group. In aspects, functional group delineated herein, e.g., alkyl, alkenyl, alkynyl, cycloalkyl, cycloalkenyl, aryl, heterocyclyl, or heteroaryl, can be substituted with a substituent (e.g., those listed below). Suitable substituents include, without limitation halogen, CN, NO$_2$, OR$^{100}$, SR$^{100}$, S(O)$_2$OR$^{100}$, NR$^{100}$R$^{101}$, C$_1$-C$_2$perfluoroalkyl, C$_1$-C$_2$ perfluoroalkoxy, 1,2-methylenedioxy, C(O)OR$^{100}$, C(O)NR$^{100}$R$^{101}$, OC(O)NR$^{100}$R$^{101}$, NR$^{100}$C(O)NR$^{100}$R$^{101}$, C(NR$^{101}$)NR$^{100}$R$^{101}$, NR$^{100}$C(NR$^{101}$)NR$^{100}$R$^{101}$, S(O)$_2$NR$^{100}$R$^{101}$, R$^{102}$, C(O)R$^{102}$, NR$^{100}$C(O)R$^{102}$, S(O)R$^{102}$, S(O)$_2$R$^{102}$, R$^{101}$, oxo, C(O)R$^{101}$, C(O)(CH$_2$)nOH, (CH$_2$)nOR$^{100}$, (CH$_2$)nC(O)NR$^{100}$R$^{101}$, NR$^{100}$S(O)$_2$R$^{102}$, where n is independently 0-6 inclusive. Each R$^{100}$ is independently hydrogen, C$_1$-C$_4$ alkyl or C$_3$-C$_6$ cycloalkyl. Each R$^{101}$ is independently hydrogen, alkenyl, alkynyl, C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each R$^{102}$ is independently C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each C$_3$-C$_6$ cycloalkyl, aryl, heterocyclyl, heteroaryl and C$_1$-C$_4$ alkyl in each R$^{100}$, R$^{101}$ and R$^{102}$ can optionally be substituted with halogen, CN, C$_1$-C$_4$ alkyl, OH, C$_1$-C$_4$ alkoxy, NH$_2$, C$_1$-C$_4$ alkylamino, C$_1$-C$_4$ dialkylamino, C$_1$-C$_2$perfluoroalkyl, C$_1$-C$_2$ perfluoroalkoxy, or 1,2-methylenedioxy.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention.

The present invention provides a compound of Formula II:

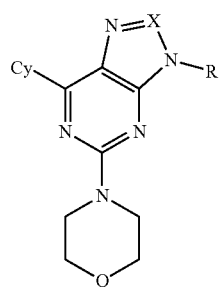

II or a salt thereof; or a prodrug, or a salt of a prodrug thereof; or a hydrate, solvate, or polymorph thereof; wherein X is N or CR'; Cy is cycloalkyl, cycloalkenyl, aryl, heteroaryl, or heterocyclo, each optionally substituted with $Z_1$, $Z_2$ and $Z_3$; R, R' are each independently hydrogen, alkyl, cycloalkyl, or heterocyclo, each optionally substituted with $Z_1$, $Z_2$ and $Z_3$;

$Z_1$, $Z_2$ and $Z_3$ are each independently:

(1) hydrogen or $Z_6$, where $Z_6$ is (i) alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl; (ii) a group (i) which is substituted by one or more groups selected from alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl; or (iii) a group (i) or (ii) which is substituted by one or more of the following groups (2) to (13);

(2) —OH or —$OZ_{16}$;
(3) —SH or —$SZ_{16}$;
(4) —$C(O)_2H$, $C(O)_qZ_{16}$, —$C(O)NZ_{17}Z_{18}$, —$C(O)C(O)NZ_{17}Z_{18}$, or —O—$C(O)_qZ_{16}$, where each q is independently 1 or 2;
(5) —$SO_3H$, —$S(O)_qZ_{16}$, or —$S(O)_qNZ_{17}Z_{18}$;
(6) halo;
(7) cyano;
(8) nitro;
(9) —$Z_4$—$NZ_{17}Z_{18}$;
(10) —$Z_4$—$N(Z_{18})$—$Z_5$—$NZ_{19}Z_{20}$;
(11) oxo;
(12) —O—$C(O)$—$Z_{16}$;
(13) any two of $Z_1$, $Z_2$, and $Z_3$ may together be alkylene, alkenylene, aryl, heteroaryl, or heterocyclo completing a 3- to 8-membered saturated or unsaturated ring together with the atoms to which they are attached;

$Z_4$ and $Z_5$ are each independently
(1) a single bond;
(2) —$Z_{11}$—$S(O)_q$—$Z_{12}$—;
(3) —$Z_{11}$—$C(O)$—$Z_{12}$—;
(4) —$Z_{11}$—O—$Z_{12}$—;
(5) —$Z_{11}$—S—$Z_{12}$—;
(6) —$Z_{11}$—O—$C(O)$—$Z_{12}$—; or
(7) —$Z_{11}$—$C(O)$—O—$Z_{12}$;

$Z_{11}$ and $Z_{12}$ are each independently
(1) a single bond;
(2) alkylene;
(3) alkenylene; or
(4) alkynylene;

each $Z_{16}$ is independently alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl, each optionally substituted with one or more of the following groups:

(1) hydrogen;
(2) —OH or —$OZ_{21}$;
(3) —SH or —$SZ_{21}$;
(4) —$C(O)_2H$, $C(O)_qZ_{21}$, —$C(O)NZ_{17}Z_{18}$, —$C(O)C(O)NZ_{17}Z_{18}$, or —O—$C(O)_qZ_{21}$, where each q is independently 1 or 2;
(5) —$SO_3H$, —$S(O)_qZ_{21}$, or —$S(O)_qNZ_{17}Z_{18}$;
(6) halo;
(7) cyano;
(8) nitro;
(9) —$Z_4$—$NZ_{17}Z_{18}$;
(10) —$Z_4$—$N(Z_{18})$—$Z_5$—$NZ_{19}Z_{20}$;
(11) oxo; or
(12) —O—$C(O)$—$Z_{21}$;

each $Z_{17}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{18}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{19}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{20}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{21}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{22}$ is independently,
(1) hydrogen;
(2) —OH or —$OZ_{21}$;
(3) —SH or —$SZ_{21}$;
(4) —$C(O)_2H$, $C(O)_qZ_{21}$, —$C(O)NZ_{21}Z_{21}$, —$C(O)C(O)NZ_{21}Z_{21}$, or —O—$C(O)_qZ_{21}$, where q is 1 or 2;
(5) —$SO_3H$, —$S(O)_qZ_{21}$, or —$S(O)_qNZ_{21}Z_{21}$;
(6) halo;
(7) cyano;
(8) nitro;
(9) —$Z_4$—$NZ_{21}Z_{21}$;
(10) —$Z_4$—$N(Z_{21})$—$Z_5$—$NZ_{21}Z_{21}$;
(11) oxo; or
(12) —O—$C(O)$—$Z_{21}$;

where $Z_{17}$, $Z_{18}$, $Z_{19}$ or $Z_{20}$ may be substituted with 1, 2, or 3 independent $Z_{22}$;

where $Z_{17}$ and $Z_{18}$, or $Z_{19}$ and $Z_{20}$, together with the nitrogen atom to which they are attached may be a heterocycle which is unsubstituted or substituted with 1, 2, or 3 independent $Z_{22}$; and where any two of $Z_{18}$, $Z_{19}$ or $Z_{20}$ together with the nitrogen atoms to which they are attached may be a 3- to 12-membered saturated or unsaturated mono-, bi-, or tri-heterocyclic ring which is unsubstituted or substituted with 1, 2, or 3 independent $Z_{22}$.

In one aspect, the compounds are of any of the formulae IIa:

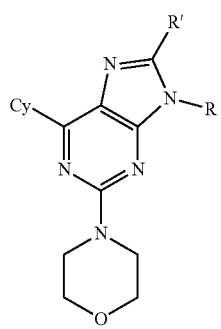

IIa wherein Cy, R, R' are as defined for formula II.

In one aspect, the compounds are of any of the formulae IIb:

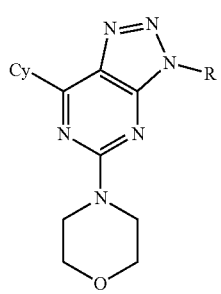

IIb wherein Cy, R are as defined for formula II.

In one aspect, the compounds are of any of the formulae IIc:

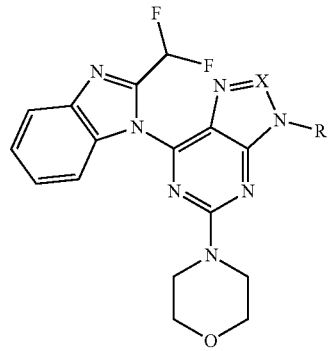

IIc wherein X and R are as defined for Formula II.

In one aspect, the compounds are of any of the formulae IId:

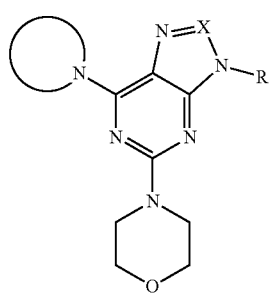

IId wherein X and R are as defined for Formula II, and

represents a mono or bicyclo heteroaryl optionally substituted with $Z_1$, $Z_2$ and $Z_3$.

This invention also provides compounds of Formula III:

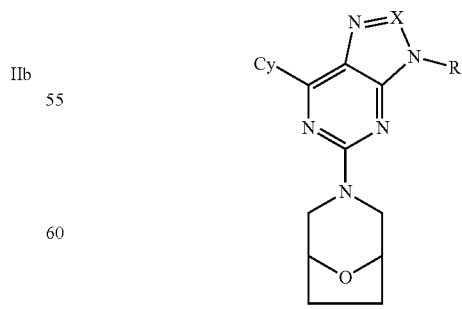

III or a salt thereof; or a prodrug, or a salt of a prodrug thereof; or a hydrate, solvate, or polymorph thereof; wherein X, Cy, and R are as defined above for Formula II.

In one aspect, the compounds are of any of the formulae IIIa:

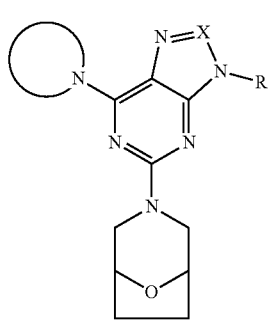

IIIa wherein X and R are as defined for Formula II, and

represents a mono or bicyclo heteroaryl optionally substituted with $Z_1$, $Z_2$ and $Z_3$.

In one aspect, the compound is a compound of Formula (II) or (III) wherein X is CH.

In one aspect, the compound is a compound of Formula (II) or (III) wherein Cy is benzoimidazol-1-yl.

In one aspect, the compound is a compound of Formula (II) or (III) wherein Cy is haloalkyl substituted benzoimidazol-1-yl.

In one aspect, the compound is a compound of Formula (II) or (III) wherein Cy is 2-difluoromethyl-benzimidazol-1-yl.

In one aspect, the compound is a compound of Formula (II) or (III) wherein R is optionally substituted alkyl.

In one aspect, the compound is a compound of Formula (II) or (III) wherein R is alkyl substituted with hydroxy, alkoxy, oxo, heterocyclyl or heteroaryl.

In one aspect, the compound is a compound of Formula (II) or (III) wherein Cy is hydroxy-substituted aryl.

In one aspect, the compound is a compound of Formula (II) or (III) wherein Cy is aryl.

In one aspect, the compound is a compound of Formula (II) or (III) wherein Cy is

optionally substituted with $Z_1$, $Z_2$ and $Z_3$.

In one aspect, the compound is a compound of Table 1.
In one aspect, the compound is a compound of Table 2.
In one aspect, the compound is a compound of Table 3.

Representative compounds of the invention are depicted in Tables 1-3. The structures in Tables 1-3 and the schemes therein contain certain —NH—, —NH$_2$ (amino) and —OH (hydroxyl) groups where the corresponding hydrogen atom(s) do not explicitly appear; however they are to be read as —NH—, —NH$_2$ or —OH as the case may be.

TABLE 1

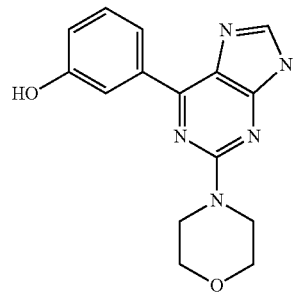 [SMILES: Oc1cccc(-c2nc(N3CCOCC3)nc3[nH]cnc23)c1]

a

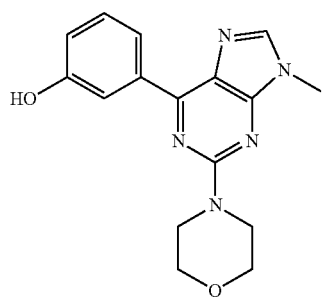 [SMILES: Cn1cnc2c(-c3cccc(O)c3)nc(N3CCOCC3)nc21]

b

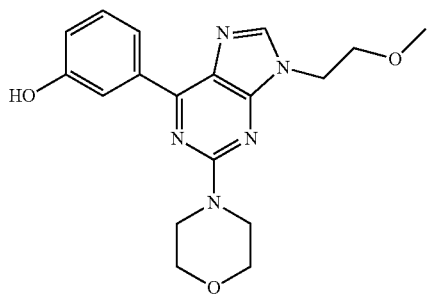 [SMILES: COCCn1cnc2c(-c3cccc(O)c3)nc(N3CCOCC3)nc21]

c

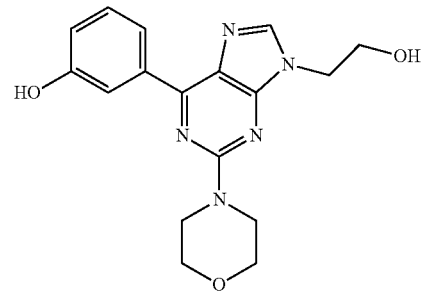 [SMILES: OCCn1cnc2c(-c3cccc(O)c3)nc(N3CCOCC3)nc21]

d

TABLE 1-continued
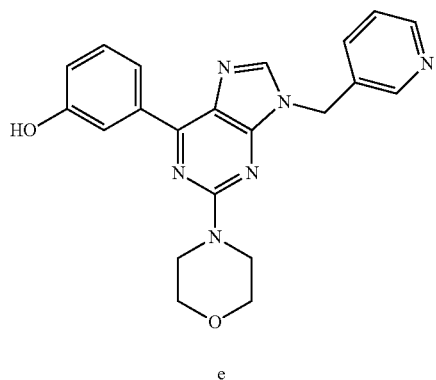
e
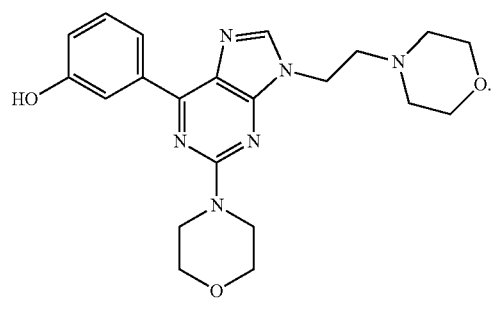 [SMILES: Oc1cccc(-c2nc(N3CCOCC3)nc3c2ncn3CCN2CCOCC2)c1]
f
TABLE 2
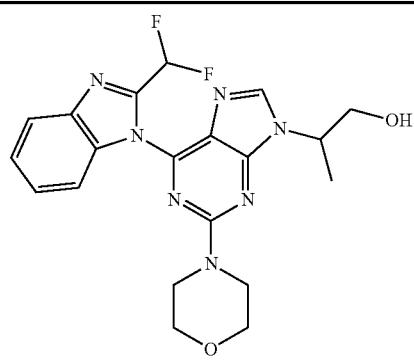
g
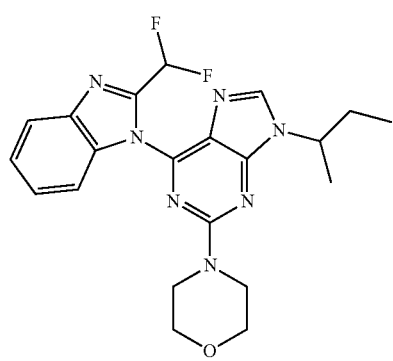 [SMILES: CCC(C)n1cnc2c(-n3c(C(F)F)nc4ccccc43)nc(N3CCOCC3)nc21]
h
TABLE 2-continued
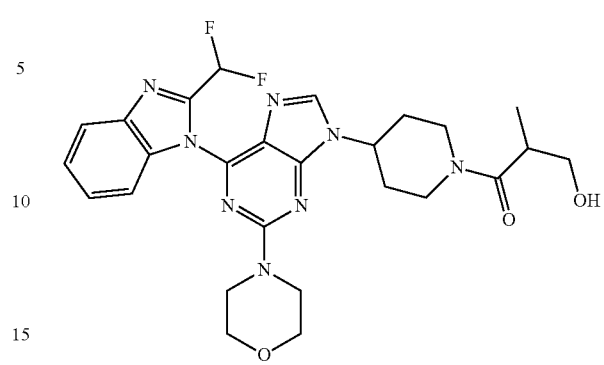
i
TABLE 3
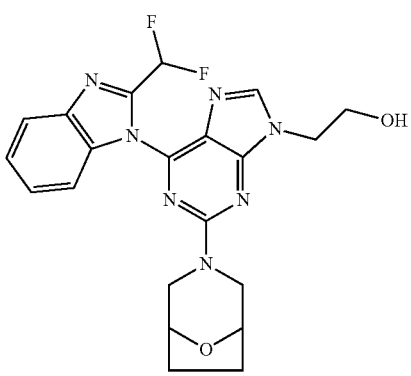
j
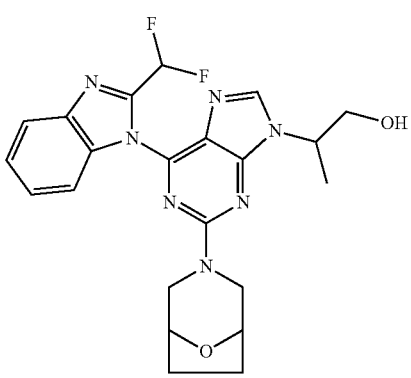
k

TABLE 3-continued

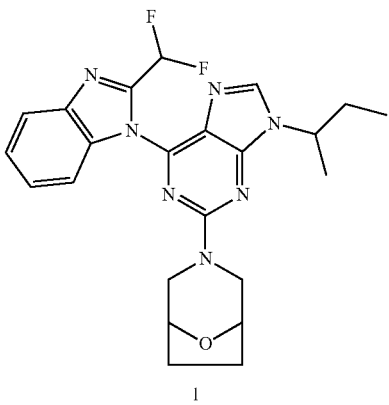 [SMILES: CCC(C)n1cnc2c(-n3c(C(F)F)nc4ccccc43)nc(N3CC4CCC(C3)O4)nc21]

l

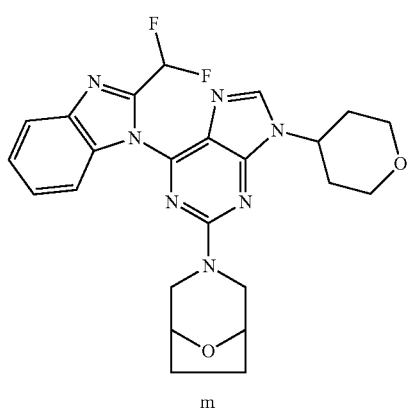 [SMILES: FC(F)c1nc2ccccc2n1-c1nc(N2CC3CCC(C2)O3)nc2c1ncn2C1CCOCC1]

m

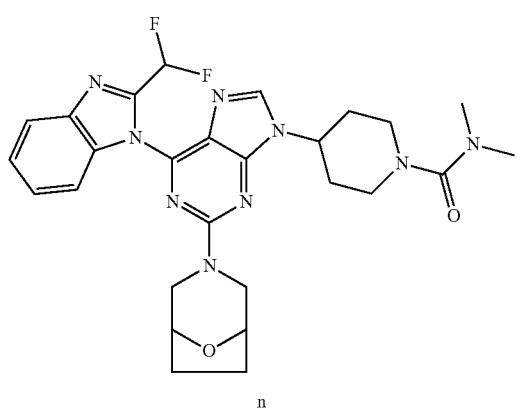 [SMILES: CN(C)C(=O)N1CCC(n2cnc3c(-n4c(C(F)F)nc5ccccc54)nc(N4CC5CCC(C4)O5)nc32)CC1]

n

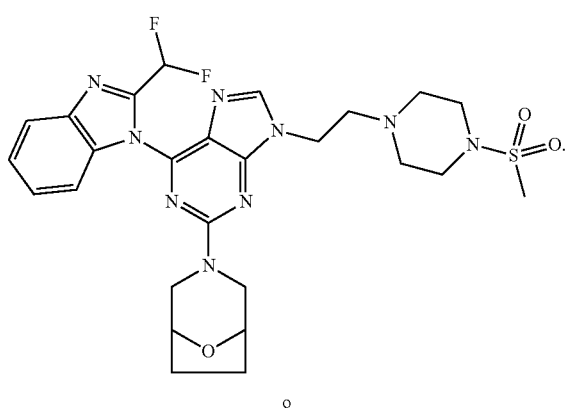 [SMILES: CS(=O)(=O)N1CCN(CCn2cnc3c(-n4c(C(F)F)nc5ccccc54)nc(N4CC5CCC(C4)O5)nc32)CC1]

o

In another aspect, the compound is one of:
6-(2-difluoromethyl-benzoimidazol-1-yl)-9-[2-(4-methane-sulfonyl-piperazin-1-yl)-ethyl]-2-morpholin-4-yl-9H-purine;
2-{6-[2-(difluoromethyl)benzimidazol-1-yl]-2-morpholin-4-ylpurin-9-yl}ethan-1-ol;
2-[6-(2-methylbenzimidazolyl)-2-morpholin-4-ylpurin-9-yl]ethan-1-ol;
6-(2-difluoromethyl-benzoimidazol-1-yl)-2-morpholin-4-yl-9-(tetrahydro-pyran-4-yl)-9H-purine;
9-sec-butyl-6-(2-difluoromethyl-benzoimidazol-1-yl)-2-morpholin-4-yl-9H-purine;
2-[6-(2-difluoromethyl-benzoimidazol-1-yl)-2-morpholin-4-yl-purin-9-yl]-propan-1-ol; or
2-[6-(2-difluoromethyl-benzoimidazol-1-yl)-2-(8-oxa-3-aza-bicyclo[3.2.1]oct-3-yl)-purin-9-yl]-propan-1-ol.

The synthesis of compounds of the formulae herein (e.g., Formula II and III) can be readily effected by synthetic chemists of ordinary skill. Relevant procedures and intermediates are disclosed, for instance, herein. Each of the patents, patent applications, and publications, whether in traditional journals or available only through the internet, referred to herein, is incorporated in its entirety by reference.

Other approaches to synthesizing compounds of the formulae herein (e.g., Formula II and III) can readily be adapted from references cited herein. Variations of these procedures and their optimization are within the skill of the ordinary practitioner.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (e.g., $R^1$, $R^2$, R, R', X, etc.) or not. The suitability of a chemical group in a compound structure for use in synthesis of another compound structure is within the knowledge of one of ordinary skill in the art. Additional methods of synthesizing compounds of the formulae herein (e.g., Formula II and III) and their synthetic precursors, including those within routes not explicitly shown in schemes herein, are within the means of chemists of ordinary skill in the art. Methods for optimizing reaction conditions, if necessary minimizing competing by-products, are known in the art. The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The synthetic methods described herein may also additionally include steps, either before or after any of the steps described in any scheme, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, sublimation, crystallization, trituration, solid phase extraction, and chromatography).

Combinations of substituents and variables envisioned by this invention are only those that result in the formation of stable compounds.

The invention also provides compositions comprising an effective amount of a compound of any of the formulae herein (e.g., Formula II and III), or a pharmaceutically acceptable salt, solvate, hydrate, polymorph or prodrug, if applicable, of said compound; and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued U.S. patents, some of which include, but are not limited to, U.S. Pat. Nos. 4,369,172; and 4,842,866, and references cited therein. Coatings can be used for delivery of compounds to the intestine (see, e.g., U.S. Pat. Nos. 6,638,534, 5,217,720, and 6,569,457, 6,461,631, 6,528,080, 6,800,663, and references cited therein). A useful formulation for the compounds of this invention is the form of enteric pellets of which the enteric layer comprises hydroxypropylmethylcellulose acetate succinate.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. A *Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. A *Textbook of Drug Design and Development;* 2 ed.; Overseas Publ.: Amsterdam, 1996; pp 351-385; Pitman, I. H. *Medicinal Research Reviews* 1981, 1, 189-214.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

In another embodiment, a composition of the present invention further comprises a second therapeutic agent. The second therapeutic agent includes any compound or therapeutic agent known to have or that demonstrates advantageous properties when administered alone or with a compound of any of the formulae herein. Drugs that could be usefully combined with these compounds include other kinase inhibitors and/or other chemotherapeutic agents for the treatment of the diseases and disorders discussed above.

Such agents are described in detail in the art. Preferably, the second therapeutic agent is an agent useful in the treatment or prevention of a disease or condition selected from cancer.

Even more preferably the second therapeutic agent co-formulated with a compound of this invention is an agent useful in the treatment of PI3K-mediated disease/disorders such as cancer, immune disorders, cardiovascular disease, viral infection, inflammation, metabolism/endocrine disorders and neurological disorders.

In another embodiment, the invention provides separate dosage forms of a compound of this invention and a second therapeutic agent that are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. An effective amount of a compound of this invention can range from about 0.001 mg/kg to about 500 mg/kg, more preferably 0.01 mg/kg to about 50 mg/kg, more preferably 0.1 mg/kg to about 2.5 mg/kg. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents referenced above will act synergistically with the compounds of this invention. When this occurs, its will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a subject suffering from or susceptible to a disease or disorder or symptom thereof (e.g., those delineated herein) comprising the step of administering to said subject an effective amount of a compound or a composition of this invention. Such diseases are well known in the art and are also disclosed herein.

In one aspect, the method of treating involves treatment of a disorder that is mediated by one or many of the PI3K (e.g., the disease is mediated by PI-310). In a preferred embodiment, the method of this invention is used to treat a subject suffering from or susceptible to a disease or condition such as discussed by Drees et al in Expert Opin. Ther. Patents (2004) 14(5):703-732. These include cancer, immune disorders, cardiovascular disease, viral infection, inflammation, metabolism/endocrine disorders and neurological disorders. Examples of metabolism/endocrine disorders include diabetes and obesity.

Examples of cancers which the present compounds can be used to treat include leukemia, brain tumors, renal cancer, gastric cancer and cancer of the skin, bladder, breast, uterus, lung, colon, prostate, ovary and pancreas. A human or animal patient suffering from an immune disorder, cancer, cardiovascular disease, viral infection, inflammation, a metabolism/endocrine disorder or a neurological disorders may thus be treated by a method comprising the administration thereto of a compound of the present invention as defined above. The condition of the patient may thereby be improved or ameliorated.

Diseases and conditions treatable according to the methods of this invention include, but are not limited to, cancer, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colonrectum, large intestine, rectum, brain and central nervous system, Hodgkin's and leukemia.

Cardiovascular diseases which can be treated according to the methods of this invention include, but are not limited to, restenosis, cardiomegaly, atherosclerosis, myocardial infarction, and congestive heart failure.

Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Inflammatory diseases which can be treated according to the methods of this invention include, but are not limited to, rheumatoid arthritis, psoriasis, contact dermatitis, and delayed hypersensitivity reactions.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In another embodiment, the invention provides a method of modulating the activity of a PI3K in a cell comprising contacting a cell with one or more compounds of any of the formulae herein.

In another embodiment, the above method of treatment comprises the further step of co-administering to said patient one or more second therapeutic agents. The choice of second therapeutic agent may be made from any second therapeutic agent known to be useful for indications herein.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention comprising both a compound of the invention and a second therapeutic agent to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of any of the formulae herein (e.g., Formula II and III) alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of the formulae herein for use in the treatment or prevention in a subject of a disease, disorder or symptom thereof delineated herein.

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radio-labelling/assay techniques, blotting/chemiluminescence methods, real-time PCR, and the like.

The present invention also provides kits for use to treat diseases, disorders, or symptoms thereof, including those delineated herein. These kits comprise: a) a pharmaceutical composition comprising a compound of any of the formula herein (e.g., Formula II) or a salt thereof; or a prodrug, or a salt of a prodrug thereof; or a hydrate, solvate, or polymorph thereof, wherein said pharmaceutical composition is in a container; and b) instructions describing a method of using the pharmaceutical composition to treat the disease, disorder, or symptoms thereof, including those delineated herein.

The container may be any vessel or other sealed or sealable apparatus that can hold said pharmaceutical composition. Examples include bottles, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. Preferably, the container is a blister pack.

The kit may additionally comprising information and/or instructions for the physician, pharmacist or subject. Such memory aids include numbers printed on each chamber or division containing a dosage that corresponds with the days of the regimen which the tablets or capsules so specified should be ingested, or days of the week printed on each chamber or division, or a card which contains the same type of information.

All references cited herein, whether in print, electronic, computer readable storage media or other form, are expressly incorporated by reference in their entirety, including but not limited to, abstracts, articles, journals, publications, texts,

EXAMPLES

Synthesis of 1-(2-morpholin-4-ylpurin-6-yl)-3-(phenylmethoxy)benzene (A)

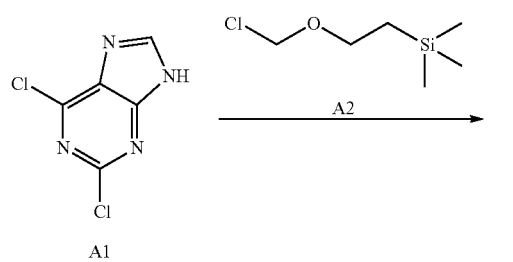

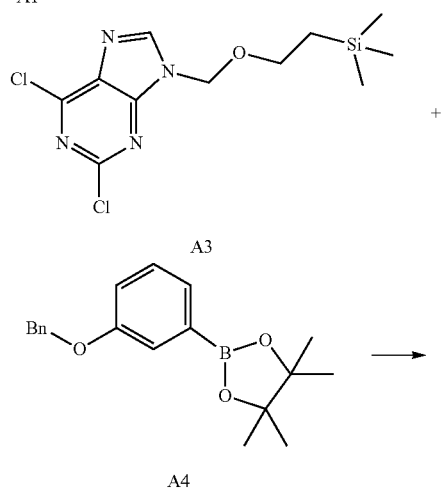

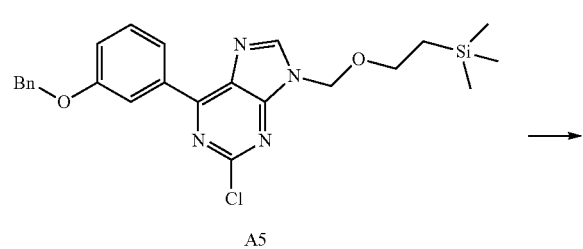

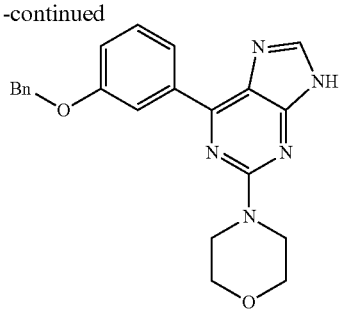

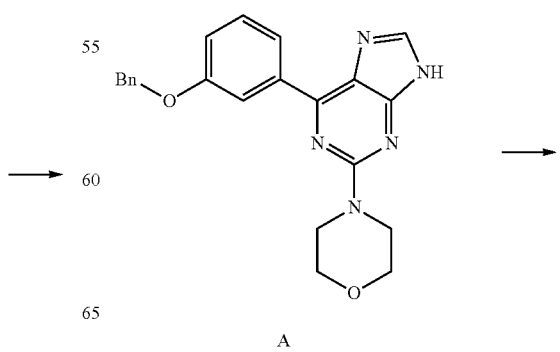

Step 1: To a solution of A1 (756 mg, 4.0 mmol) in DMF (20 mL) was added NaH (160 mg, 24.0 mmol) with ice-bath. The resulting mixture was stirred for 15 min. at 0-5° C. and was added A2 (800 mg, 4.8 mmol). The reaction mixture was stirred at r.t. for 2 h and evaporated to remove DMF. The residue was purified by column chromatography (PE:EA=8:1) to give A3 (934 mg, 73% yield).

Step 2: To a solution of A3 (934 mg, 2.92 mmol) and A4 (905 mg, 2.92 mmol) in DMF (20 mL) was added $K_2CO_3$ (1.21 g, 8.76 mmol) and $Pd(Ph_3P)_4$ (169 mg, 0.146 mmol). The mixture was degassed for three times with N2, and then heated at 100° C. overnight. The solvents were evaporated and the residue was purified by column chromatography (PE:EA=16:1) to give AS (604 mg, 44% yield).

Step 3: A solution of AS in morpholine (10 mL) was heated at 80° C. for 1 h and evaporated under vacuum to provide crude A6 which was used for next step without further purification.

Step 4: A mixture of A6 obtained above and 6N HCl (8 mL) in ethanol (20 mL) was heated to reflux for 6 h, then evaporated. The residue was suspended in 20 mL of EA, washed with water, dried over anhydrous $MgSO_4$ and concentrated. The crude was purified by column chromatography (PE:EA=1:2, 10% methanol) to provide crude A (534, ca. 100%).

Example 1

3-(2-morpholin-4-ylpurin-6-yl)phenol (1)

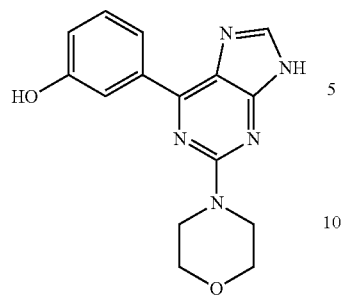

1

Step 1: To a solution of compound A (45 mg, 0.116 mmol) in methanol (10 mL) and THF (10 mL) was added 50 mg of 10% Pd/C. The mixture was degassed for three times with $N_2$, and hydrogenated under $H_2$ atmosphere over night. After removing Pd/C by filtration, the reaction was evaporated and the residue purified by prep-TLC (PE:EA=1:2) to give 1 (26 mg, 75%). 1H-NMR (300 MHz, DMSO-$d_6$): δ=3.73-3.76 (m, 8H), 6.89-6.92 (m, 1H), 7.30-7.35 (m, 1H), 8.19 (s, 1H), 8.23 (m, 2H), 9.59 (s, 1H). LC-MS [M+H]$^+$: 298.0.

Example 2

3-[9-(2-hydroxyethyl)-2-morpholin-4-ylpurin-6-yl]phenol (2)

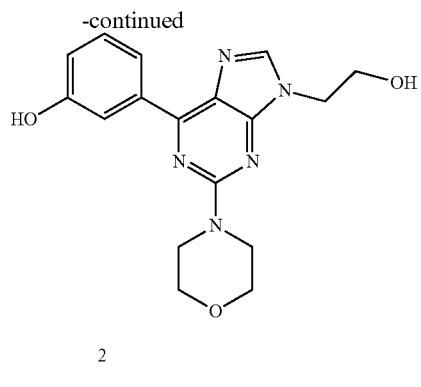

2

Step 1: A mixture of A (50 mg, 0.129 mmol), 2-bromoethan-1-ol (32 mg, 0.258 mmol), $K_2CO_3$ (53 mg, 0.387 mmol) and KI (24 mg, 0.142 mmol) in $CH_3CN$ (5 mL) was heated under microwave condition at 120° C. for 5 h. The solid was filtered off and the filtrate was evaporated under vacuum. The residue was purified by prep-TLC (PE:EA=1:1) to give 2a (42 mg, 76%).

Step 2: The procedure from 2a to 2 was similar to that of A to 1, to provide 2 (28 mg, 84%). 1H-NMR (300 MHz, DMSO-$d_6$): δ=3.13-3.81 (m, 10H), 4.17-4.20 (t, 2H), 4.99-5.02 (t, 1H), 6.89-6.93 (m, 1H), 7.30-7.36 (t, 1H), 8.19 (s, 1H), 8.22-8.27 (m, 2H), 9.62 (s, 1H). LC-MS [M+H]$^+$: 342.0.

Example 3

3-(9-methyl-2-morpholin-4-ylpurin-6-yl)phenol (3)

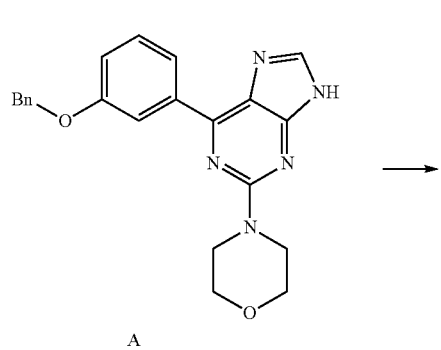

A

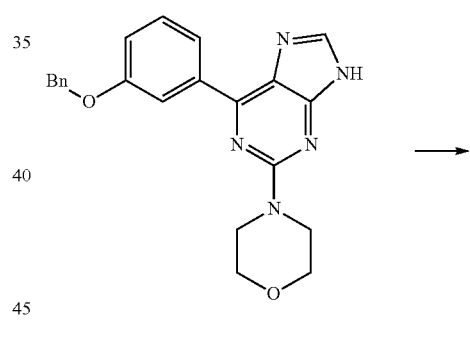

A

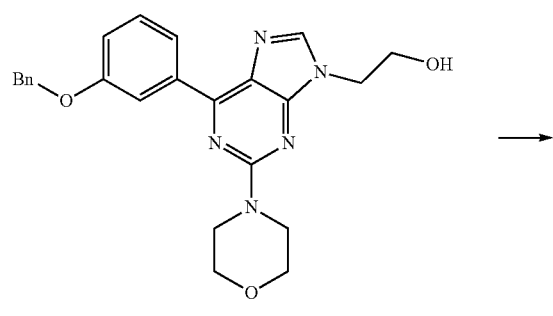

2a

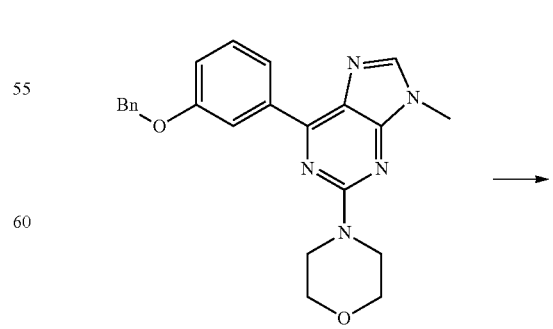

3a

-continued

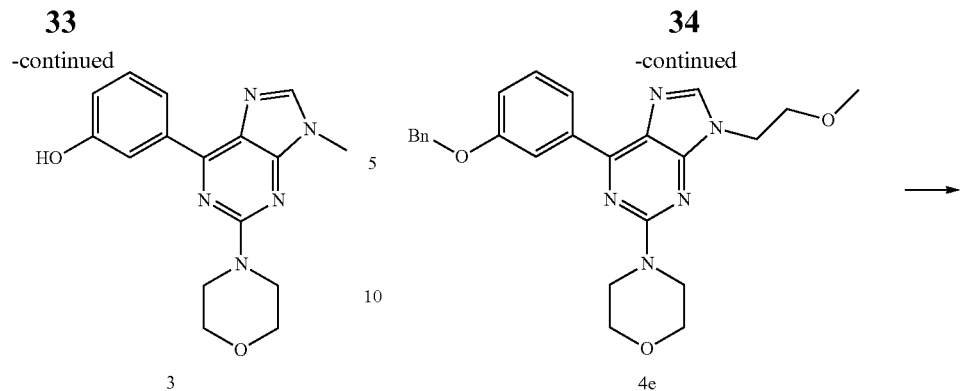

Step 1: The procedure from A to 3a was similar to that of A to 2a, to provide 3a (16.2 mg, 31.3%).

Step 2: The procedure from 3a to 3 was similar to that of A to 1 to provide obtained 3 (4.9 mg, 39.4%). 1H-NMR (300 MHz, DMSO-d$_6$): δ=3.31 (s, 3H), 3.73-3.75 (m, 4H), 3.81-3.84 (m, 4H), 6.89-6.93 (m, 1H), 7.30-7.36 (t, 1H), 8.20 (s,1H), 8.23-8.27 (m, 2H), 9.58 (s, 1H). LC-MS [M+H]$^+$: 312.0.

Example 4

3-[9-(2-methoxyethyl)-2-morpholin-4-ylpurin-6-yl]phenol

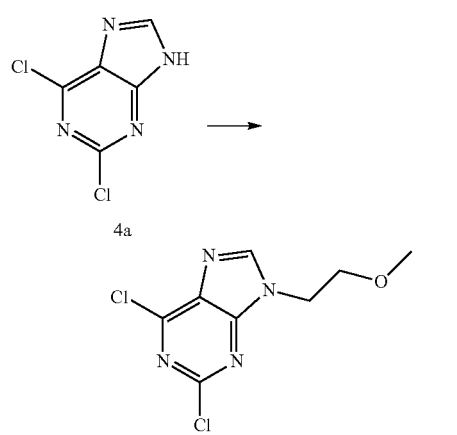

Step 1: The procedure from 4a to 4b was similar to that of A to 2a, to provide 4b (134 mg, 20.5%).

Step 2: The procedure from 4b to 4e was similar to that of A3 to A6. The crude 4e was used for next step directly without further purification.

Step 4: The procedure from 4e to 4 was similar to that of A to 1, to provide 4 (5.5 mg, 57% from 4d). 1H-NMR (300 MHz, CDCl$_3$): δ=3.35 (s, 3H), 3.70-3.74 (t, 2H), 3.81-3.84 (m, 4H), 3.91-3.94 (m, 4H), 4.28-4.32 (t, 2H), 6.94-6.98 (m, 1H), 7.35-7.40 (t, 1H), 7.92 (s, 1H), 8.19-8.24 (m, 2H). LC-MS [M+H]$^+$: 356.0.

Example 5

3-[2-morpholin-4-yl-9-(2-morpholin-4-ylethyl)purin-6-yl]phenol

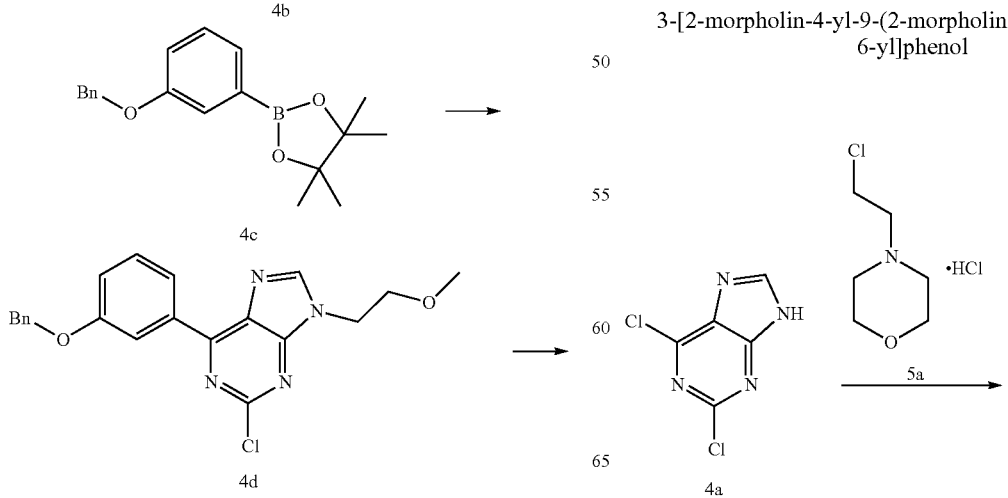

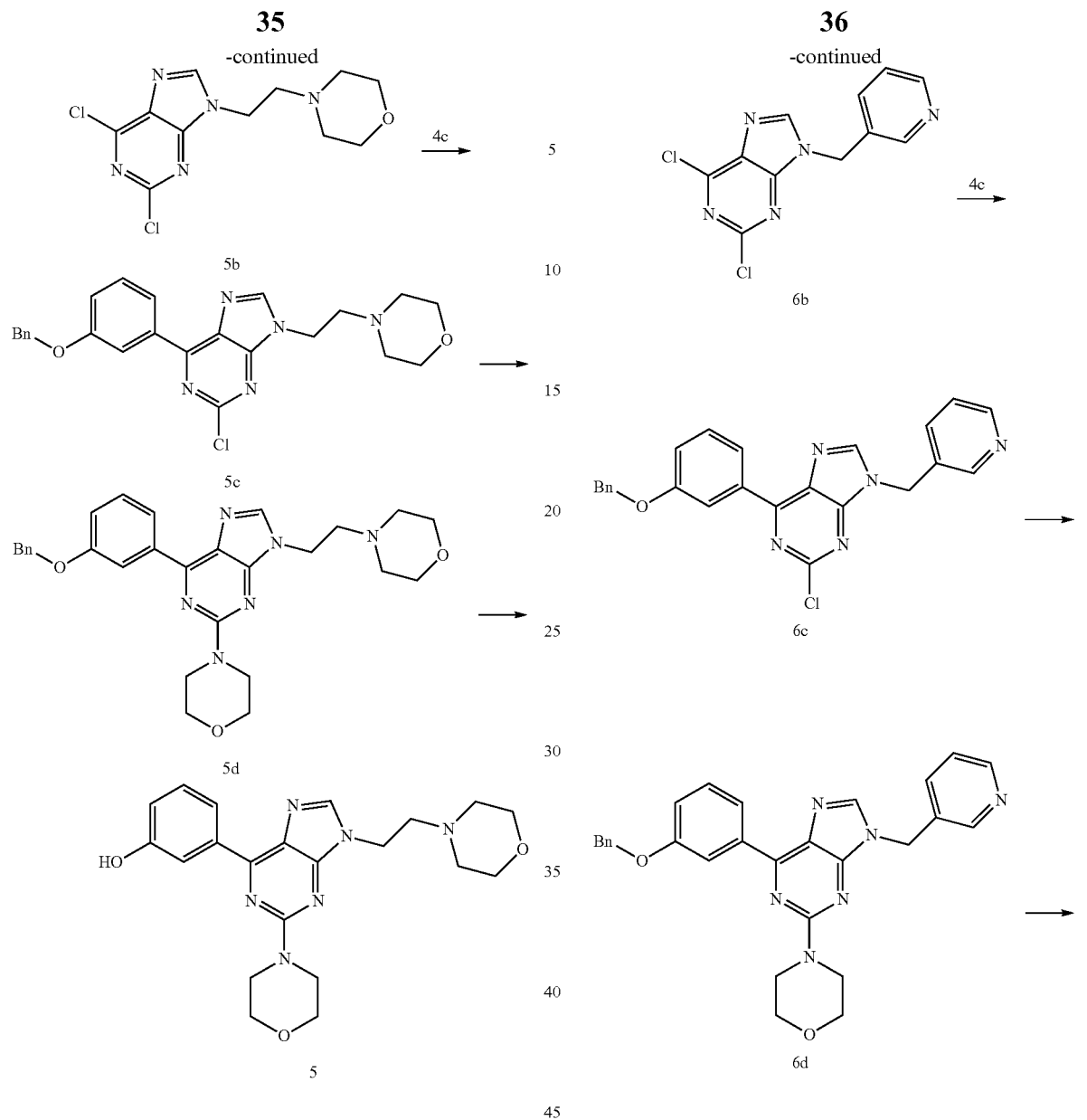
The procedure from 4a to 5 was similar to that of 4a to 4 (6.5% yield from 4a). 1H-NMR (300 MHz, CDCl₃): δ=2.51-2.55 (m, 4H), 2.77-2.81 (t, 2H), 3.61-3.71 (m, 4H), 3.82-3.85 (m, 4H), 3.90-3.93 (m, 4H), 4.22-4.26 (t, 2H), 5.82 (brs, 1H), 6.95-6.99 (m, 1H), 7.36-7.41 (t,1H), 7.94 (s, 1H), 8.23-8.30 (m, 2H). LC-MS [M+H]⁺: 411.1.
Example 6
3-[2-morpholin-4-yl-9-(3-pyridylmethyl)purin-6-yl]phenol
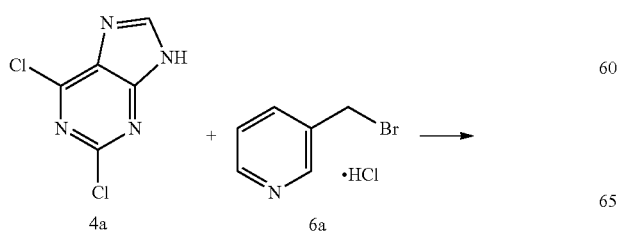
The procedure from 4a to 6 was similar to that of 4a to 4, to provide 6 (2.1% yield from 4a). 1H-NMR (300 MHz, DMSO): δ=3.71-3.82 (m, 8H), 5.41 (s, 2H), 6.87-6.93 (m, 1H), 7.30-7.40 (m, 2H), 7.80-7.83 (m, 1H), 8.20-8.25 (m, 2H), 8.41 (s, 1H), 8.50-8.52 (m, 1H), 8.70-8.71(m, 1H), 9.59 (s, 1H). LC-MS [M+H]⁺: 389.0.

Example 7

{5-[9-(2-hydroxyethyl)-2-morpholinb-4-ylpurin-6-yl](2-pyridyl)}-N-methylcarboxamide

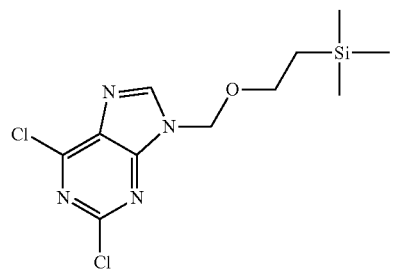

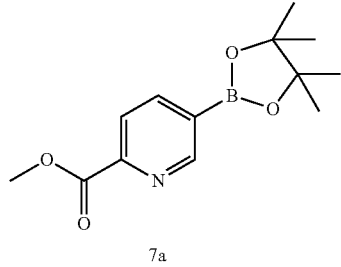

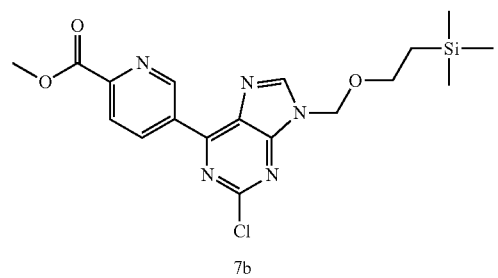

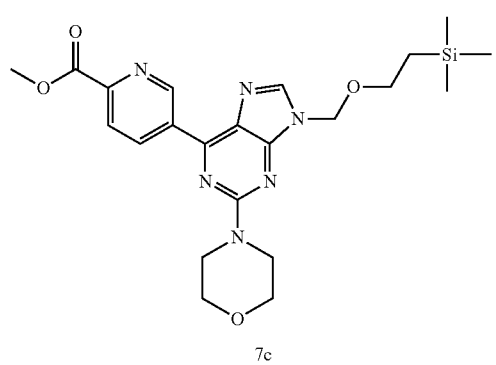

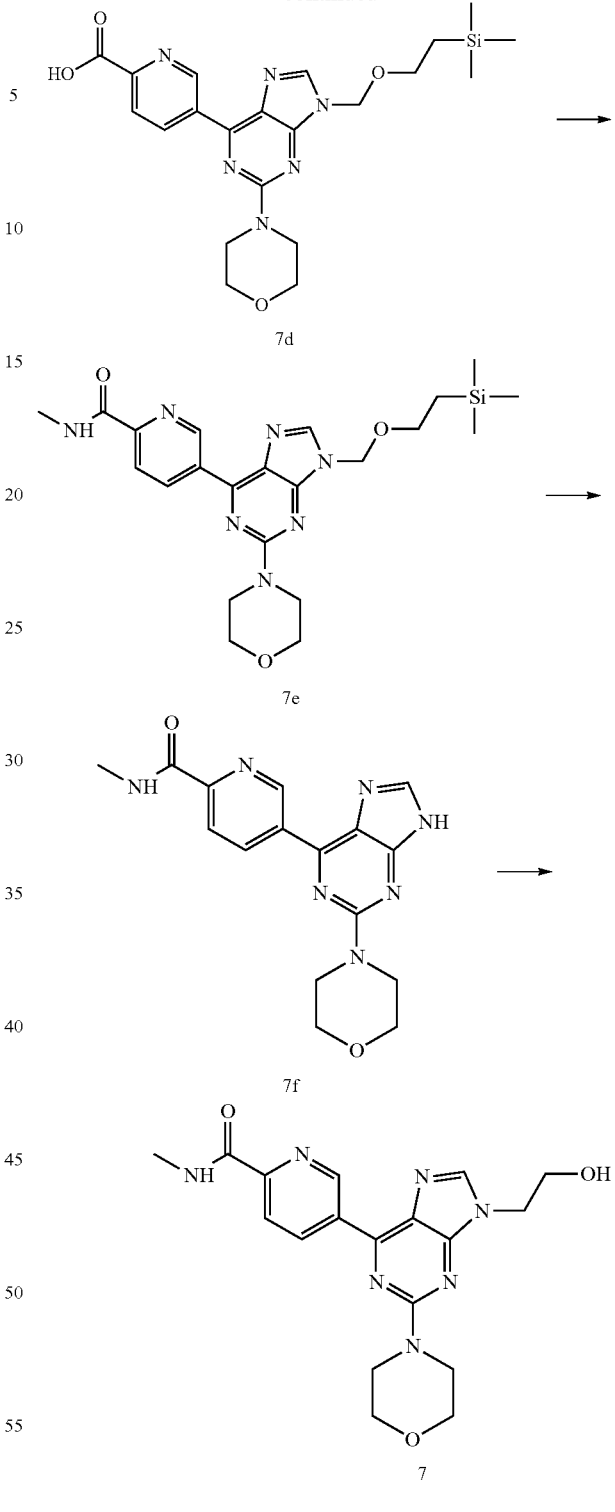

Step 1: The procedure from A3 to 7c was similar to that of A3 to A6 which provided 7c (114 mg, overall yield 16%).

Step 2: To a solution of 7c (114 mg) in THF (10 mL) was added a solution of LiOH (41 mg, 0.97 mmol) in water (5 mL). The mixture was stirred at r.t. for 5 hours, then acidified with 2N HCl to pH=4. The aqueous phase was extracted DCM. The combined extract was dried over anhydrous Na₂SO₄ and evaporated to give crude 7d (122 mg) which was used directly for next step without purification.

Step 3: A mixture of crude 7d (122 mg), HATU (152 mg, 0.40 mmol) and DIEA (103 mg, 0.80 mmol) in DMF (10 mL) was stirred at room temperature for 0.5 h, then was added methylamine hydrochloride (27 mg, 0.40 mmol). The resulting mixture was stirred at room temperature for 2 h and evaporated. The residue was purified by column chromatography (EA:PE=1:1) to provide 7e (100 mg, 14% from A3).

Step 4: The procedure from 7e to 7f was similar to that of A6 to A which provide crude 7f (87 mg, ca. 100%) which was used directly for next step without purification.

Step 5: The procedure from 7f to 7 was similar to that of A to 2a which provide 7 (19.2 mg, 19.6% from 7f). 1H-NMR (300 MHz, DMSO-$d_6$): δ=2.86 (d, 3H), 3.72-3.85 (m, 10H), 4.21 (t, 2H), 5.00 (t, 1H), 8.20 (d, 1H), 8.29 (s, 1H), 8.84-8.86 (m, 1H), 9.15-9.18 (m, 1H), 9.93-9.94 (m, 1H). LC-MS [M+H]$^+$: 384.5.

Example 8

2-{2-morpholin-4-yl-6-[1-benzylpyrrolo[2,3-b]pyridine-5-yl]purin-9-yl}ethan-1-ol

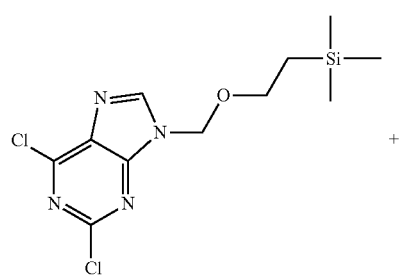

A3

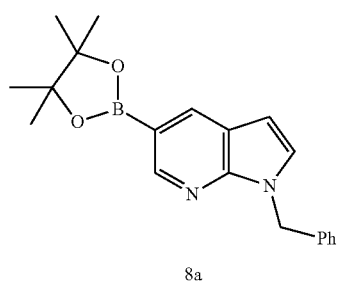

8a

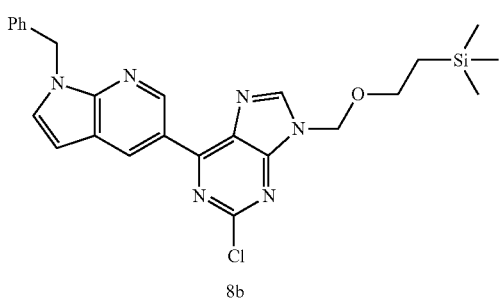

8b

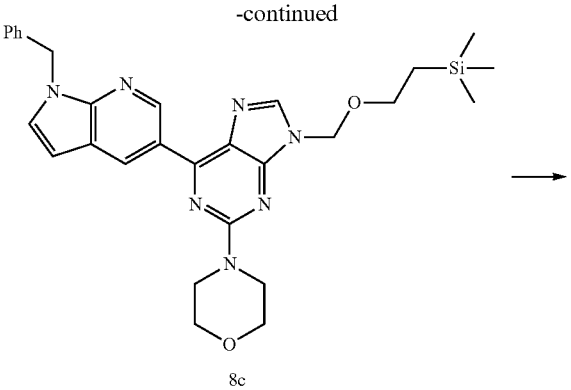

8c

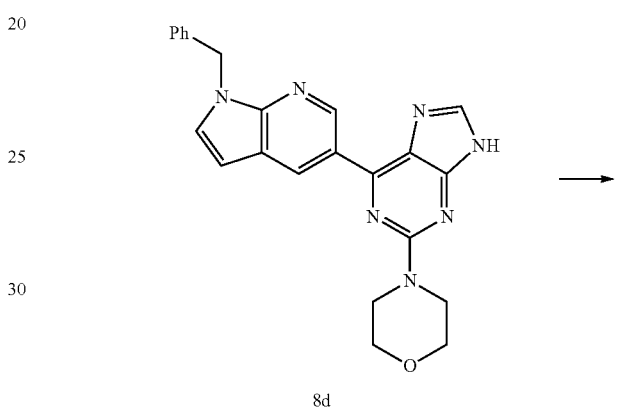

8d

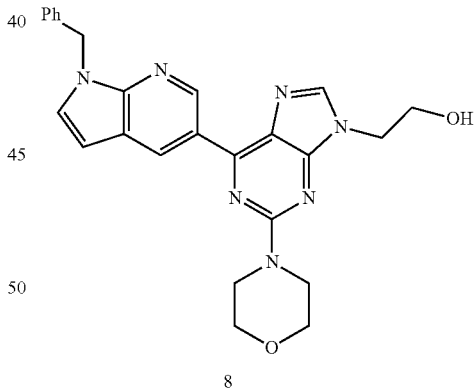

8

Step 1: The procedure from A3 to 8d was similar to that of A3 to A which provided 8d (102 mg, 28.3%).

Step 2: The procedure from 8d to 8 was similar to that of A to 2a which provided 8 (35 mg, 63.6%). 1H-NMR (300 MHz, CDCl$_3$): δ=3.83-3.92 (m, 8H), 4.05 (t, 2H), 4.32 (t, 2H), 5.55

(s, 2H), 6.62 (d, 1H), 7.22-7.31 (m, 5H), 7.81 (s, 1H), 9.39 (d, 1H), 9.68 (d, 1H). LC-MS [M+H]⁺: 456.1.

Example 9

2-[6-(3-hydroxyphenyl)-2-morpholin-4-ylpurin-9-yl]-N-methyl acetamide

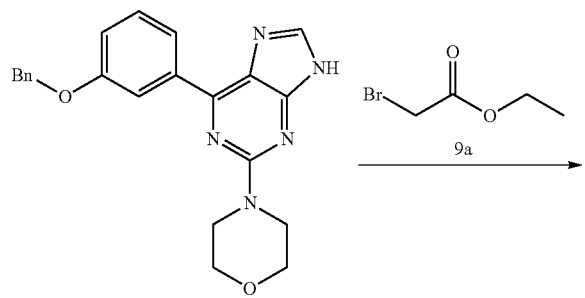

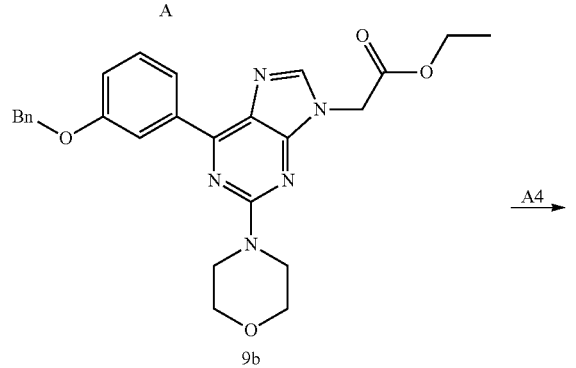

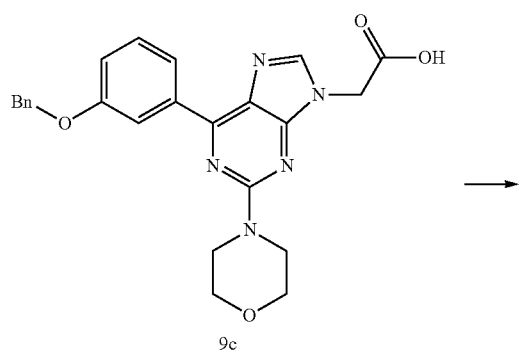

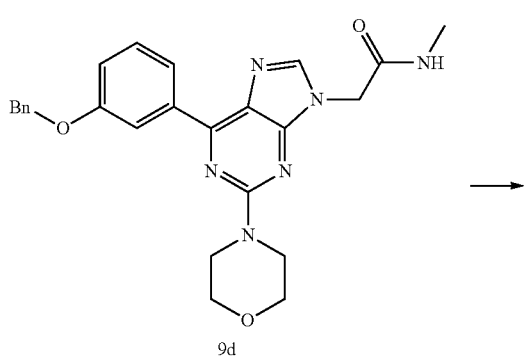

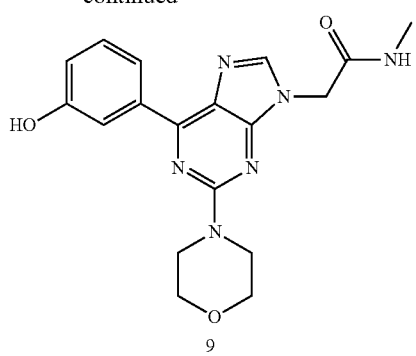

Step 1: The procedure from A to 9b was similar to that of A1 to A3 which provided crude 9b which was used directly for next step without purification.

Step 2: The procedure from 9b to 9d was similar to that of 7c to 7e which provided 9d (44 mg, 61.3% from A).

Step 3: The procedure from 9d to 9 was similar to that of A to 1 which provided 9 (14 mg, 40%). 1H-NMR (300 MHz, DMSO-d₆): δ=2.64 (d, 3H), 3.72-3.80 (m, 8H), 4.80 (s, 2H), 6.90-6.93 (m, 1H), 7.33 (t, 1H), 8.18-8.26 (m, 4H), 9.60 (s, 1H). LC-MS [M+H]⁺: 369.0.

Example 10

1-{2-[6-(3-hydroxyphenyl)-2-morpholin-4-ylpurin-9-yl]ethyl}-4-(methylsulfonyl)piperazine

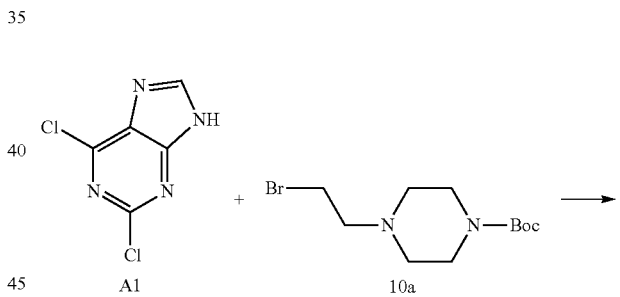

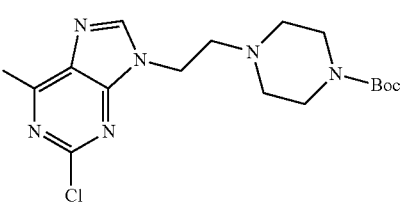

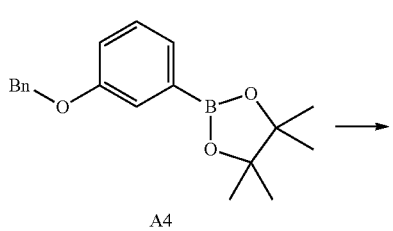

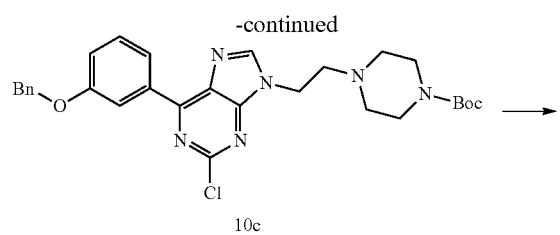

10c

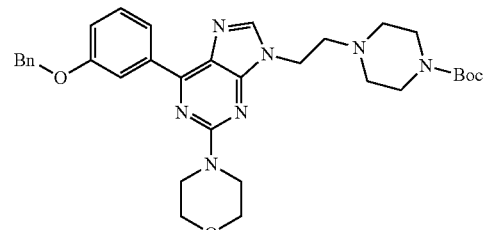

10d

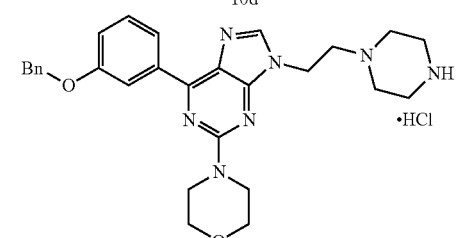

10e

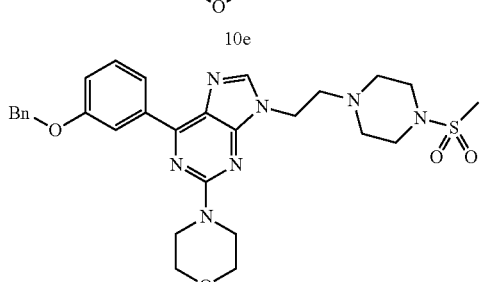

10f

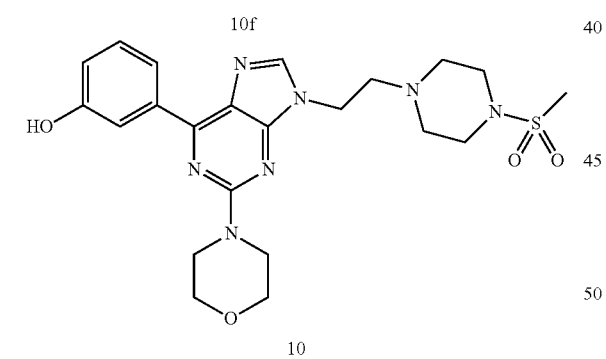

10

Step 1: The procedure from A to 10b was similar to that of A1 to A3 which provided 10b (1.74 g, 67.4%).

Step 2: The procedure from 10b to 10d was similar to that of A3 to A6 which provided 10d (1.09 g, 37% from 10b).

Step 3: To a suspension of 10d (498 mg, 0.83 mmol) in methanol (2 mL) was added a solution of HCl/Et$_2$O (2.5N, 10 mL). The mixture was stirred at r.t. overnight, then evaporated to provide 10e (561 mg).

Step 4: To a mixture of 10e (561 mg, 0.83 mmol) and Et$_3$N (504 mg, 4.99 mmol) in DCM (20 mL) was added MsCl (114 mg, 1.00 mmol) under ice-bath. The mixture was stirred at r.t. for 2 hours, and then evaporated. The residue was triturated with methanol and filtered to provide 10f (540 mg).

Step 5: The procedure from 10f to 10 was similar to that of A to 1, to provide 10 (237 mg, overall 58.7% from 10d). 1H-NMR (300 MHz, CDCl$_3$): δ=2.63-2.66 (m, 4H), 2.75 (s, 3H), 2.85 (t, 2H), 3.17-3.21 (m, 4H), 3.82-3.93 (m, 8H), 4.25 (t, 2H), 5.12(s, 1H), 6.99-7.00 (m, 1H), 7.40 (t, 1H), 7.88 (s, 1H), 8.22-8.23 (m, 1H), 8.33 (d, 1H). LC-MS [M+H]$^+$: 488.1.

Example 11

5-[2-morpholin-4-yl-9-(2-piperazinylethyl)purin-6-yl]pyrimidine-2-ylamine

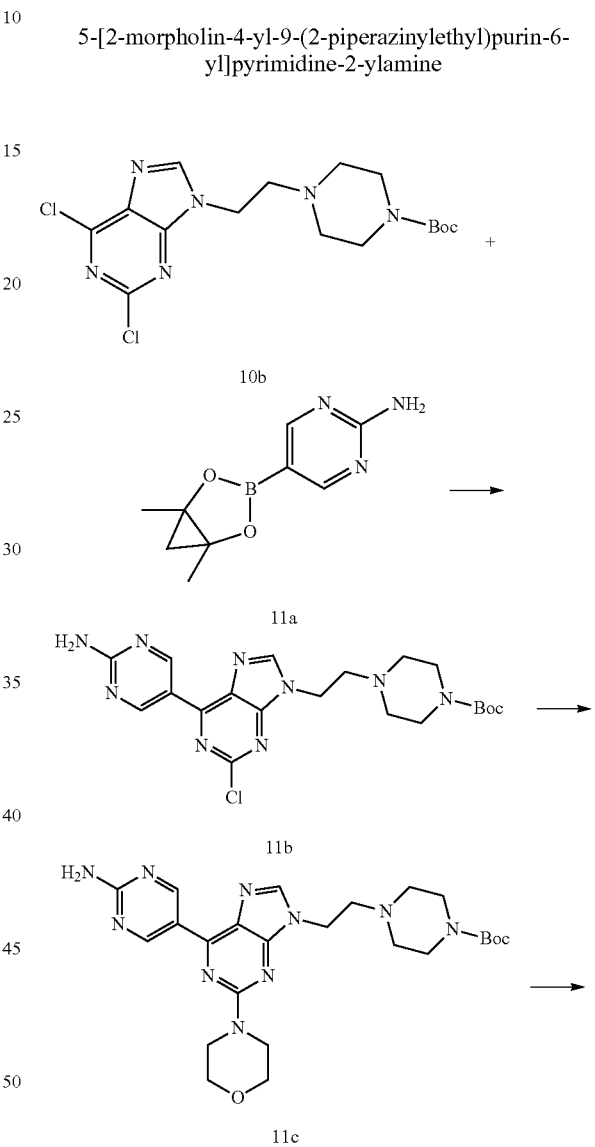

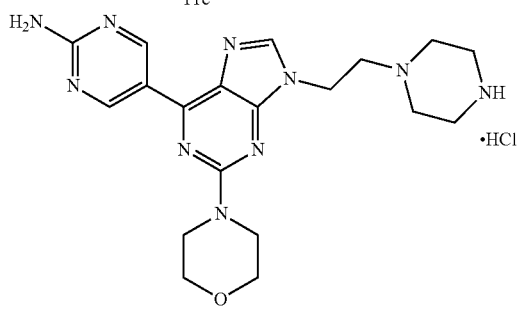

11

Step 1: To a solution of 10b (401 mg, 1.00 mmol) and 11a (221 mg, 1.00 mmol) in a mixed solvent containing toluene (4.5 mL), ethanol (3 mL) and water (1.5 mL) was added Na$_2$CO$_3$ (318 mg, 3.00 mmol) and Pd(Ph$_3$P)$_2$Cl$_2$·CH$_2$Cl$_2$ (35 mg, 0.05 mmol). The mixture was degassed three times with N$_2$, then heated at 120° C. under microwave irradiation for one hour. The solvent was evaporated and the residue was purified by column chromatography (EA: methanol=20:1) to give 11b (186 mg, 40.5% yield).

Step 2: The procedure from 11b to 11 was similar to that of 10c to 10e which provided 11 (151 mg, 77.2% from 11b). 1H-NMR (300 MHz, DMSO-d$_6$): δ=3.43-3.82 (m, 19H), 4.60 (t, 2H), 8.37 (s, 1H), 9.59(s, 2H), 9.85 (brs, 2H). LC-MS [M+H]$^+$: 411.2.

Example 12

1-{2-[6-(2-aminopyrimidin-5-yl)-2-morpholin-4-ylpurin-9-yl]ethyl}-4-(methylsulfonyl)piperazine The procedure from 11 to 12 was similar to that of 10e to 10f which provided 12 (31 mg, 40%). 1H-NMR (300 MHz, DMSO-d$_6$): δ=2.51-2.58 (m, 4H), 2.76-2.80 (m, 2H), 2.84 (s, 3H), 3.04 (t, 4H), 3.71-3.78 (m, 8H), 4.25 (t, 2H), 7.28 (s, 2H), 8.21 (s, 1H), 9.52 (s, 2H). LC-MS [M+H]$^+$: 489.1.

Example 13

(4-{2-[6-(2-aminopyrimidin-5-yl)-2-morpholin-4-ylpurin-9-yl]ethyl}piperazinyl)-N,N-dimethylcarboxamide To a suspension of 11 (55 mg, 0.12 mmol) in DMF (10 mL) was added TEA (80 mg, 0.62 mmol) and followed by 13a (13.4 mg, 0.12 mmol). The resulting mixture was stirred at r.t. over night, and evaporated. The residue was triturated with methanol and filtered to provide 13 (51 mg, 86%). 1H-NMR (300 MHz, DMSO-d$_6$): δ=2.45-2.50 (m, 4H), 2.69 (s, 6H), 2.70-2.74 (m, 2H), 3.03 (t, 4H), 3.71-3.78 (m, 8H), 4.24 (t, 2H), 7.28 (s, 2H), 8.21 (s, 1H), 9.52 (s, 2H). LC-MS [M+H]$^+$: 482.2.

Example 14

6-(2-difluoromethyl-benzoimidazol-1-yl)-9-[2-(4-methanesulfonyl-piperazin-1-yl)-ethyl]-2-morpholin-4-yl-9H-purine 2.88 (t, 2H), 3.22 (t, 4H), 3.80-3.90 (m, 8H), 4.29 (t, 2H), 7.27-7.63 (m, 3H), 7.74-7.77 (m, 1H), 7.91-7.94 (m, 2H). LC-MS [M+H]⁺: 562.1

Example 15

5-[2-morpholin-4-yl-9-(3-piperazinylpropyl)purin-6-yl]pyrimidine-2-ylamine

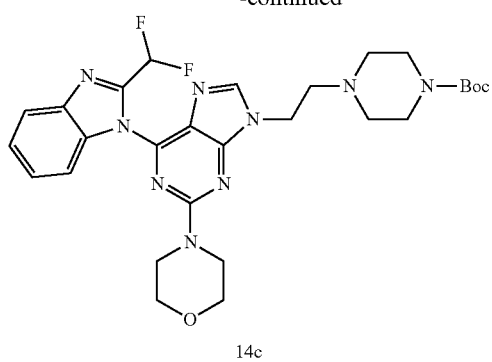

14c

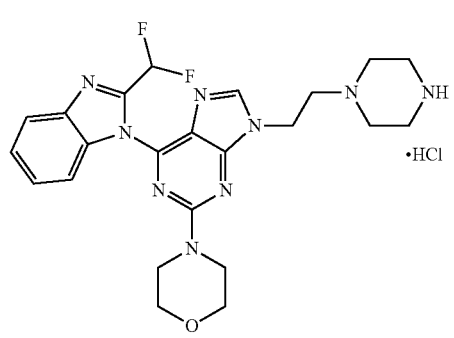

14d

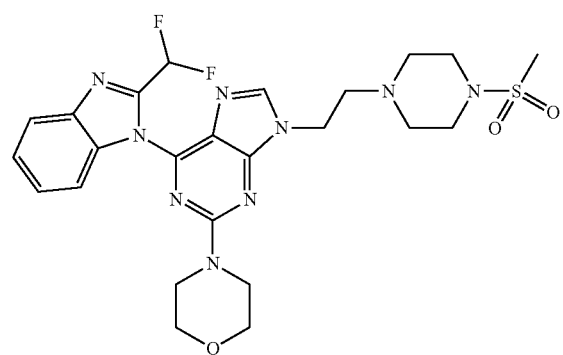

14

Step 1: To a solution of 14a (599 mg, 3.57 mmol) in DMF (20 mL) was added NaH (143 mg, 3.57 mmol) with ice-bath. The resulting mixture was stirred for 15 min. at 0-5° C. and was added 10b (1.43 g, 3.57 mmol). The reaction mixture was stirred at r.t. over night and evaporated to remove DMF. The residue was purified by column chromatography (PE:EA=1:2) to give 14b (1.13 g, 59.5% yield).

Step 2: The procedure from 14b to 14b was similar to that of 10c to 10f, to provide 14 (305 mg, 78.1% from 14b). 1H-NMR (300 MHz, CDCl₃): δ=2.67 (t, 4H), 2.77 (s, 3H),

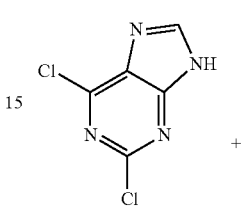

A1

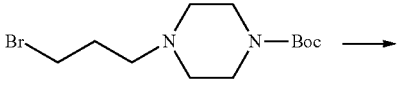

15a

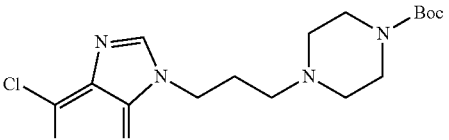

15b

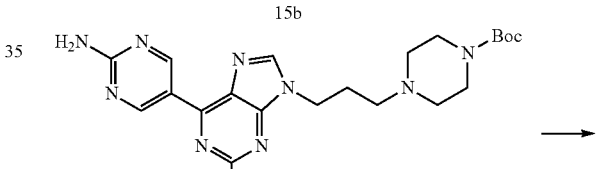

15c

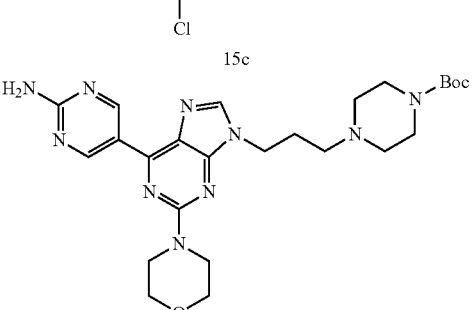

15d

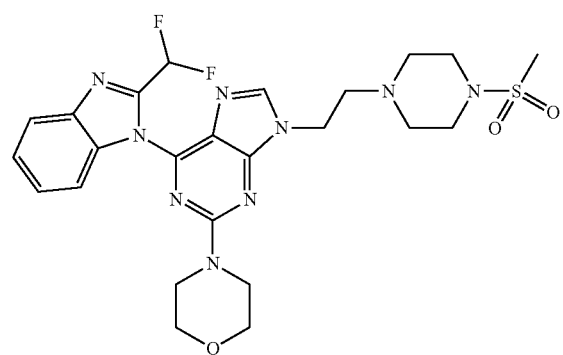

15

Step 1: The procedure from A1 to 15b was similar to that of A1 to 10b which provided 15b (1.52 g, 58%).

Step 2: The procedure from 15b to 15 was similar to that of 10b to 10e which provided 15 (406 mg, 82.7% from 15c). 1 H-NMR (300 MHz, DMSO-d$_6$): δ=2.34-2.40 (m, 2H), 3.06-3.48 (m, 10H), 3.72-3.82 (m, 10H), 4.27 (t, 2H), 8.34 (s, 1H), 9.59 (s, 2H), 9.80 (brs, 2H). LC-MS [M+H]$^+$: 425.2.

Example 16

1-{3-[6-(2-aminopyrimidin-5-yl)-2-morpholin-4-ylpurin-9-yl]propyl}-4-(methylsulfonyl)piperazine

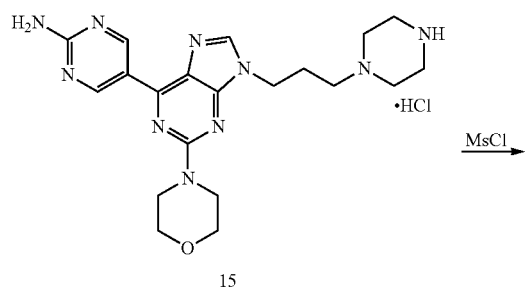

15

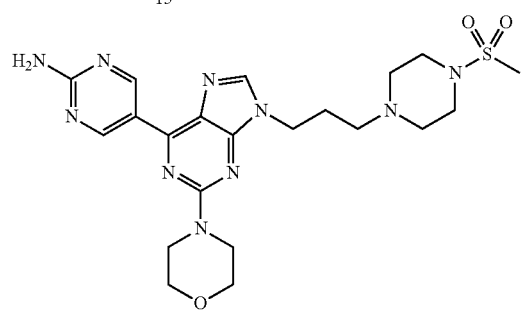

16

The procedure from 15 to 16 was similar to that of 10e to 10f which provided 16 (43 mg, 72%). 1H-NMR (300 MHz, DMSO-d$_6$): δ=1.96-2.03 (m, 2H), 2.32 (t, 2H), 2.43 (t, 4H), 2.82 (s, 3H), 3.03 (t, 4H), 3.71-3.78 (m, 8H), 4.17 (t, 2H) 7.28 (s, 2H), 8.20 (s, 1H), 9.52 (s, 2H). LC-MS [M+H]$^+$: 503.2.

Example 17

(4-{3-[6-(2-aminopyrimidin-5-yl)-2-morpholin-4-ylpurin-9-yl]propyl}piperazinyl)-N,N-dimethylcarboxamide

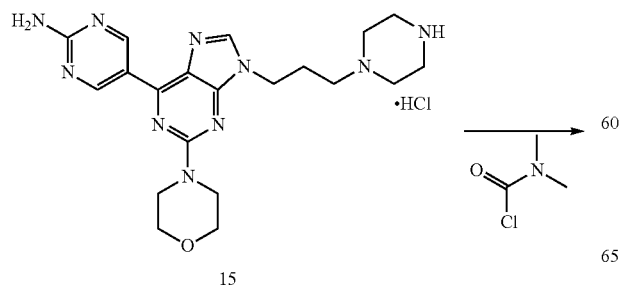

15

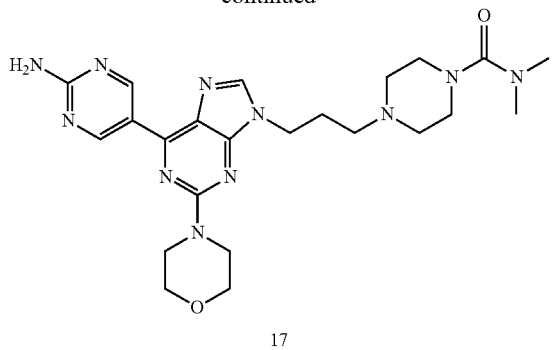

17

The procedure from 15 to 17 was similar to that of 11 to 13 which provided 17 (46 mg, 78%). 1H-NMR (300 MHz, DMSO-d$_6$): δ=1.96-2.00 (m, 2H), 2.26-2.32 (m, 6H), 2.71 (s, 6H), 3.06 (t, 4H), 3.71-3.79 (m, 8H), 4.17 (t, 2H) 7.28 (s, 2H), 8.20 (s, 1H), 9.52 (s, 2H). LC-MS [M+H]$^+$: 496.2.

Example 18

1-[6-(2-aminopyrimidin-5-yl)-2-morpholin-4-ylpurin-9-yl]-2-ethylpropan-2-ol

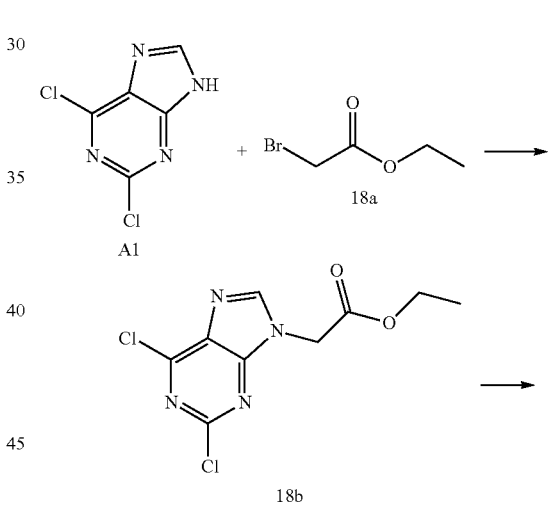

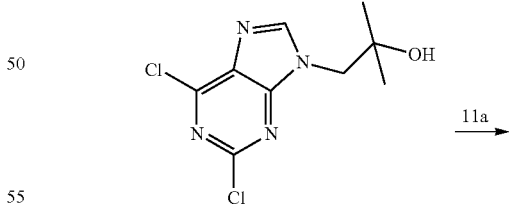

18c

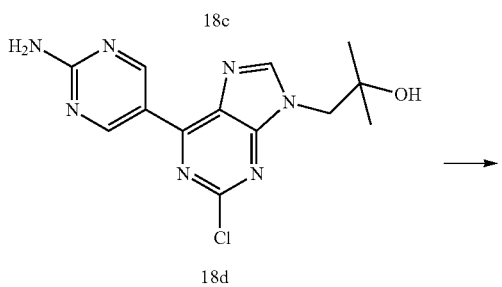

18d

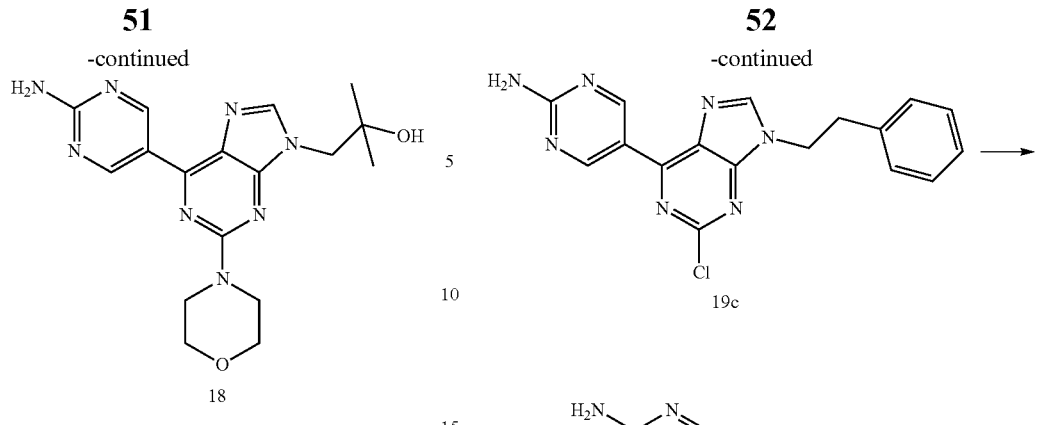

Step 1: The procedure from A1 to 18b was similar to that of A1 to A3 which provided 18b (8.77 g, 58.5%).

Step 2: To a mixture of Mg (3.5 g, 0.146 mol) in THF (32 mL) was added dropwise a solution of $CH_3Br$ in THF (4.56M, 2 mL) under heat to keep the reaction reflux slightly. After the addition was done, the mixture was heated under reflux for another 2 hours, cooled to r.t. which was added dropwise to a stirred and cooled (ice-bath) solution of 18b (1.5 g, 5.45 mmol) in THF (20 mL). The resulting mixture was stirred for 2 h, then quenched with sat. $NH_4Cl$ solution and extracted with EA. The combined extract was dried over $Na_2SO_4$ and concentrated. The residue was purified by column chromatography (EA:PE=1:3) to give 18c (490 mg, 34.5%).

Step 3: The procedure from 18c to 18 was similar to that of 10b to 11c in example 11 which provided 18 (94 mg, 13.4%). 1H-NMR (300 MHz, DMSO-$d_6$): δ=1.10 (s, 6H), 3.70-3.78 (m, 8H), 4.03 (s, 2H), 4.87 (s, 1H), 7.28 (s, 2H), 8.09 (s, 1H), 9.53 (s, 2H). LC-MS [M+H]$^+$: 371.1.

The procedure from A1 to 19 was similar to that of A1 to 15d in example 15 which provided 19 (104 mg, 8.7%). 1H-NMR (300 MHz, CDCl$_3$): δ=3.17 (t, 2H), 3.83-3.93 (m, 8H), 4.36 (t, 2H), 5.33 (s, 2H), 7.08-7.11 (m, 2H), 7.23-7.31 (m, 3H), 7.43 (s, 1H), 9.61 (s, 2H). LC-MS [M+H]$^+$: 403.2.

Example 19

5-[2-morpholin-4-yl-9-(2-phenylethyl)purin-6-yl]pyrimidine-2-ylamine

Example 20

1-[6-(2-aminopyrimidin-5-yl)-2-morpholin-4-ylpurin-9-yl]-3-morpholin-4-ylpropan-2-ol

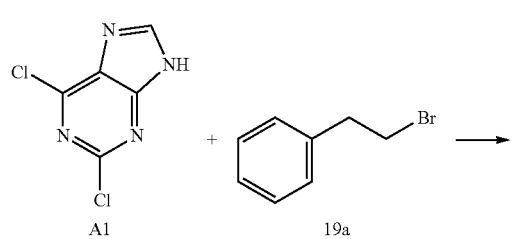

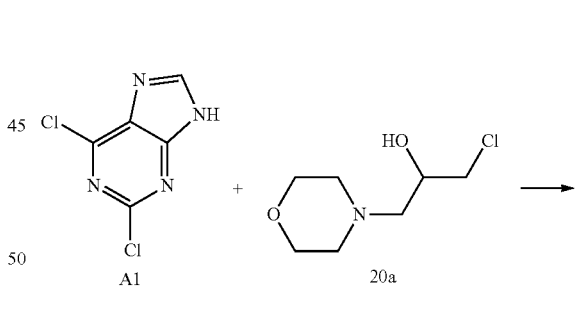

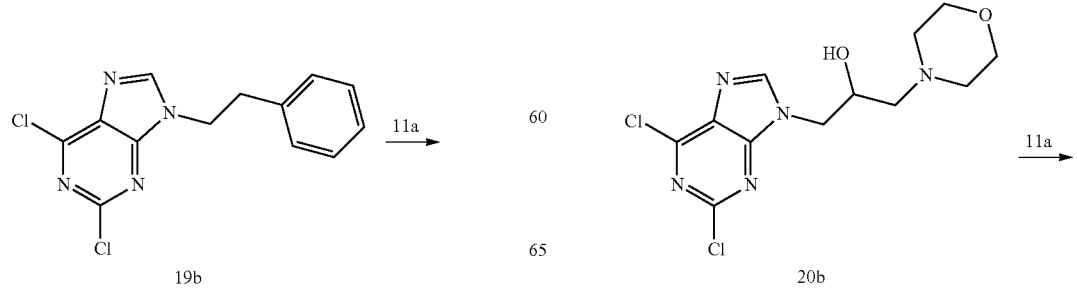

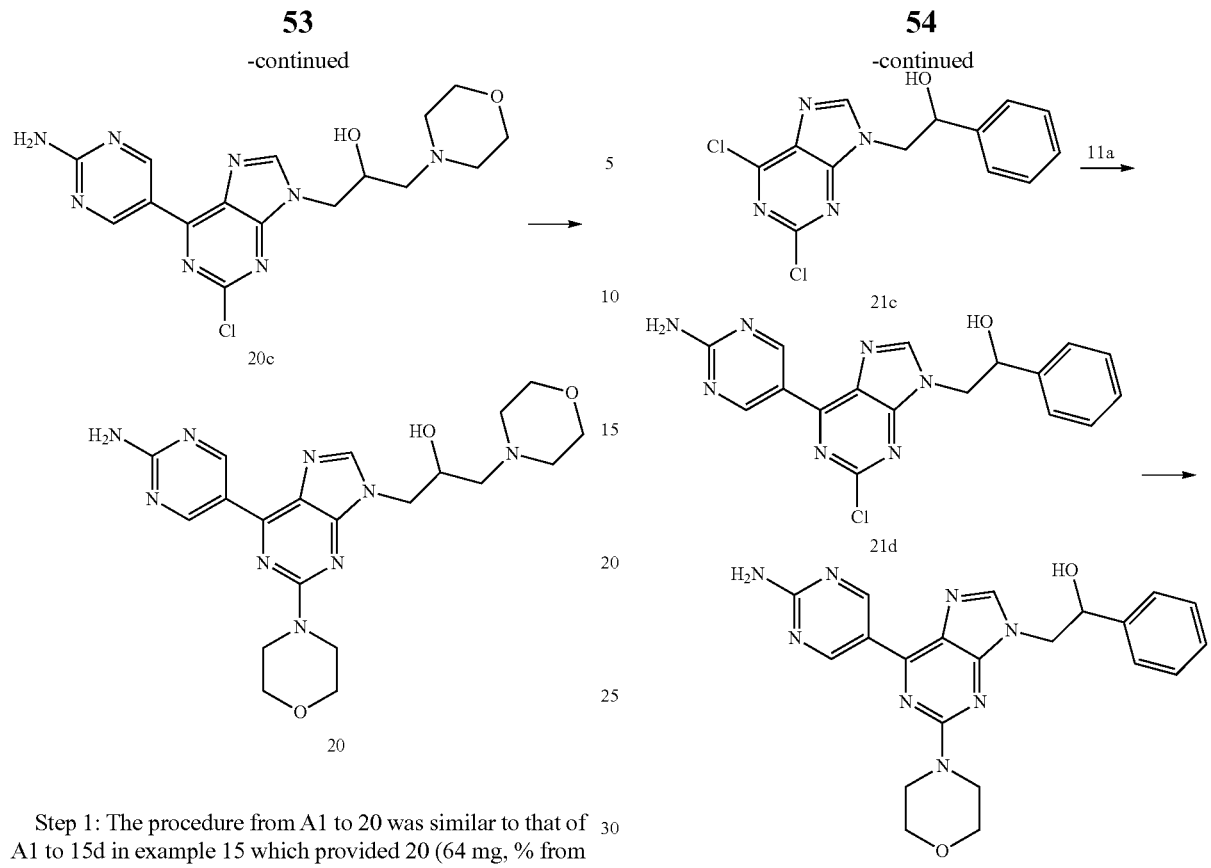

Step 1: The procedure from A1 to 20 was similar to that of A1 to 15d in example 15 which provided 20 (64 mg, % from 20b). 1H-NMR (300 MHz, DMSO-$d_6$): δ=2.31-2.44 (m, 6H), 3.55 (t, 4H), 3.71-3.76 (m, 8H), 3.96-4.05 (m, 2H), 4.31-4.36 (m, 1H), 5.09 (d, 1H), 7.28 (s, 2H), 8.12 (s, 1H), 9.52 (s, 2H). LC-MS [M+H]$^+$: 442.2.

Example 21

2-[6-(2-aminopyrimidin-5-yl)-2-morpholin-4-ylpurin-9-yl]-1-phenyl ethan-1-ol

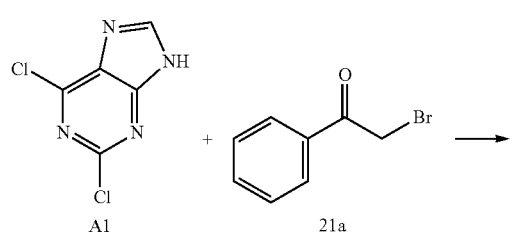

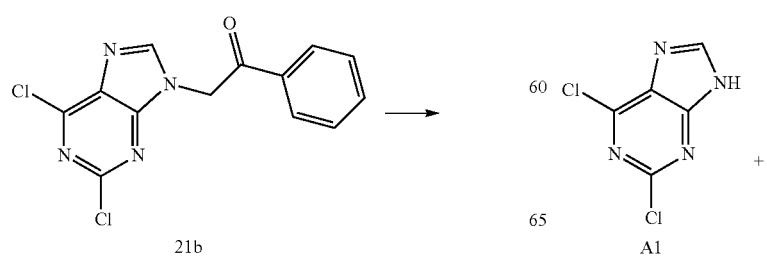

Step 1: The procedure from A1 to 21b was similar to that of A to 2a which provided 21b (380 mg, 41%).

Step 2: To a solution of 21b (380 mg, 1.24 mmol) in methanol (15 mL) was added NaBH$_4$ (47 mg, 1.24 mmol) cooled with ice-bath. The mixture was stirred at 0° C. for 0.5 h and quenched with con. HCl to pH=7-8. Excess solvent was removed and the residue was purified by column chromatography (EA:PE=2:5) to give 21c (200 mg, 52% yield).

Step 3: The procedure from 21c to 21 was similar to that of 10b to 11c which provided 21 (62 mg, 23% from 21c). 1H-NMR (300 MHz, DMSO-$d_6$): δ=3.68-3.77 (m, 8H), 4.24-4.27 (m, 2H), 5.02-5.05 (m, 1H), 5.77 (d, 1H), 7.26-7.38 (m, 7H), 8.08 (s, 1H), 9.51 (s, 2H). LC-MS [M+H]$^+$: 419.1.

Example 22

4-{2-[6-(2-aminopyrimidin-5-yl)-2-morpholin-4-ylpurin-9-yl]ethyl}phenyl-4-methylpiperazinyl ketone

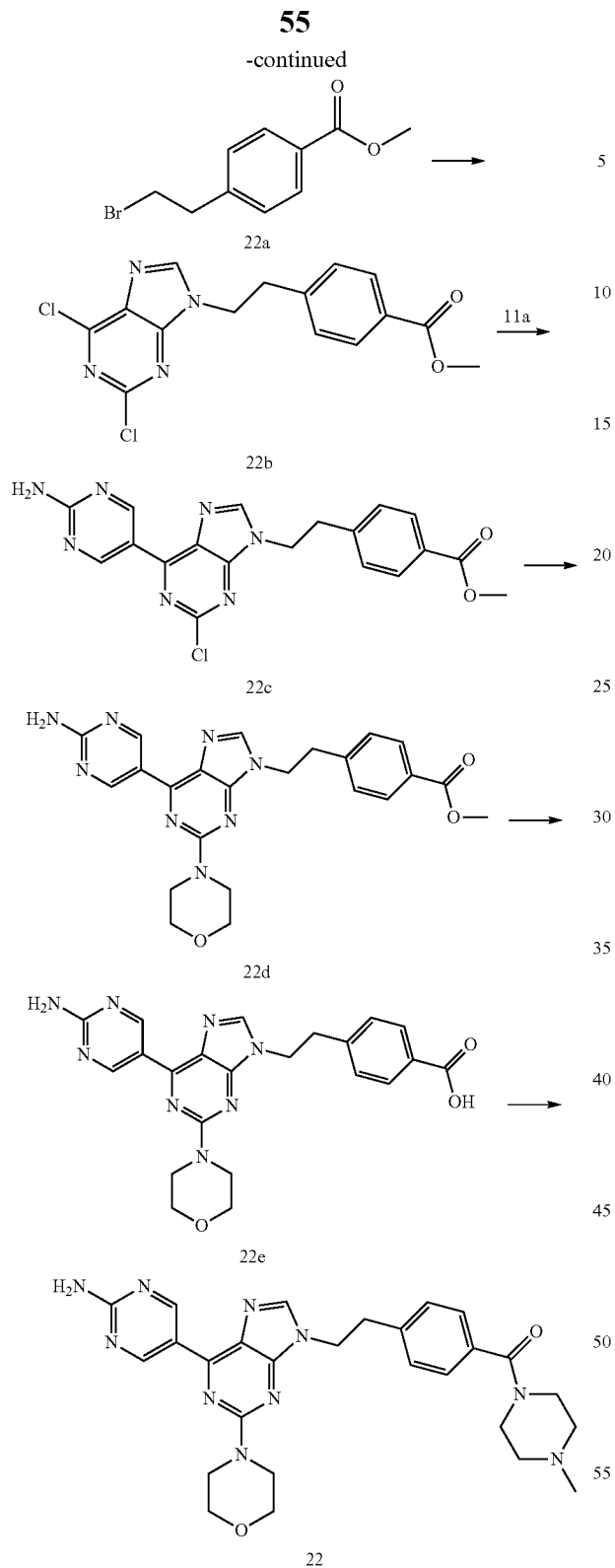

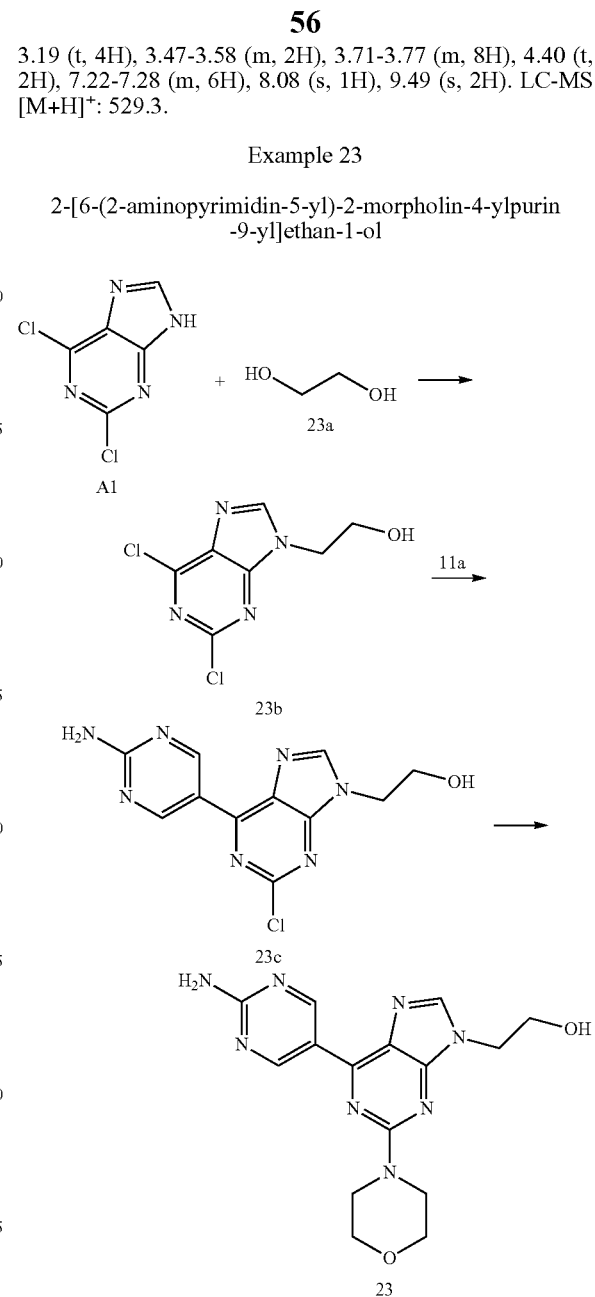

3.19 (t, 4H), 3.47-3.58 (m, 2H), 3.71-3.77 (m, 8H), 4.40 (t, 2H), 7.22-7.28 (m, 6H), 8.08 (s, 1H), 9.49 (s, 2H). LC-MS [M+H]+: 529.3.

Example 23

2-[6-(2-aminopyrimidin-5-yl)-2-morpholin-4-ylpurin-9-yl]ethan-1-ol

Step 1: The procedure from A1 to 22d was similar to that of A1 to 15d which provided 22d (140 mg, 36%).

Step 2: The procedure from 22d to 22 was similar to that of 7c to 7e which provided 22 (48 mg, 30% from 22d). 1H-NMR (300 MHz, DMSO-$d_6$): δ=2.15 (s, 3H), 2.21-2.28 (m, 4H), Step 1: A mixture of A1 (5.67 g, 30 mmol), 23a (2.8 g, 45 mmol) and Ph$_3$P (11.8 g, 45 mmol) in THF (200 mL) was stirred at r.t. for 1 hour under N$_2$ atmosphere, then was added DIAD (9.09 g, 45 mmol) dropwise under ice-bath. The resulting mixture was stirred at r.t. over 2 days. The solvent was evaporated and the residue was purified by column chromatography (PE:EA:DCM=1:1:0.4) to give 23b (5.05 g, 72% yield).

Step 2: To a solution of 23b (3.50 g, 15 mmol) and 11a (3.32 g, 15 mmol) in a mixted solvent of acetonitrile (50 mL)/water (50 mL) was added Na$_2$CO$_3$ (3.18 g, 30.0 mmol) and Pd(Ph$_3$P)$_4$ (870 mg, 0.75 mmol). The mixture was degassed three times with N$_2$, and then heated at 60° C. overnight. The solvent was evaporated and the residue was purified by column chromatography (DCM: CH$_3$OH=6:1) to give 23c (2.41 g, 55% yield).

Step 3: The procedure from 23c to 23 was similar to that of A5 to A6 which provided 23 (1.75 g, 62%). 1H-NMR (300 MHz, DMSO-$d_6$): δ=3.71-3.77 (m, 10H), 4.16 (t, 2H), 4.98 (t, 1H), 7.28 (s, 2H), 8.15 (s, 1H), 9.52 (s, 2H). LC-MS [M+H]+: 343.1.

Example 24

2-(2-morpholin-4-yl-6-pyrazol-4-ylpurin-9-yl)ethan-1-ol

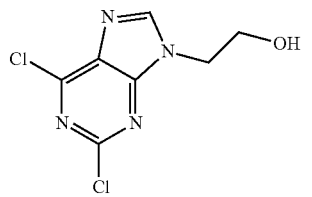

23b

+

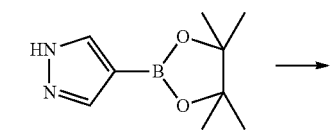

24a

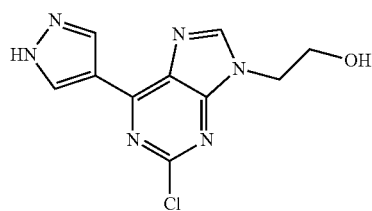

24b

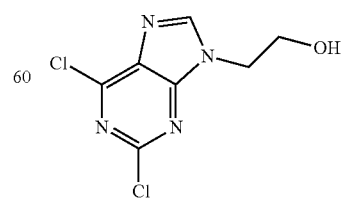

24

The procedure from 23b to 24 was similar to that of 10b to 11c which provided 24 (21 mg, 6.7%). 1H-NMR (300 MHz, DMSO-d$_6$): δ=3.69-3.79 (m, 10H), 4.15 (t, 2H), 4.97 (t, 1H), 8.10 (s, 1H), 8.41 (s, 1H), 8.67 (s, 1H), 13.28 (s, 1H). LC-MS [M+H]$^+$: 316.1.

Example 25

2-(6-(1H-indazol-4-yl)-2-morpholin-4-ylpurin-9-yl)ethan-1-ol

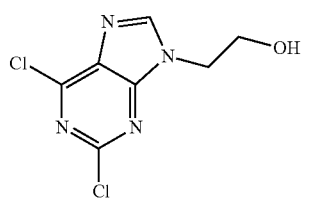

23b

+

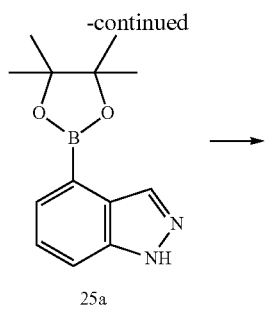

25a

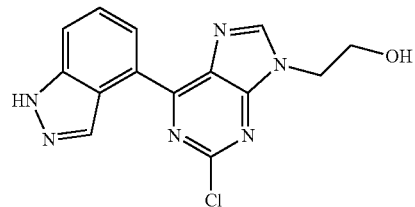

25b

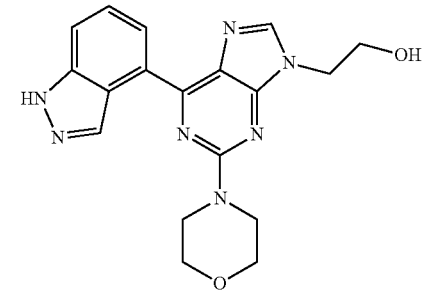

25

The procedure from 23b to 25 was similar to that of 10b to 11c which provided 25 (44 mg, 13%). 1H-NMR (300 MHz, DMSO-d$_6$): δ=3.78-3.86 (m, 10H), 4.22 (t, 2H), 5.00-5.01 (m, 1H), 7.53 (t, 1H), 7.73 (d, 1H), 8.22 (s, 1H), 8.72 (s, 1H), 8.80 (d, 1H), 13.28 (s, 1H). LC-MS [M+H]$^+$: 366.1.

Example 26

2-(2-morpholin-4-yl-6-pyrrolo[2,3-b]pyridin-5-ylpurin-9-yl)ethan-1-ol

23b

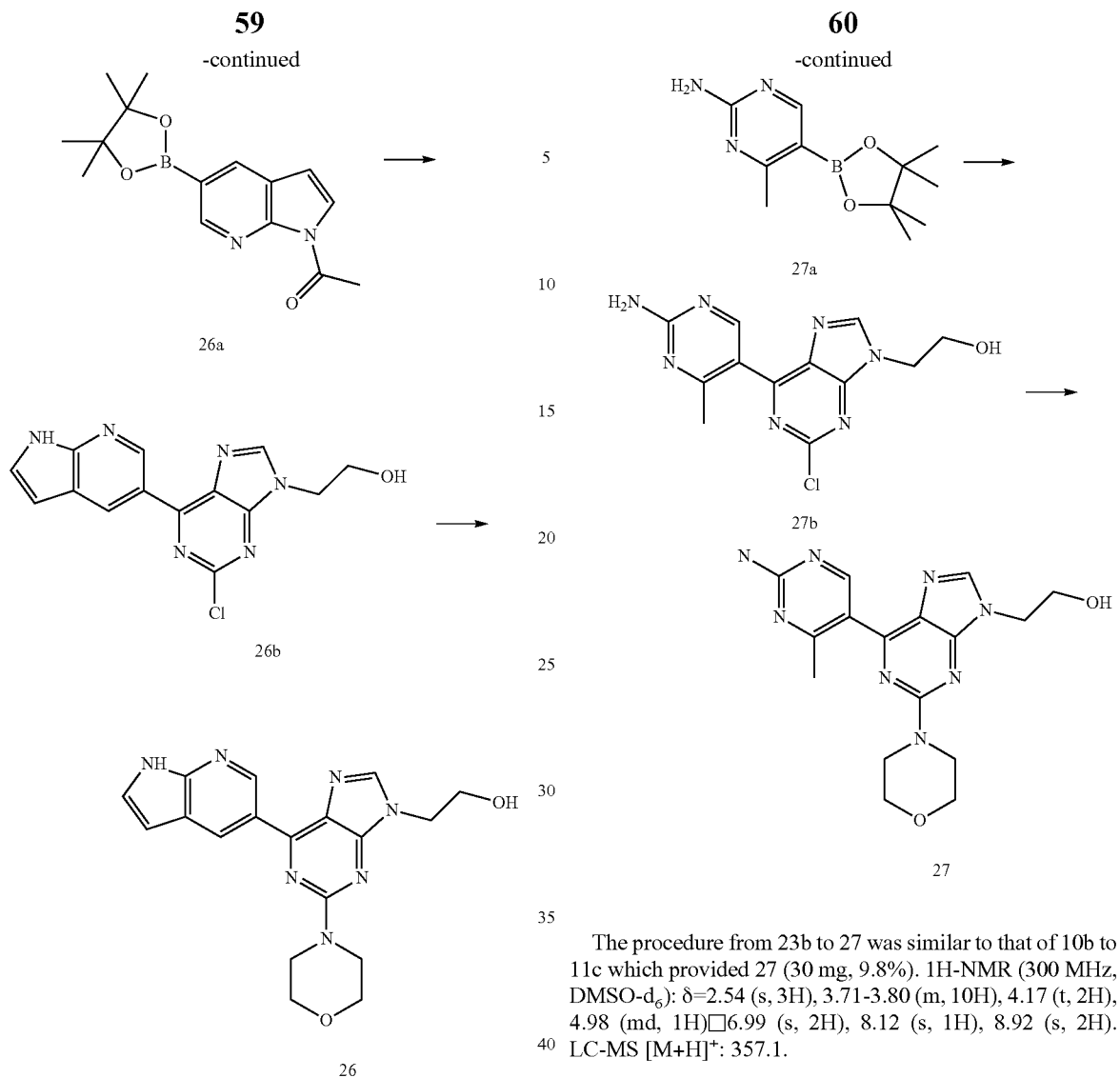

The procedure from 23b to 26 was similar to that of 10b to 11c which provided (70 mg, 28%). 1H-NMR (300 MHz, DMSO-d$_6$): δ=3.73-3.86 (m, 10H), 4.20 (t, 2H), 5.01 (t, 1H), 6.62-6.64 (m, 1H), 7.55 (t, 1H), 8.21 (s, 1H), 9.35 (d, 1H), 9.68 (d, 1H), 11.91 (s, 1H). LC-MS [M+H]$^+$: 366.1.

Example 27

2-[6-(2-amino-4-methylpyrimidin-5-yl)-2-morpholin-4-ylpurin-9-yl]ethan-1-ol

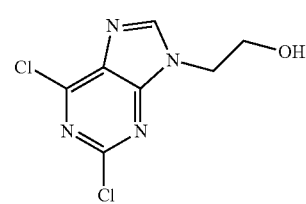

The procedure from 23b to 27 was similar to that of 10b to 11c which provided 27 (30 mg, 9.8%). 1H-NMR (300 MHz, DMSO-d$_6$): δ=2.54 (s, 3H), 3.71-3.80 (m, 10H), 4.17 (t, 2H), 4.98 (md, 1H)☐6.99 (s, 2H), 8.12 (s, 1H), 8.92 (s, 2H). LC-MS [M+H]$^+$: 357.1.

Example 28

2-{6-[2-(difluoromethyl)benzimidazol-1-yl]-2-morpholin-4-ylpurin-9-yl}ethan-1-ol

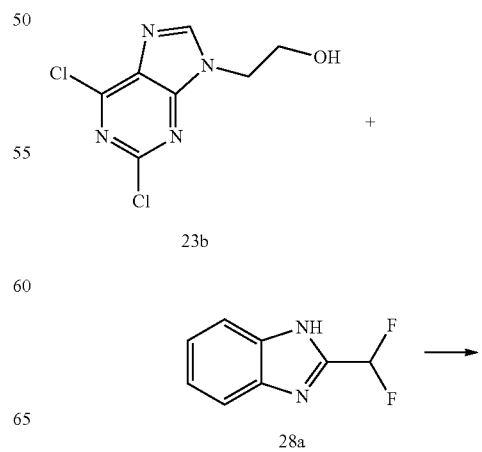

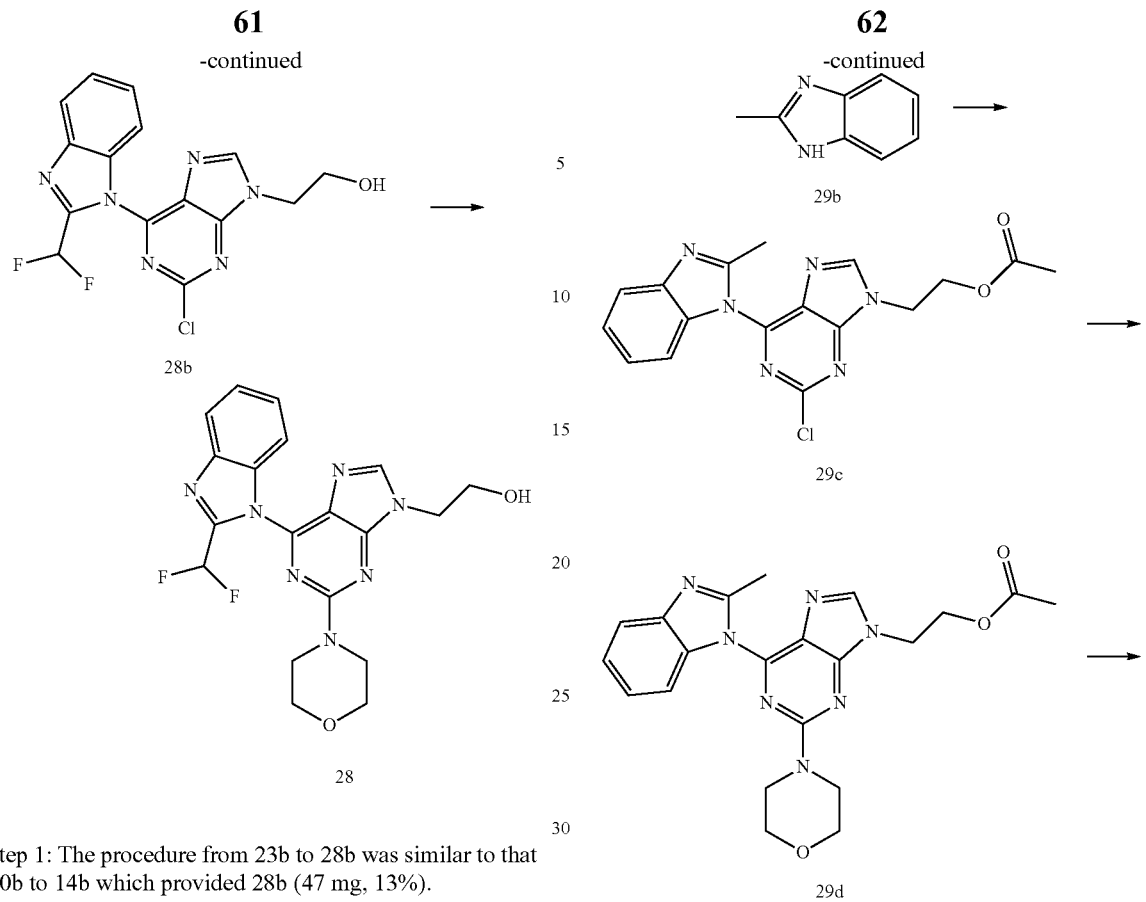

Step 1: The procedure from 23b to 28b was similar to that of 10b to 14b which provided 28b (47 mg, 13%).

Step 2: The procedure from 28b to 28 was similar to that of A5 to A6 which provided 28 (52 mg, 98%). 1H-NMR (300 MHz, CDCl$_3$): δ=3.80 (brs, 1H), 3.84-3.87 (m, 8H), 4.08 (t, 2H), 4.34 (t, 2H), 7.38-7.44 (m, 3H), 7.72-7.75 (m, 1H), 7.88-7.92 (m, 2H). LC-MS [M+H]$^+$: 416.1.

Example 29

2-[6-(2-methylbenzimidazolyl)-2-morpholin-4-ylpurin-9-yl]ethan-1-ol

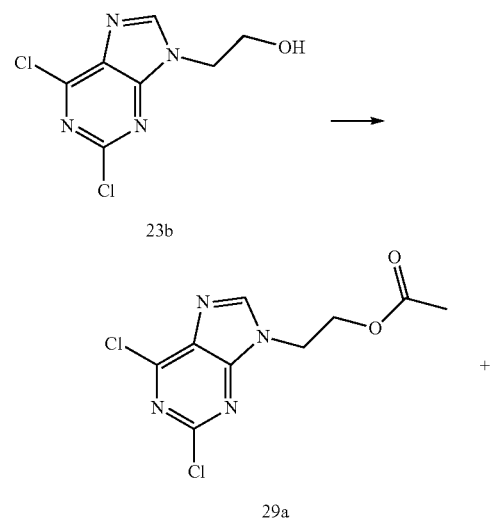

Step 1: To a suspension of 23b (2.33 g, 10 mmol) and Et$_3$N (2.02 g, 20 mmol) in DCM (30 mL) was added Ac$_2$O (1.53 g, 15 mmol) dropwise at 0° C. The resulting mixture was stirred at r.t. for 3 h, then was added sat. NaHCO$_3$ until pH=8~9. The organic phase was separated and the aqueous phase extracted with DCM twice. The combined organic layer was dried over anhydrous MgSO$_4$ and concentrated to give crude 29a (2.90 g).

Step 2: The procedure from 29a to 29d was similar to that of 10b to 14c which provided 29d (44 mg, 10.4%).

Step 3: To a solution of 29d (44 mg, 0.10 mmol) in methanol (3 mL) was added 1N NaOH (0.25 mL) in water (5 mL). The mixture was stirred at r.t. for 2 h. The solvent was evaporated and water was added. The aqueous layer was extracted with DCM/methanol (10:1). The combined extract was dried over MgSO$_4$, concentrated and purified by prep-TLC to give 29 (39.5 mg, ca. 100%). 1H-NMR (300 MHz,CDCl$_3$): δ=2.78

(s, 3H), 3.80-3.86 (m, 8H), 4.09 (t, 2H), 4.35 (t, 2H), 7.20-7.31 (m, 2H), 7.53 (d, 1H), 7.72 (d, 1H), 7.85 (s, 1H). LC-MS [M+H]+: 380.1.

Example 30

(ethylamino)-N-{4-[9-(2-hydroxyethyl)-2-morpholin-4-ylpurin-6-yl]phenyl}carboxamide

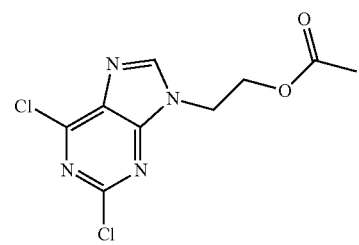

29a

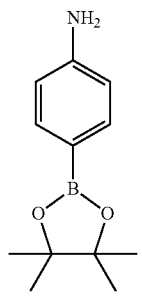

30a

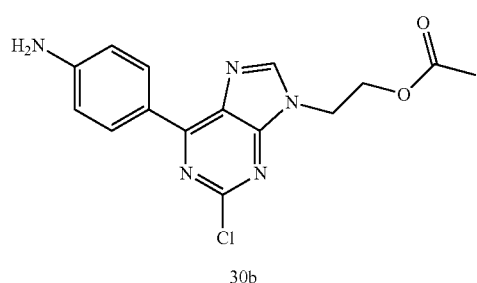

30b

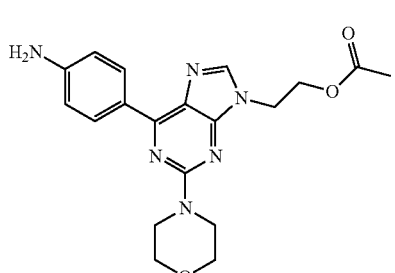

30c

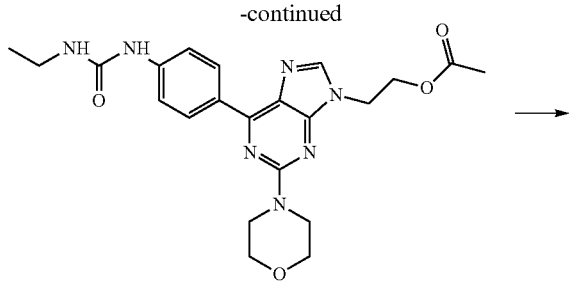

30e

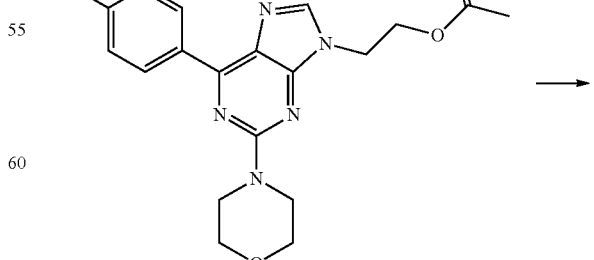

30

Step 1: The procedure from 29a to 30c was similar to that of 10b to 11c which provided 30c (178 mg, 11.5%).

Step 2: To a solution of 30c (44 mg, 0.12 mmol) in DCM (5 mL) was added DIEA (30 mg, 0.23 mmol) followed by 30d (13 mg, 0.18 mmol). The mixture was stirred at r.t. for 2 days and then evaporated. The residue was dissolved in water and extracted with DCM. The extract was dried over MgSO4, concentrated and purified by prep-TLC (DCM:MeOH=10:1) to give 30e (17.6 mg, 34%)

Step 3: The procedure from 30e to 30 was similar to that of 29d to 29 which provided 30 (3 mg, 18.7%). 1H-NMR (300 MHz, DMSO-d6): δ=1.07 (t, 3H), 3.08-3.15 (m, 2H), 3.72-3.80 (m, 10H), 4.17 (t, 2H), 4.98-4.99 (m, 1H), 6.23 (t, 1H), 7.56 (d, 2H), 8.14 (s, 1H), 8.70 (d, 2H), 8.77 (s, 1H). LC-MS [M+H]+: 412.1.

Example 31

2-[6-(4-aminophenyl)-2-morpholines-ylpurin-9-yl]ethan-1-ol

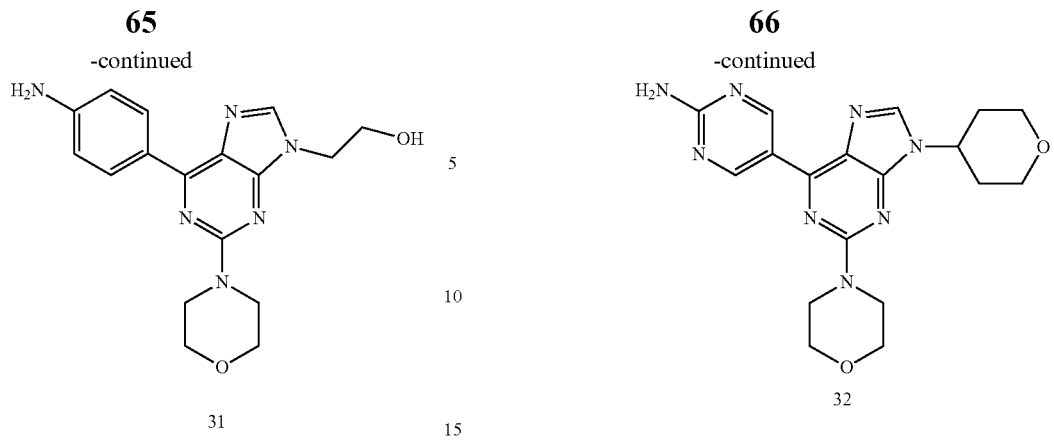

The procedure from 30c to 31 was similar to that of 29d to 29 which provided 30 (120 mg, 100%). 1H-NMR (300 MHz, DMSO-d$_6$): δ=3.72-3.77 (m, 10H), 4.15 (t, 2H), 4.98 (t, 1H), 5.72 (s, 2H), 6.66 (d, 2H), 8.07 (s, 1H), 8.58 (d, 2H). LC-MS [M+H]$^+$: 341.1.

The procedure from A1 to 32 was similar to that of A1 to 23 which provided 32 (1.2 g, 19%). 1H-NMR (300 MHz, DMSO-d$_6$): δ=1.93-1.98 (m, 2H), 2.18-2.24 (m, 2H), 3.47-3.55 (m, 2H), 3.71-3.79 (m, 8H), 3.98-4.03 (m, 2H), 4.56-4.64 (m, 1H), 7.29 (s, 2H), 8.33 (s, 1H), 9.51 (s, 2H). LC-MS [M+H]$^+$: 383.2.

Example 32

5-(9-(2H-3,4,5,6-tetrahydropyran-4-yl)-2-morpholin-4-ylpurin-6-yl) pyrimidine-2-ylamine Example 33

3-(9-(2H-3,4,5,6-tetrahydropyran-4-yl)-2-morpholin-4-ylpurin-6-yl) phenol

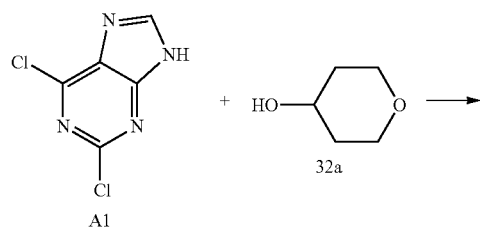

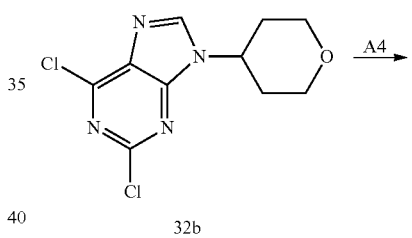

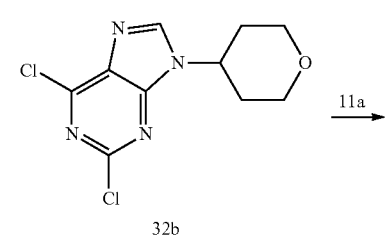

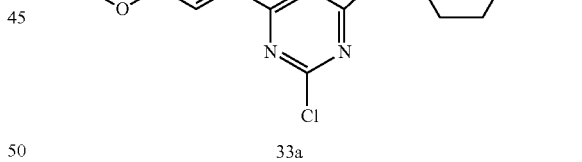

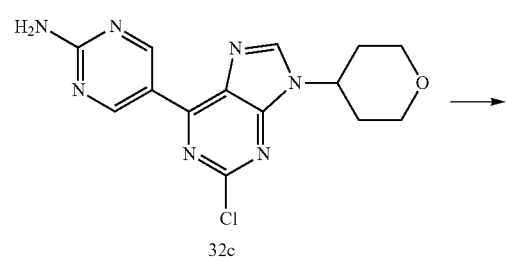

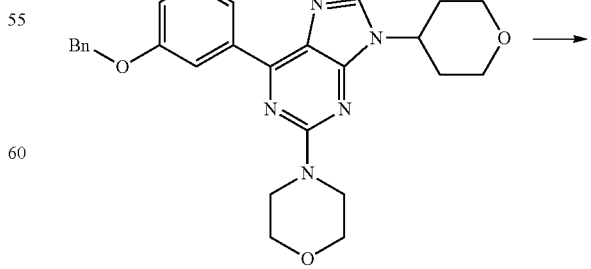

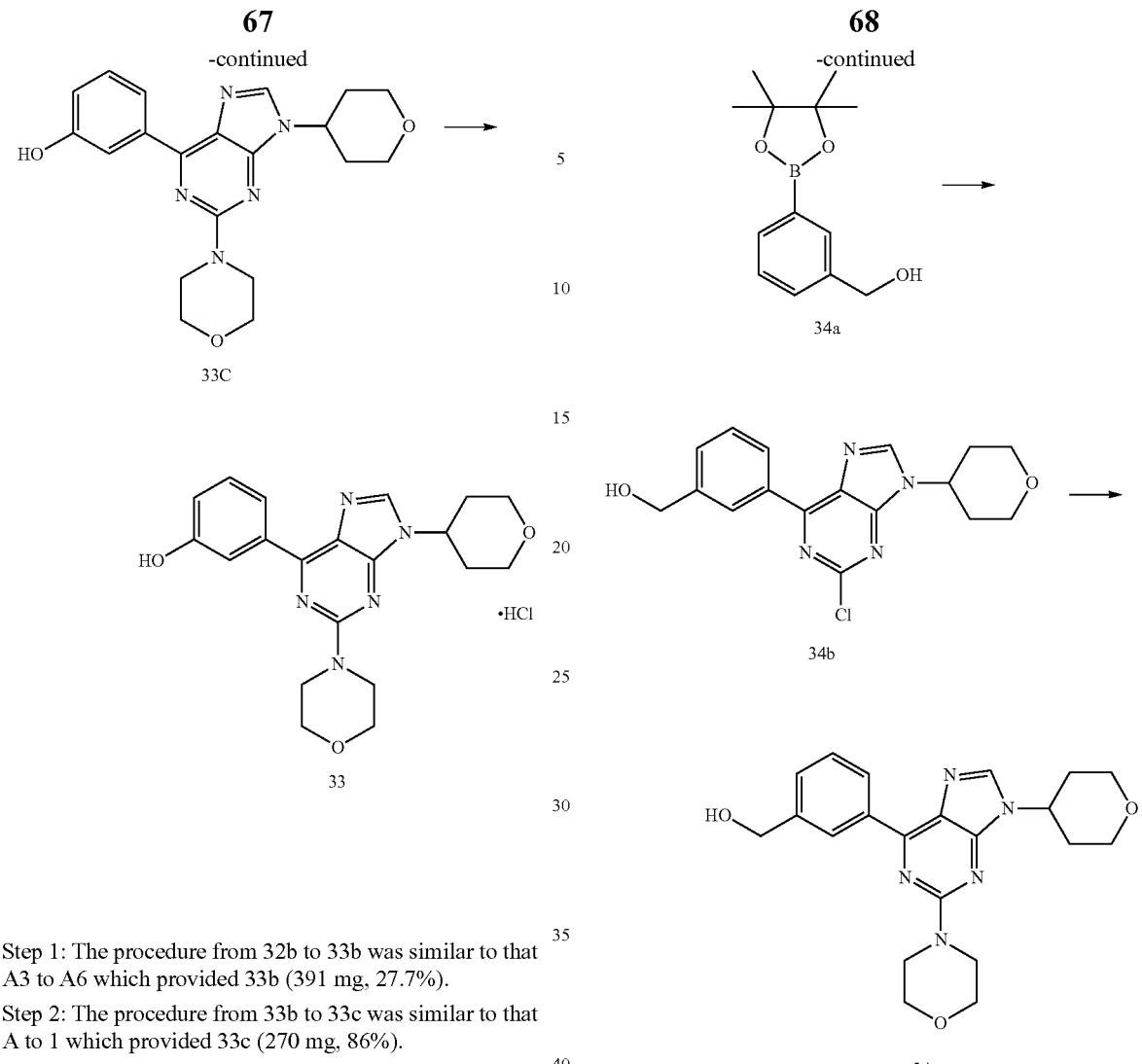

Step 1: The procedure from 32b to 33b was similar to that of A3 to A6 which provided 33b (391 mg, 27.7%).

Step 2: The procedure from 33b to 33c was similar to that of A to 1 which provided 33c (270 mg, 86%).

Step 3: To a suspension of 33c (270 mg, 0.71 mmol) in methanol (2 mL) was added a solution of HCl/Et$_2$O (10 mL). The mixture was stirred for 5 hours, then evaporated to provide 33 (298 mg). 1H-NMR (300 MHz, DMSO-d$_6$): δ=1.96-2.00 (m, 2H), 2.17-2.28 (m, 2H), 3.48-3.56 (m, 2H), 3.74-3.82 (m, 8H), 3.99-4.04 (m, 2H), 4.55-4.66 (m, 1H), 6.91-6.94 (m, 1H), 7.33 (t, 1H), 8.18 (d, 2H), 8.21 (d, 2H), 8.44 (s, 1H). LC-MS [M+H]$^+$: 382.1.

The procedure from 32b to 34 was similar to that of 23b to 23 which provided 34 (158 mg, 50%). 1H-NMR (300 MHz, CDCl$_3$): δ=2.07-2.12 (m, 2H), 2.18-2.28 (m, 3H), 3.57-3.66 (m, 2H), 3.83-3.95 (m, 8H), 4.14-4.19 (m, 2H), 4.55-4.63 (m, 1H), 4.82 (d, 2H), 7.51-7.55 (m, 2H), 7.84 (s, 1H), 8.62-8.65 (m, 1H), 8.68 (s, 1H). LC-MS [M+H]$^+$: 396.1.

Example 34

[3-(9-(2H-3,4,5,6-tetrahydropyran-4-yl)-2-morpholin-4-ylpurin-6-yl) phenyl]methan-1-ol Example 35

5-(9-(2H-3,4,5,6-tetrahydropyran-4-yl)-2-morpholin-4-ylpurin-6-yl)-4-methylpyrimidine-2-ylamine

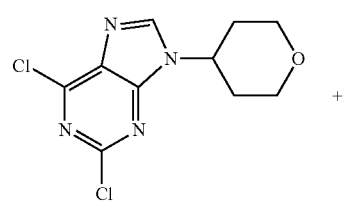

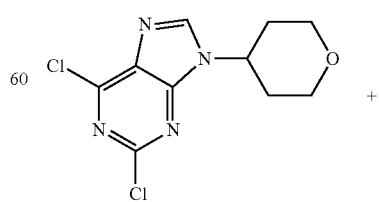

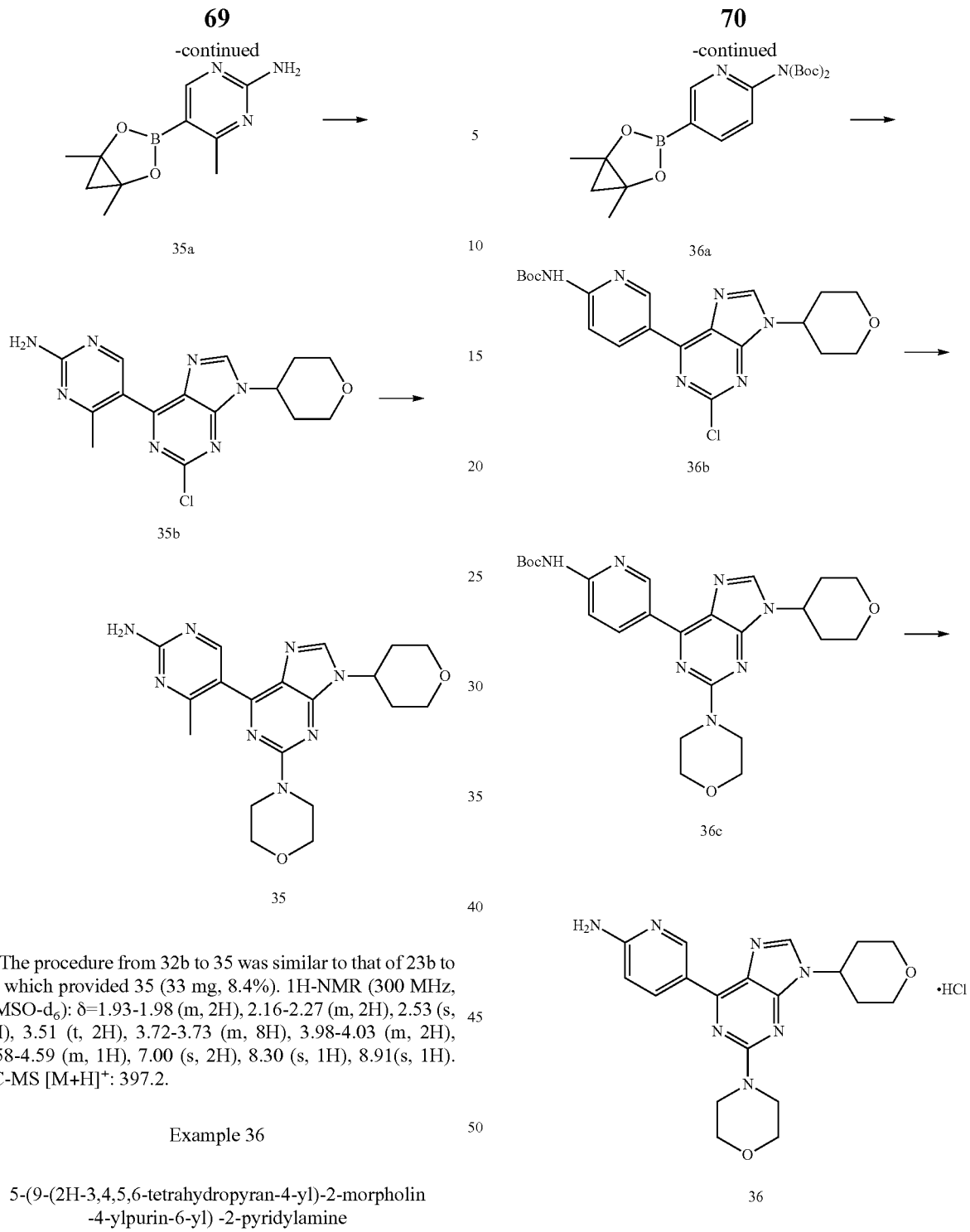

The procedure from 32b to 35 was similar to that of 23b to 23 which provided 35 (33 mg, 8.4%). 1H-NMR (300 MHz, DMSO-d$_6$): δ=1.93-1.98 (m, 2H), 2.16-2.27 (m, 2H), 2.53 (s, 3H), 3.51 (t, 2H), 3.72-3.73 (m, 8H), 3.98-4.03 (m, 2H), 4.58-4.59 (m, 1H), 7.00 (s, 2H), 8.30 (s, 1H), 8.91(s, 1H). LC-MS [M+H]$^+$: 397.2.

Example 36

5-(9-(2H-3,4,5,6-tetrahydropyran-4-yl)-2-morpholin-4-ylpurin-6-yl)-2-pyridylamine

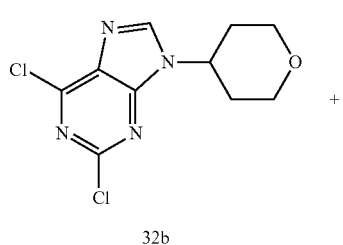

Step 1: The procedure from 32b to 36c was similar to that of 23b to 23 which provided 36c (210 mg, 49%).

Step 2: To a solution of 36c (209 mg, 0.42 mmol) in DCM (10 mL) was added dropwise TFA (3 mL). The mixture was stirred at r.t. for one hour and evaporated. The residue was dissolved in DCM and washed with sat. NaHCO$_3$. The organic layer was separated and the aqueous extracted with DCM/methanol (10:1) for several times. The combined organic layer was dried over MgSO$_4$ and concentrated to give 36 (135 mg, 81%). 1H-NMR (300 MHz, DMSO-d$_6$): δ=1.94-1.98 (m, 2H), 2.15-2.28 (m, 2H), 3.49 (t, 2H), 3.72-3.81 (m, 8H), 3.98-4.03 (m, 2H), 4.58-4.66 (m, 1H), 6.97 (brs, 3H), 7.18 (d, 2H), 8.46 (s, 1H), 8.63(brs, 1H), 9.02 (d, 1H), 9.34 (d, 1H). LC-MS [M+H]$^+$: 382.2.

Example 37

5-(9-(2H -3,4,5,6-tetrahydropyran-4-yl)-2-morpholin-4-ylpurin-6-yl)pyrimidine-2,4-diamine

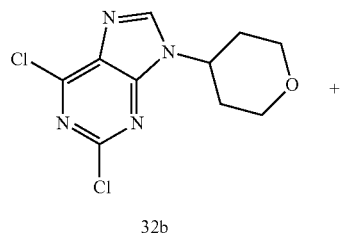

32b

+

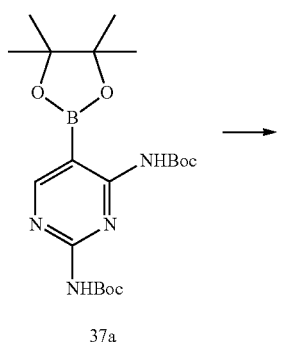

37a

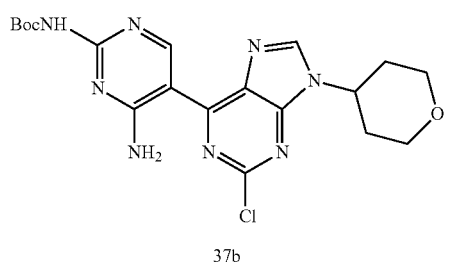

37b

37c

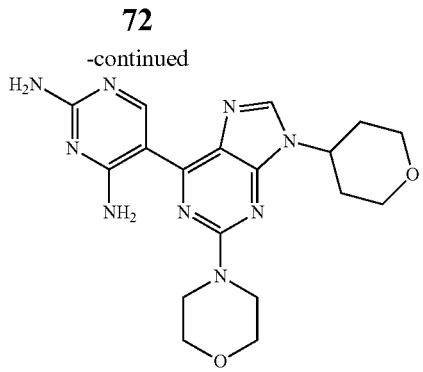

37

Step 1: The procedure from 32b to 37c was similar to that of 23b to 23 which provided 37c (209 mg, 39.6%).

Step 2: The procedure from 37c to 37 was similar to that of 10d to 10e which provided 37 (135 mg, 81%). 1H-NMR (300 MHz, DMSO-d$_6$): δ=1.93-1.98 (m, 2H), 2.13-2.26 (m, 2H), 3.51 (t, 2H), 3.65-3.75 (m, 8H), 3.98-4.03 (m, 2H), 4.55-4.63 (m, 1H), 6.61 (s, 2H), 7.13 (brs, 1H), 8.29 (s, 1H), 9.00 (brs, 1H), 9.81(s, 1H). LC-MS [M+H]$^+$: 398.2.

Example 38

5-(9-(2H-3,4,5,6-tetrahydropyran-4-yl)-2-morpholin-4-ylpurin-6-yl) pyridin-3-ol

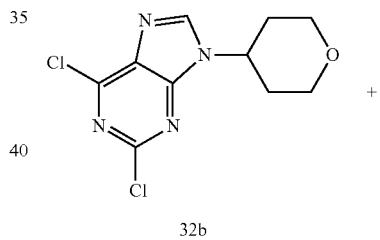

32b

+

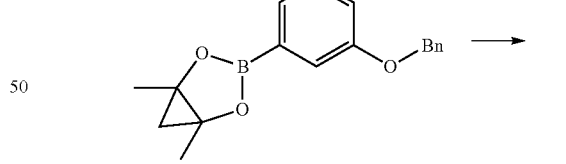

38a

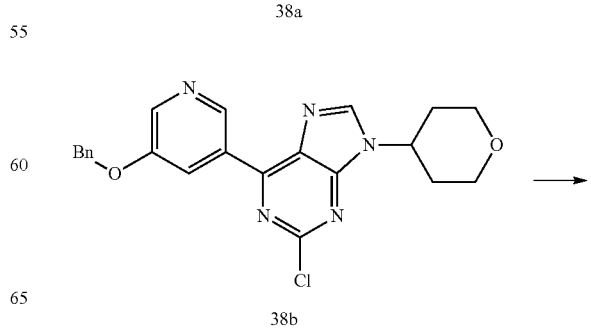

38b

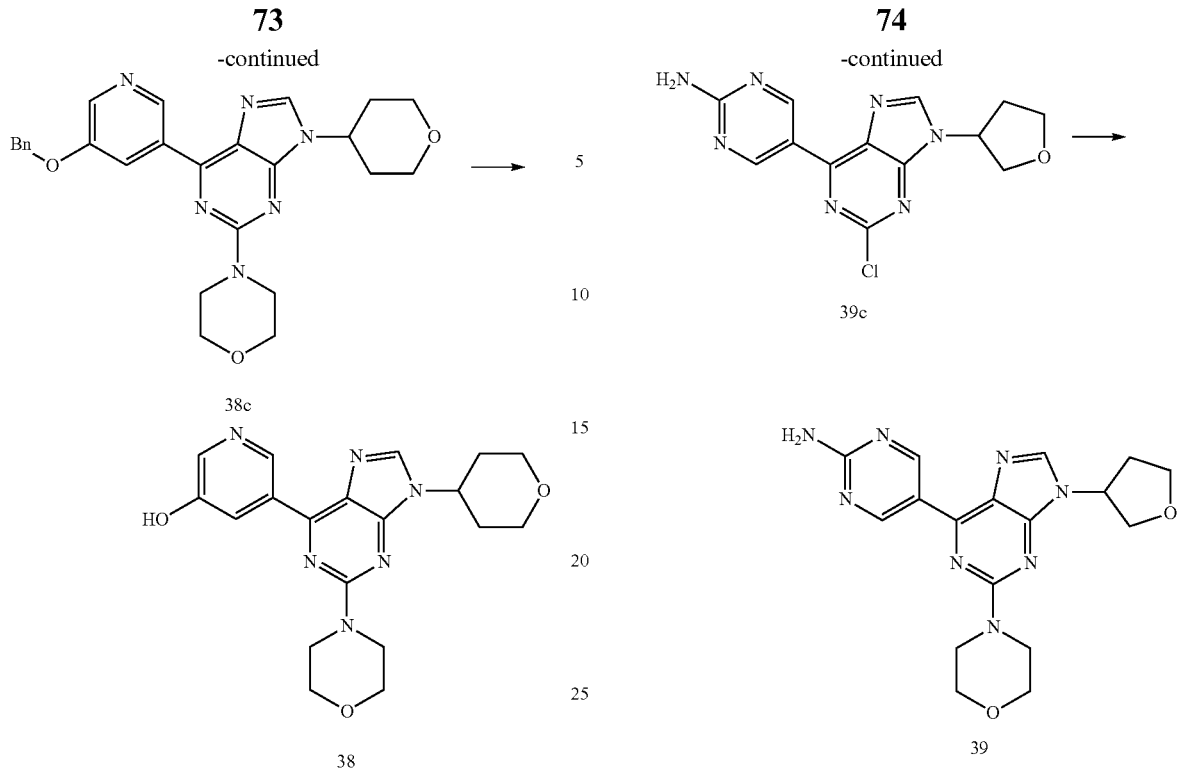

Step 1: The procedure from 32b to 38c was similar to that of 23b to 23 which provided 38c (30 mg, 21.7%).

Step 1: The procedure from 38c to 38 was similar to that of A to 1 which provided 38 (23 mg, 93.8%). 1H-NMR (300 MHz, DMSO-d$_6$): δ=1.94-1.97 (m, 2H), 2.15-2.26 (m, 2H), 3.50 (t, 2H), 3.71-3.79 (m, 8H), 3.97-4.02 (m, 2H), 4.56-4.64 (m, 1H), 8.28 (d, 1H), 8.40 (s, 1H), 8.45-8.46 (m, 1H), 9.34 (d, 1H), 10.37(brs,1H). LC-MS [M+H]$^+$: 383.2.

Example 39

5-(2-morpholin-4-yl-9-oxolan-3-ylpurin-6-yl)pyrimidine-2-ylamine

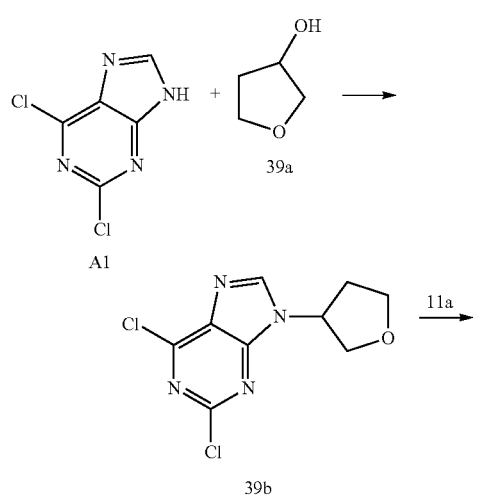

The procedure from A1 to 39 was similar to that of A1 to 23 which provided 39 (164 mg, 7.4%). 1H-NMR (300 MHz, DMSO-d$_6$): δ=2.27-2.32 (m, 1H), 2.45-2.52 (m, 1H), 3.69-3.79 (m, 8H), 3.84-4.16 (m, 4H), 5.14-5.18 (m, 1H), 7.29 (s, 2H), 8.20 (s, 1H), 9.51 (s, 2H). LC-MS [M+H]$^+$: 369.1.

Example 40 tert-butyl 4-[6-(2-aminopyrimidin-5-yl)-2-morpholin-4-ylpurin-9-yl]piperidinecarboxylate

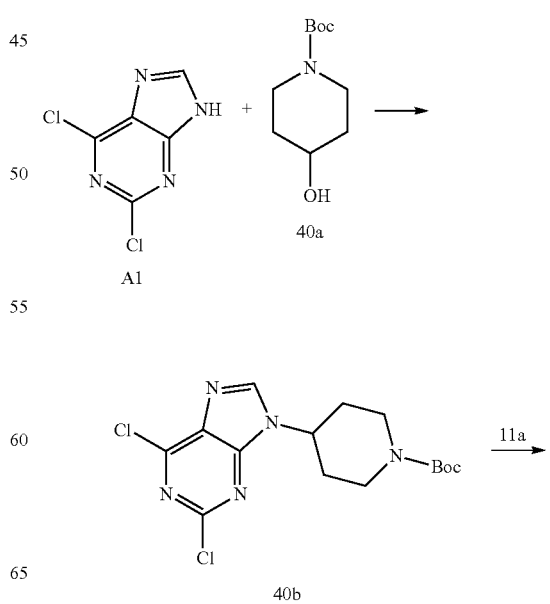

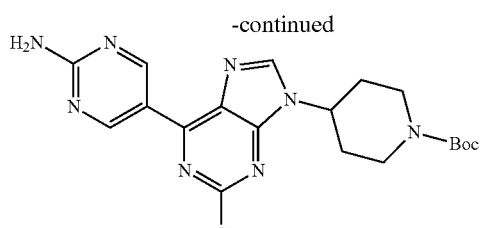

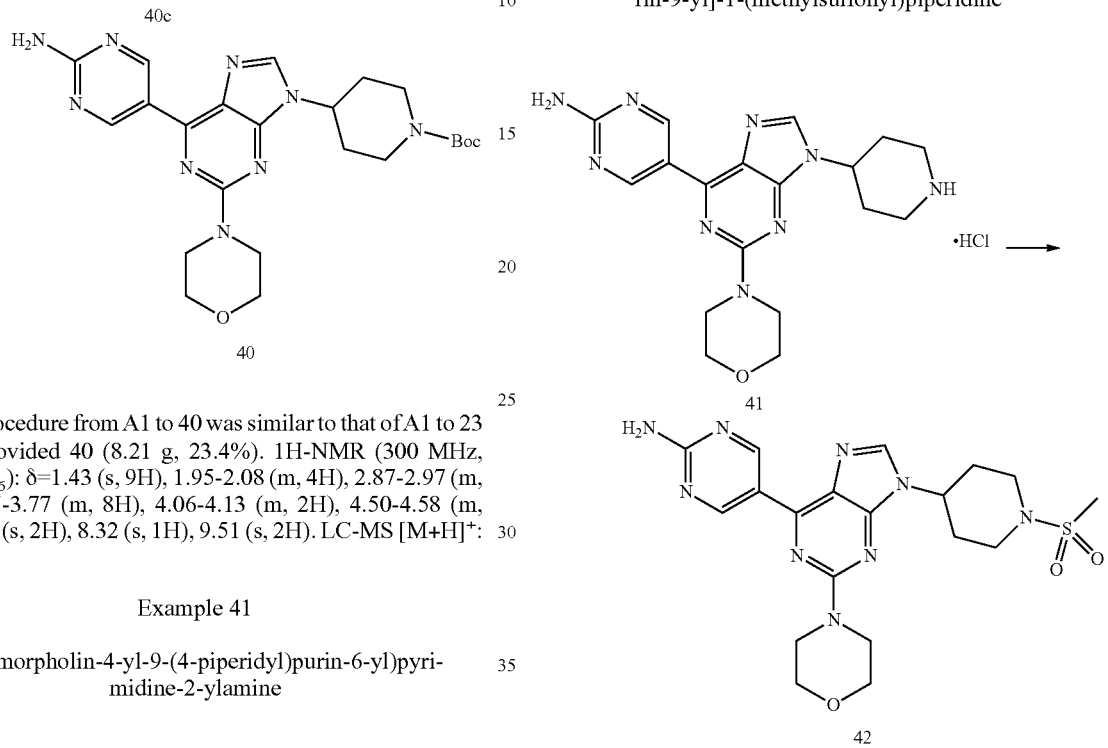

The procedure from A1 to 40 was similar to that of A1 to 23 which provided 40 (8.21 g, 23.4%). 1H-NMR (300 MHz, DMSO-d$_6$): δ=1.43 (s, 9H), 1.95-2.08 (m, 4H), 2.87-2.97 (m, 2H), 3.67-3.77 (m, 8H), 4.06-4.13 (m, 2H), 4.50-4.58 (m, 1H), 7.29 (s, 2H), 8.32 (s, 1H), 9.51 (s, 2H). LC-MS [M+H]$^+$: 482.2.

Example 41

5-(2-morpholin-4-yl-9-(4-piperidyl)purin-6-yl)pyrimidine-2-ylamine

The procedure from 40 to 41 was similar to that of 10d to 10e which provided 41 (8.66 g). 1H-NMR (300 MHz, DMSO-d$_6$): δ=2.16-2.20 (m, 2H), 2.43-2.55 (m, 2H), 3.04-3.16 (m, 2H), 3.41-3.46 (m, 2H), 3.72-3.84 (m, 8H), 4.64-4.71 (m, 1H), 8.26 (s, 1H), 9.04-9.22 (m, 2H), 9.58 (s, 2H). LC-MS [M+H]$^+$: 382.2.

Example 42

4-[6-(2-aminopyrimidin-5-yl)-2-morpholin-4-ylpurin-9-yl]-1-(methylsulfonyl)piperidine

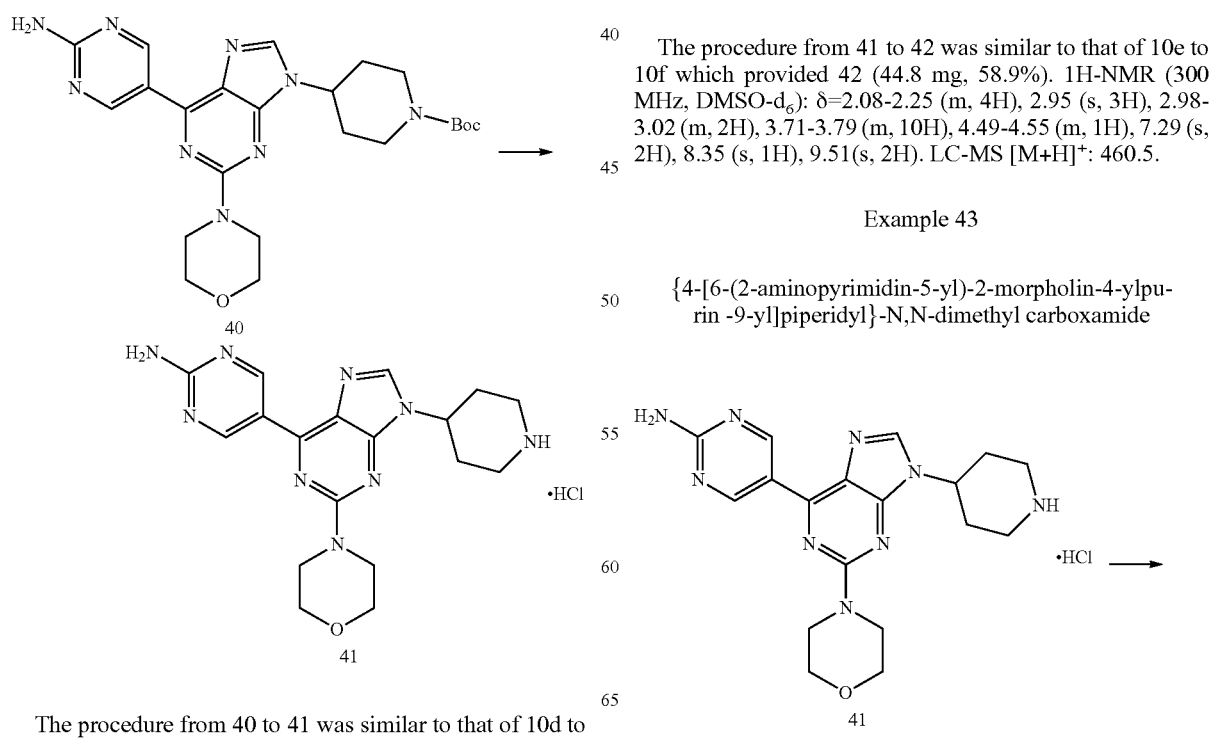

The procedure from 41 to 42 was similar to that of 10e to 10f which provided 42 (44.8 mg, 58.9%). 1H-NMR (300 MHz, DMSO-d$_6$): δ=2.08-2.25 (m, 4H), 2.95 (s, 3H), 2.98-3.02 (m, 2H), 3.71-3.79 (m, 10H), 4.49-4.55 (m, 1H), 7.29 (s, 2H), 8.35 (s, 1H), 9.51(s, 2H). LC-MS [M+H]$^+$: 460.5.

Example 43

{4-[6-(2-aminopyrimidin-5-yl)-2-morpholin-4-ylpurin-9-yl]piperidyl}-N,N-dimethyl carboxamide

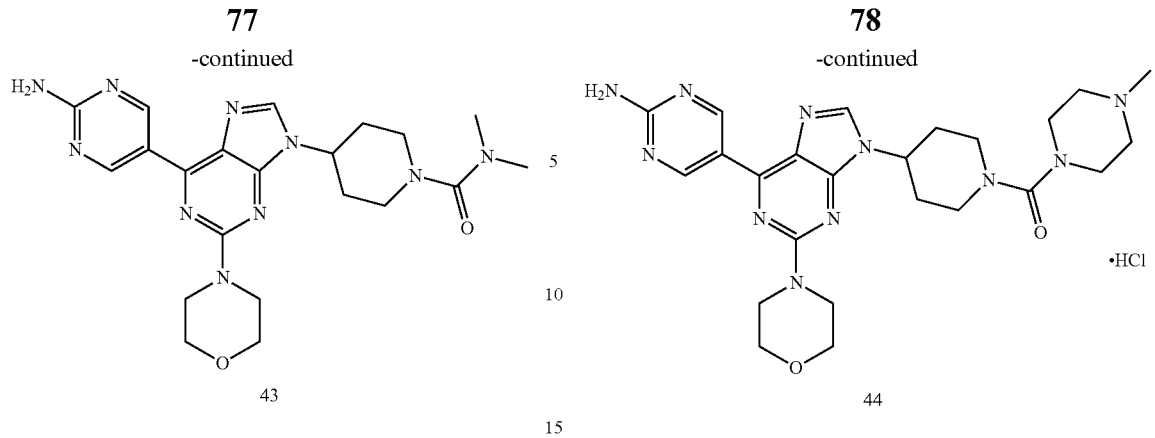

43

The procedure from 41 to 43 was similar to that of 11 to 13 which provided 43 (38.9 mg, 68.8%). 1H-NMR (300 MHz, DMSO-$d_6$): δ=1.98-2.03 (m, 4H), 2.72 (s, 6H), 2.86-2.94 (m, 2H), 3.69-3.78 (m, 10H), 4.48-4.56 (m, 1H), 7.29 (s, 2H), 8.32 (s, 1H), 9.51 (s, 2H). LC-MS [M+H]$^+$: 453.4.

Example 44

4-[6-(2-aminopyrimidin-5-yl)-2-morpholin-4-ylpurin-9-yl]piperidyl 4-methylpiperazinyl ketone

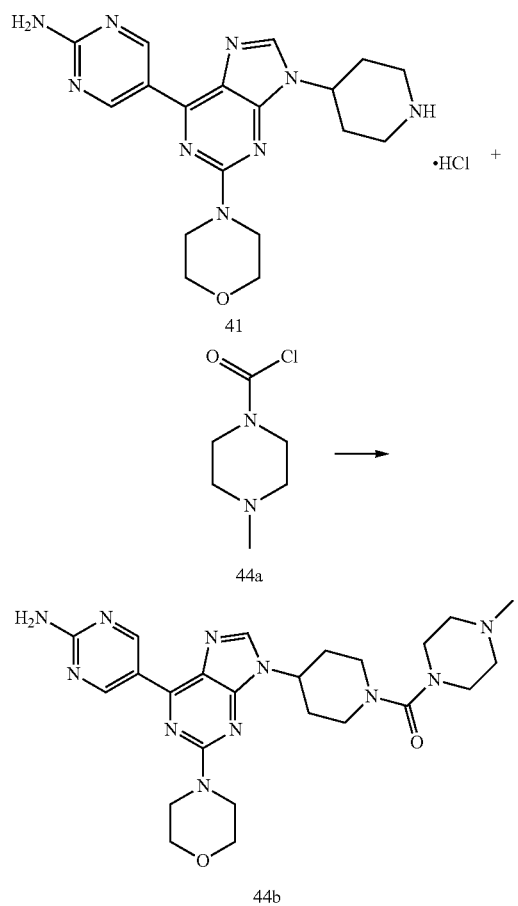

Step 1: The procedure from 41 to 44b was similar to that of 11 to 13 which provided 44b (990 mg, 82%).

Step 2: The procedure from 44b to 44 was similar to that of 33c to 33 which provided 44 (1.2 g). 1H-NMR (300 MHz, DMSO-$d_6$): δ=1.98-2.16 (m, 4H), 2.75 (d, 3H), 2.97-3.05 (m, 4H), 3.26-3.37 (m, 4H), 3.62-3.80 (m, 12H), 4.58-4.59 (m, 1H), 8.47 (s, 1H), 9.64 (s, 2H), 11.41 (brs, 1H). LC-MS [M+H]$^+$: 508.2.

Example 45

2-{4-[6-(2-aminopyrimidin-5-yl)-2-morpholin-4-ylpurin-9-yl]piperidyl}-N,N-dimethyl-2-oxoacetamide

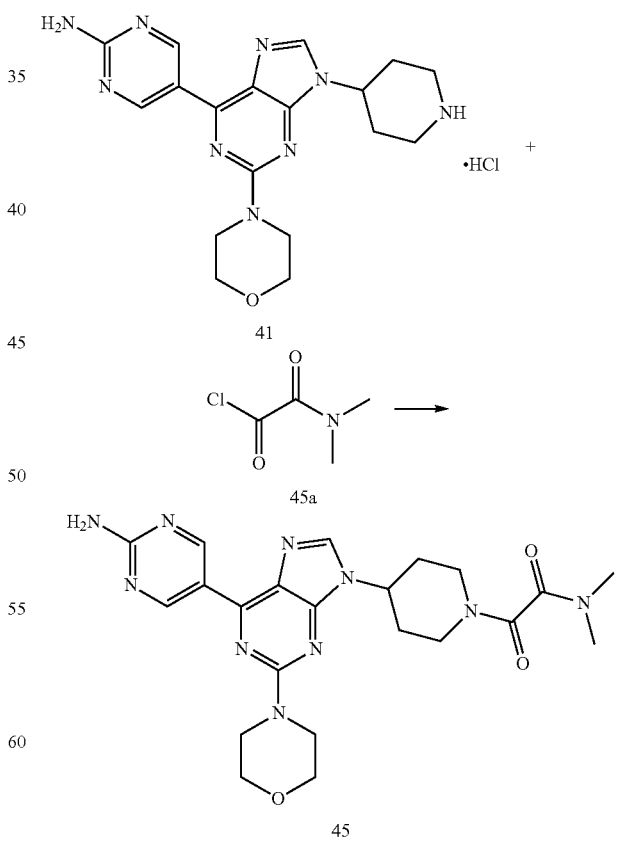

The procedure from 41 to 45 was similar to that of 11 to 13 which provided 45 (260 mg, 27%). 1H-NMR (300 MHz, CDCl₃): δ=2.18-2.27 (m, 4H), 2.86-2.96 (m, 4H), 3.05 (d, 3H), 3.27-3.36 (m, 2H), 3.82-3.88 (m, 8H), 4.58-4.65 (m, 1H), 4.78-4.83 (m, 1H), 5.36 (s, 2H), 7.80 (s, 1H), 9.62 (s, 2H). LC-MS [M+H]⁺: 481.2.

Example 46

2-{4-[6-(2-aminopyrimidin-5-yl)-2-morpholin-4-ylpurin-9-yl]piperidyl}ethan-1-ol

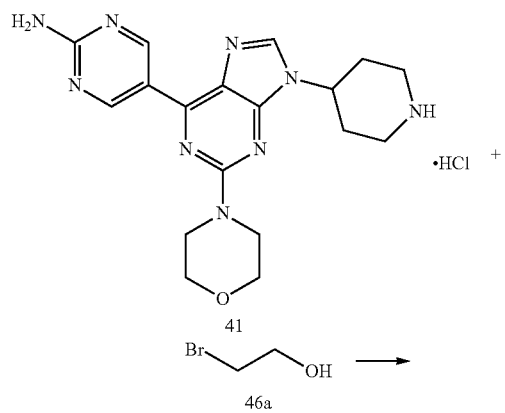

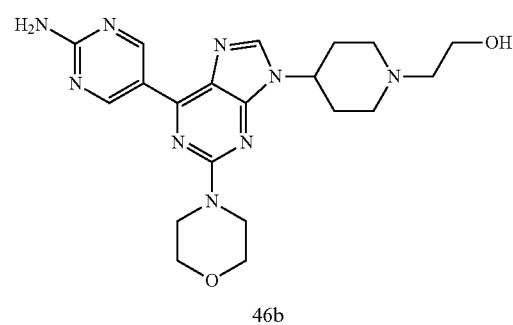

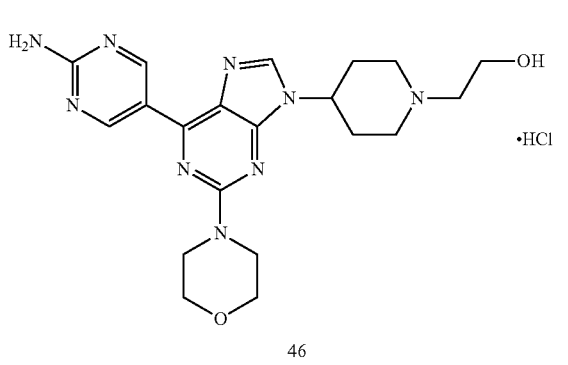

Step 1: The procedure from 41 to 46b was similar to that of A to 2a which provided 46b (170 mg, 71%).

Step 2: The procedure from 46b to 46 was similar to that of 33c to 33 which provided 46 (203 mg). 1H-NMR (300 MHz, DMSO-d₆): δ=2.22-2.27 (m, 2H), 2.64-2.76 (m, 2H), 3.19-3.29 (m, 3H), 3.43-3.45 (m, 1H), 3.71-3.89 (m, 14H), 8.28 (s, 1H), 9.61 (s, 2H), 10.75 (brs, 1H). LC-MS [M+H]⁺: 426.2.

Example 47

2-{4-[6-(2-aminopyrimidin-5-yl)-2-morpholin-4-ylpurin-9-yl]piperidyl}-1-(methylsulfonyl)ethane

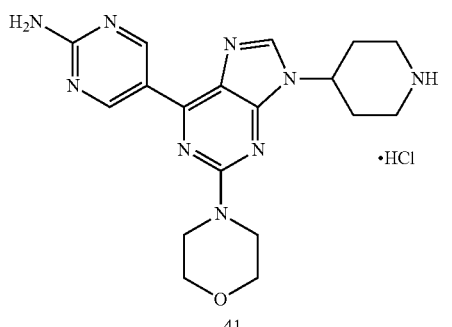

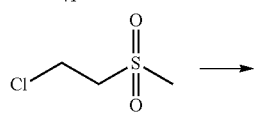

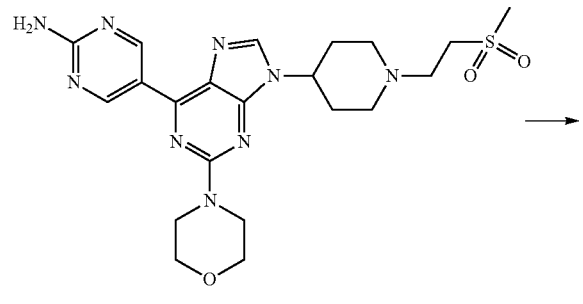

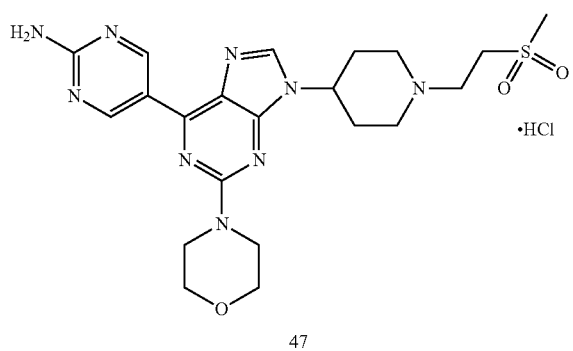

Step 1: The procedure from 41 to 47b was similar to that of A to 2a which provided 47b (227 mg, 57%).

Step 2: The procedure from 47b to 46 was similar to that of 33c to 33 which provided 47 (250 mg). 1H-NMR (300 MHz, DMSO-d₆): δ=2.25-2.28 (m, 2H), 2.64-2.76 (m, 2H), 3.14 (s, 3H), 3.16-3.25 (m, 2H), 3.46-3.57 (m, 2H), 3.69-3.85 (m, 12H), 4.59-4.67 (m, 1H), 8.25 (s, 1H), 9.56 (s, 2H), 11.47 (brs, 1H). LC-MS [M+H]⁺: 488.2.

Example 48

5-{9-[1-(2-methoxyethyl)(4-piperidyl)]-2-morpholin-4-ylpurin-6-yl}pyrimidine-2-ylamine

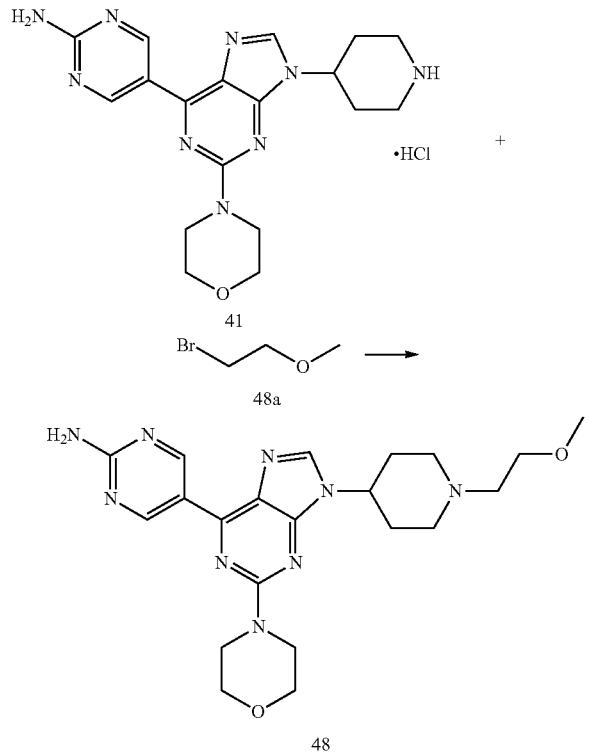

The procedure from 41 to 48 was similar to that of A to 2a which provided 48 (57 mg, 16%). 1H-NMR (300 MHz, CDCl₃): δ=2.12-2.26 (m, 6H), 2.66 (t, 2H), 3.14-3.17 (m, 2H), 3.38 (s, 3H), 3.55 (t, 2H), 3.81-3.91 (m, 8H), 4.37-4.44 (m, 1H), 5.37 (s, 2H), 7.85 (s, 1H), 9.62 (s, 2H). LC-MS [M+H]⁺: 440.2.

Example 49

5-[9-(1-cyclopentyl(4-piperidyl))-2-morpholin-4-ylpurin-6-yl]pyrimidine-2-ylamine

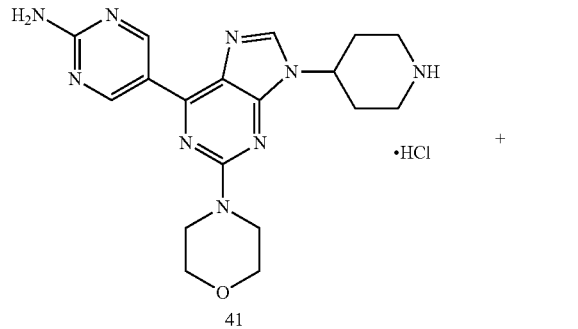

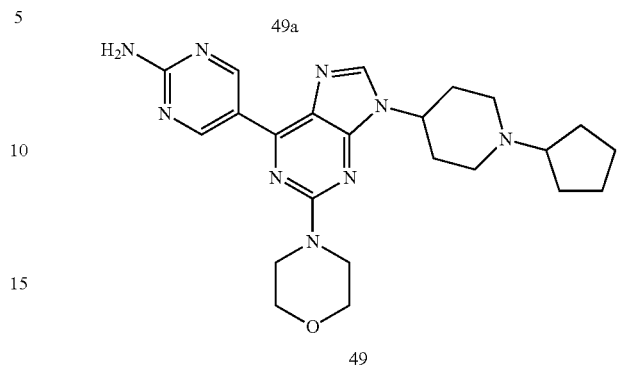

The procedure from 41 to 49 was similar to that of A to 2a which provided 49 (22 mg, 30%). 1H-NMR (300 MHz, DMSO-d₆): δ=1.58-1.74 (m, 6H), 1.99-2.10 (m, 2H), 2.35-2.37 (m, 4H), 3.17-3.27 (m, 2H), 3.54-3.82 (m, 12H), 4.65-4.70 (m, 1H), 7.31 (s, 2H), 8.23 (s, 1H), 9.52 (s, 2H). LC-MS [M+H]⁺: 450.2.

Example 50

5-{2-morpholin-4-yl-9-[1-(2,2,2-trifluoroethyl)(4-piperdyl)]purin-6-yl}pyrimidine-2-ylamine

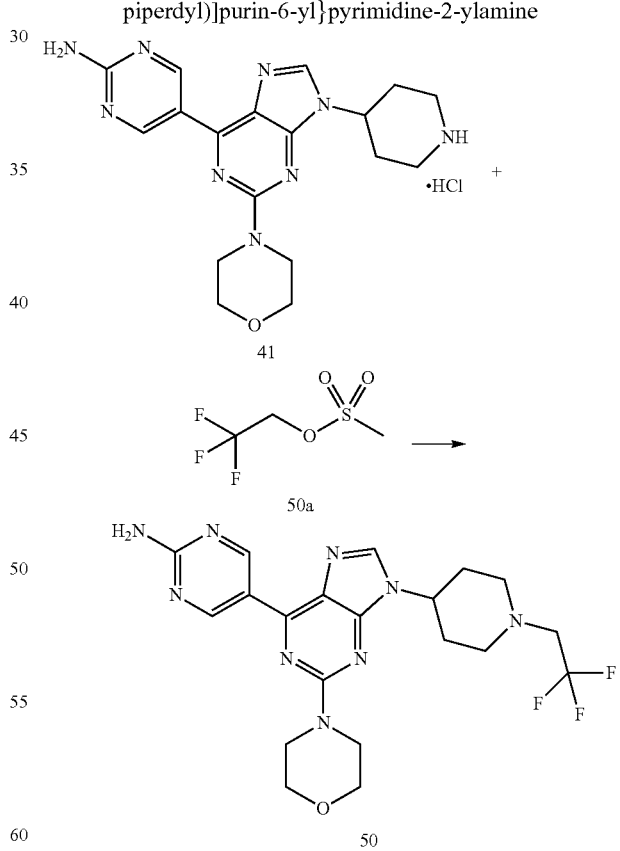

A mixture of 41 (70 mg, 0.14 mmol), 50a (38 mg, 0.21 mmol) and K₂CO₃ (158 mg, 1.14 mmol) in DMF (15 mL) was heated under microwave condition at 150° C. for 1 h. The solid was filtered off and the filtrate was evaporated under vacuum. The residue was purified by prep-HPLC to give 50 (1.5 mg, 2.3%).

Example 51

5-{2-morpholin-4-yl-9-[1-(3-pyridylmethyl) (4-piperidyl)]purin-6-yl}pyrimidine-2-ylamine

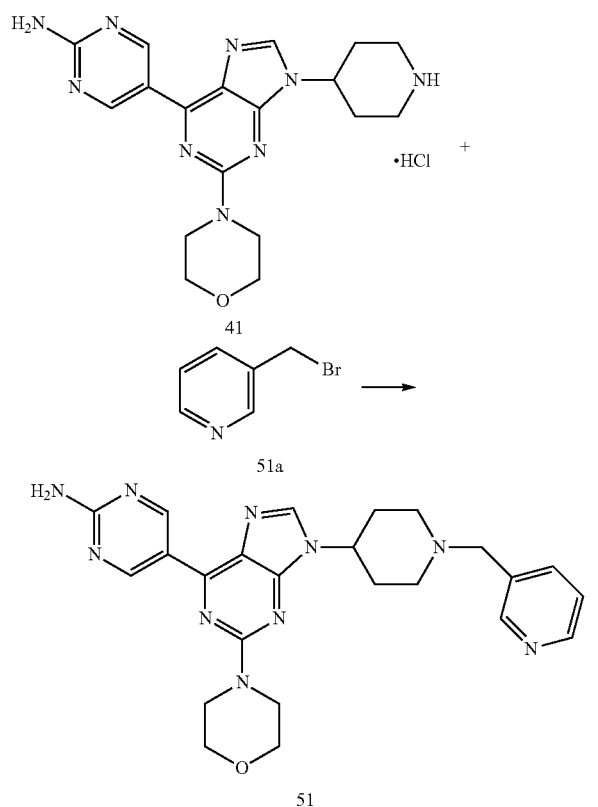

The procedure from 41 to 51 was similar to that of A to 2a which provided 51 (14 mg, 21%). 1H-NMR (300 MHz, DMSO-d$_6$): δ=1.99-2.23 (m, 6H), 2.89-2.99 (m, 2H), 3.59 (s, 2H), 3.65-3.76 (m, 8H), 4.31-4.35 (m, 1H), 7.29 (s, 2H), 7.36-7.40 (m, 1H), 7.74 (d, 1H), 8.34 (s, 1H), 8.48-8.53 (m, 2H), 9.51 (s, 2H). LC-MS [M+H]$^+$: 473.2.

Example 52

1-{4-[6-(2-aminopyrimidin-5-yl)-2-morpholin-4-ylpurin-9-yl]piperidyl}-2-hydroxyethan-1-one

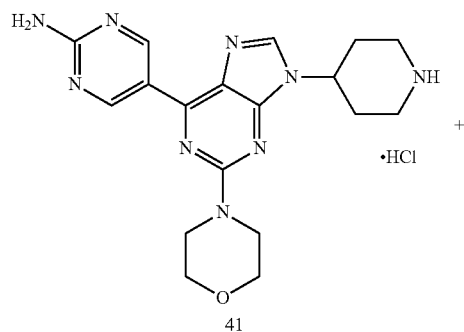

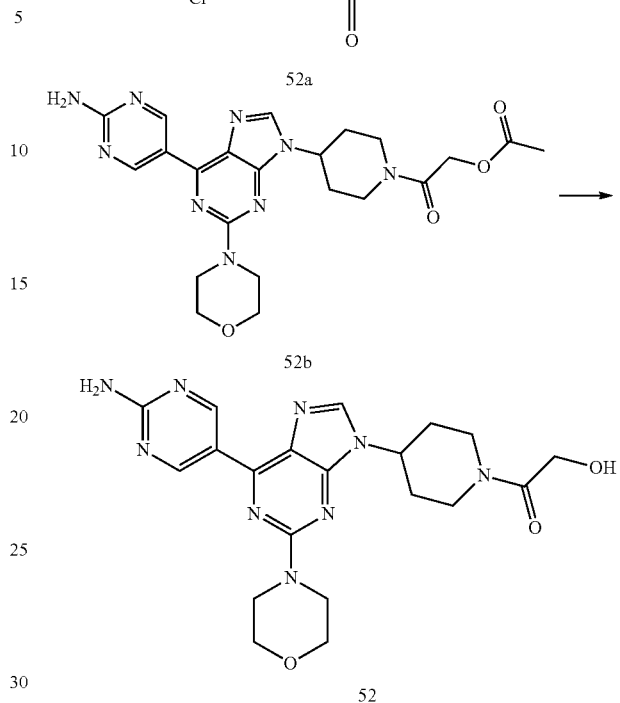

Step 1: The procedure from 41 to 52b was similar to that of 11 to 13 which provided 52b (36 mg, 54%).

Step 2: The procedure from 52b to 52 was similar to that of 7c to 7d which provided 52 (32 mg, 97%). 1H-NMR (300 MHz, DMSO-d$_6$): δ=1.96-2.03 (m, 4H), 2.77-2.86 (m, 1H), 3.14-3.18 (m, 1H), 3.71-3.78 (m, 10H), 4.14-4.16 (m, 2H), 4.57-4.65 (m, 3H), 7.29 (s, 2H), 8.30 (s, 1H), 9.51 (s, 2H). LC-MS [M+H]$^+$: 440.1.

Example 53

5-[9-(1-ethyl(4-piperidyl))-2-morpholin-4-ylpurin-6-yl]pyrimidine-2-ylamine

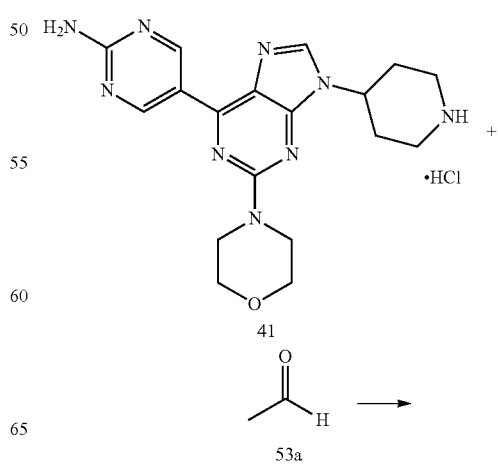

-continued

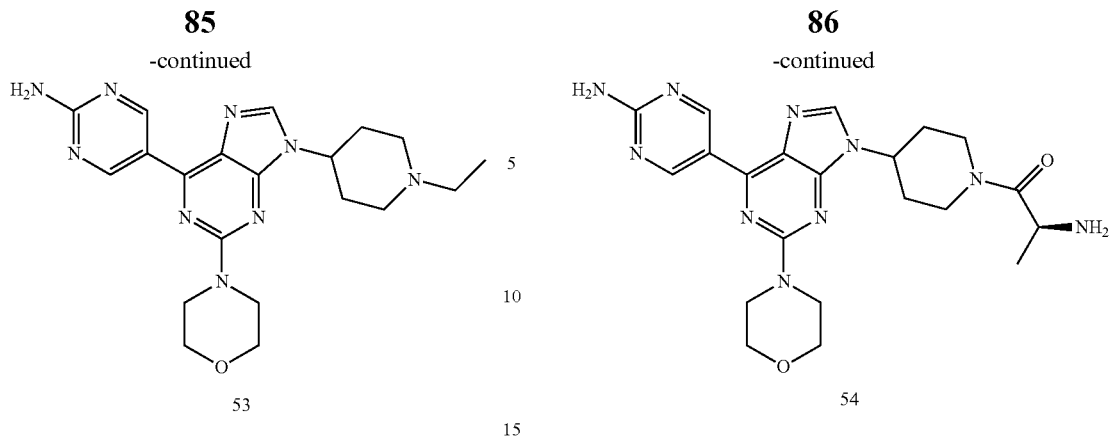

53

54

To a suspension of 41 (80 mg, 0.16 mmol), aq. acetaldehyde (40%, 36 mg, 0.33 mmol)) and Et₃N (82 mg, 0.81 mmol) was added NaBH(OAc)₃ (345 mg, 1.63 mmol) in portions at r.t. The resulting mixture was stirred at r.t. for 5 hours and evaporated to dryness. The residue was purified by column chromatography (EA:methanol=10:3) to provide 53 (43 mg, 64%). 1H-NMR (300 MHz, CD₃OD): δ=1.34 (t, 3H), 2.32-2.36 (m, 2H), 2.58-2.63 (m, 2H), 3.00-3.22 (m, 4H), 3.61-3.66 (m, 2H), 3.78-3.91 (m, 8H), 4.60-4.70 (m, 1H)□8.08 (s, 1H), 9.50 (s, 2H). LC-MS [M+H]⁺: 410.2.

Step 1: The procedure from 41 to 54b was similar to that of 7d to 7e which provided 54b (315 mg, 76%).

Step 2: The procedure from 54b to 54 was similar to that of 36c to 36 which provided 54 (217 mg, 84%). 1H-NMR (300 MHz, DMSO-d₆): δ=1.09-1.13 (t, 3H), 1.64 (s, 2H), 1.93-2.07 (m, 4H), 2.69-2.78 (m, 1H), 3.16-3.31 (m, 2H), 3.65-3.84 (m, 8H), 4.09-4.15 (m, 1H), 4.58-4.65 (m, 2H), 7.29 (s, 2H), 8.30 (s, 1H), 9.51 (s, 2H). LC-MS [M+H]⁺: 453.2.

Example 54

(2S)-2-amino-1-{4-[6-(2-aminopyrimidin-5-yl)-2-morpholin-4-ylpurin-9-yl]piperidyl}propan-1-one Example 55

(2S)-1-{4-[6-(2-aminopyrimidin-5-yl)-2-morpholin-4-ylpurin-9-yl]piperidyl}-2-hydroxypropan-1-one

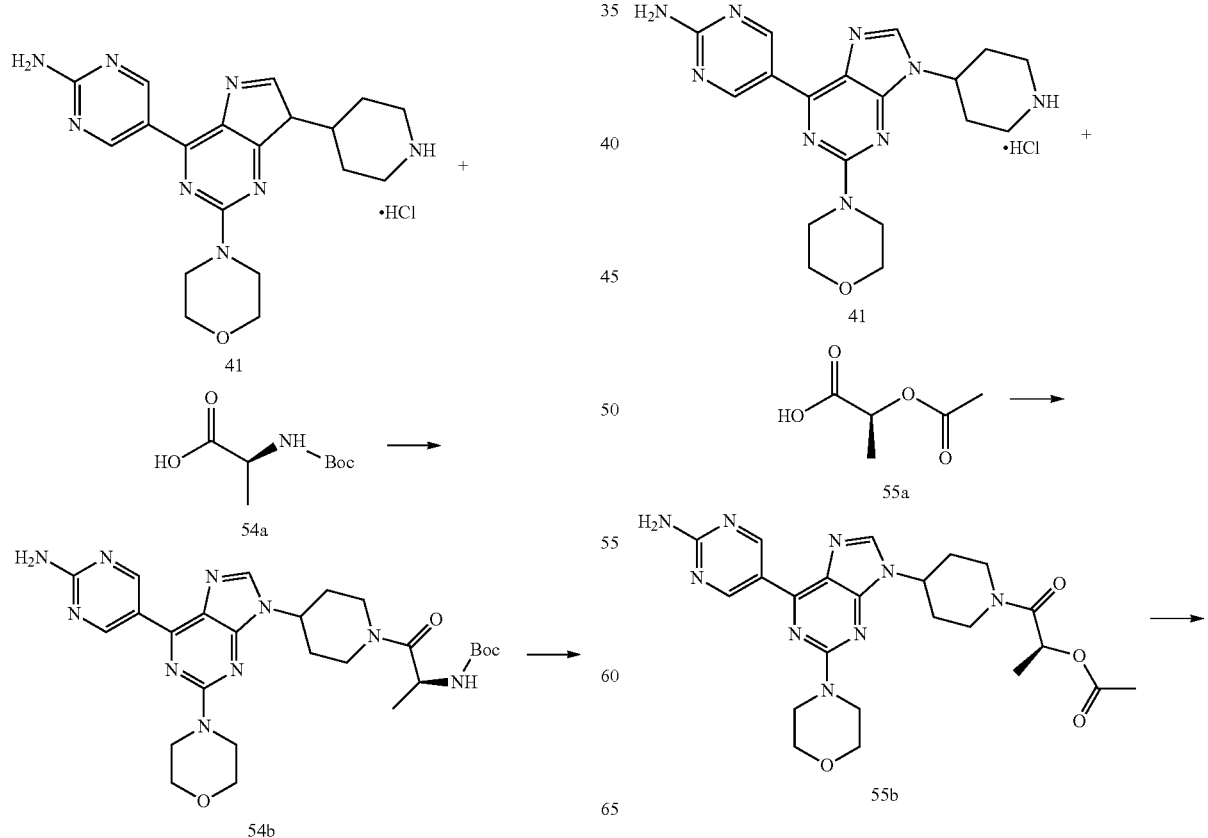

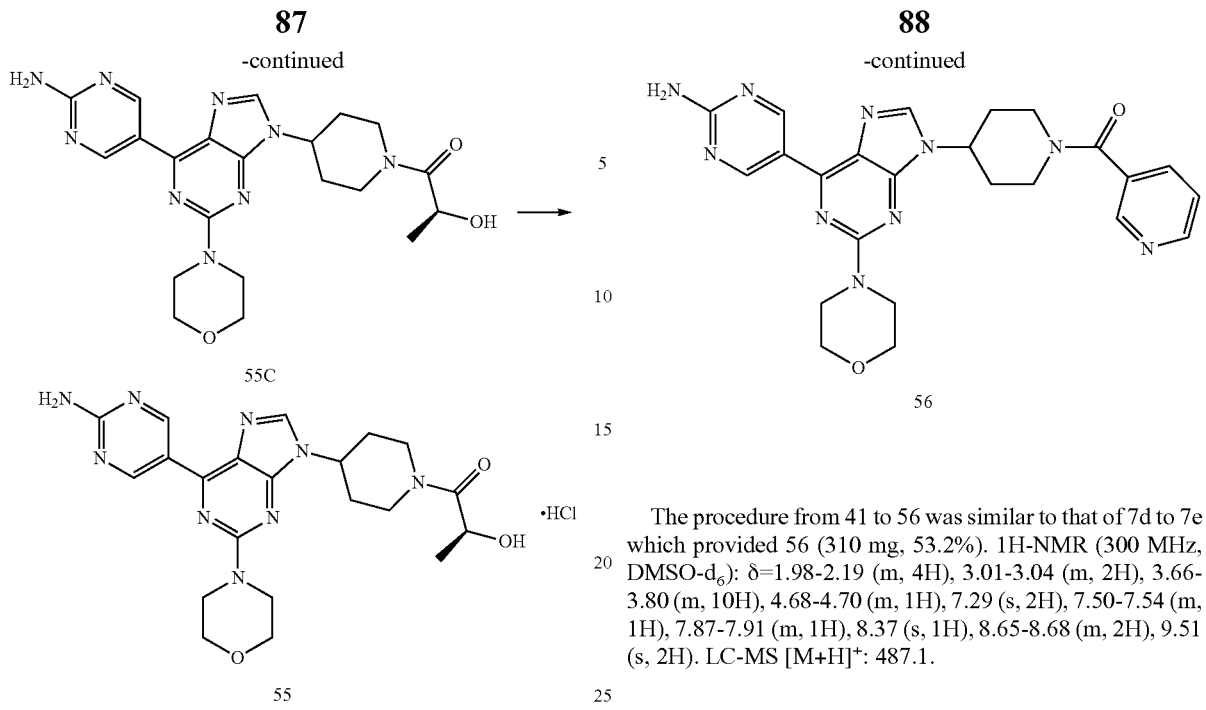

Step 1: The procedure from 41 to 55b was similar to that of 7d to 7e which provided crude 55b.

Step 2: The procedure from 55b to 55c was similar to that of 29d to 29 which provided crude 55c.

Step 3: The procedure from 55c to 55 was similar to that of 33c to 33 which provided 55 (322 mg, 66.5%). 1H-NMR (300 MHz, DMSO-$d_6$): δ=1.22 (t, 3H), 1.97-2.07 (m, 4H), 2.75-2.83 (m, 1H), 3.16-3.24 (m, 1H), 3.71-3.80 (m, 8H), 4.16-4.20 (m, 1H), 4.46-4.70 (m, 3H), 8.44 (s, 1H), 9.62 (s, 2H). LC-MS [M+H]$^+$: 454.2.

Example 56

4-[6-(2-aminopyrimidin-5-yl)-2-morpholin-4-ylpurin-9-yl]piperidyl 3-pyridyl ketone

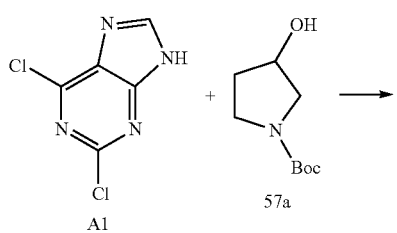

The procedure from 41 to 56 was similar to that of 7d to 7e which provided 56 (310 mg, 53.2%). 1H-NMR (300 MHz, DMSO-$d_6$): δ=1.98-2.19 (m, 4H), 3.01-3.04 (m, 2H), 3.66-3.80 (m, 10H), 4.68-4.70 (m, 1H), 7.29 (s, 2H), 7.50-7.54 (m, 1H), 7.87-7.91 (m, 1H), 8.37 (s, 1H), 8.65-8.68 (m, 2H), 9.51 (s, 2H). LC-MS [M+H]$^+$: 487.1.

Example 57

5-[9-(1-ethylpyrrolidin-3-yl)-2-morpholin-4-ylpurin-6-yl]pyrimidine-2-ylamine

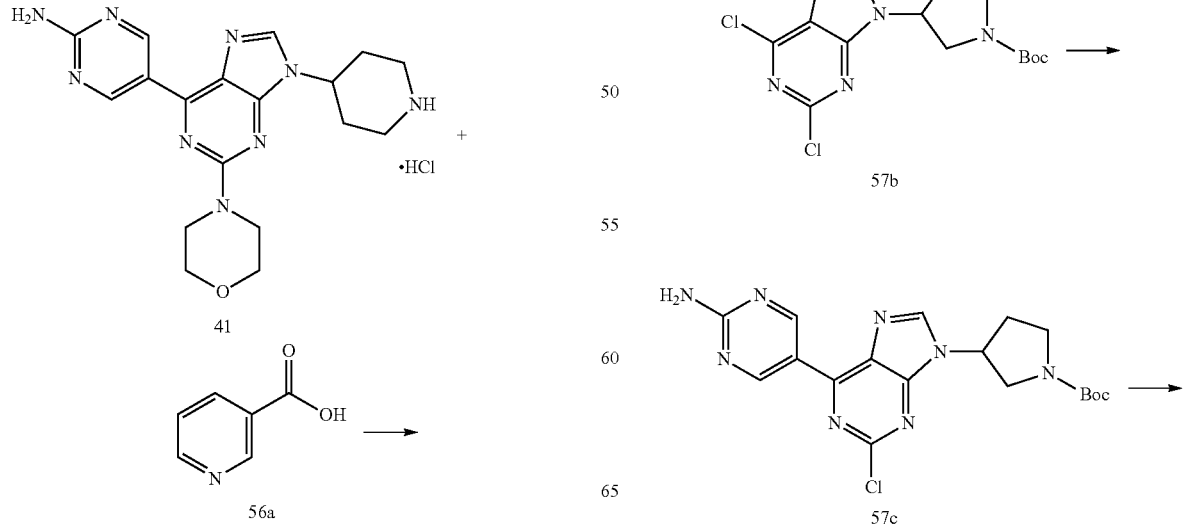

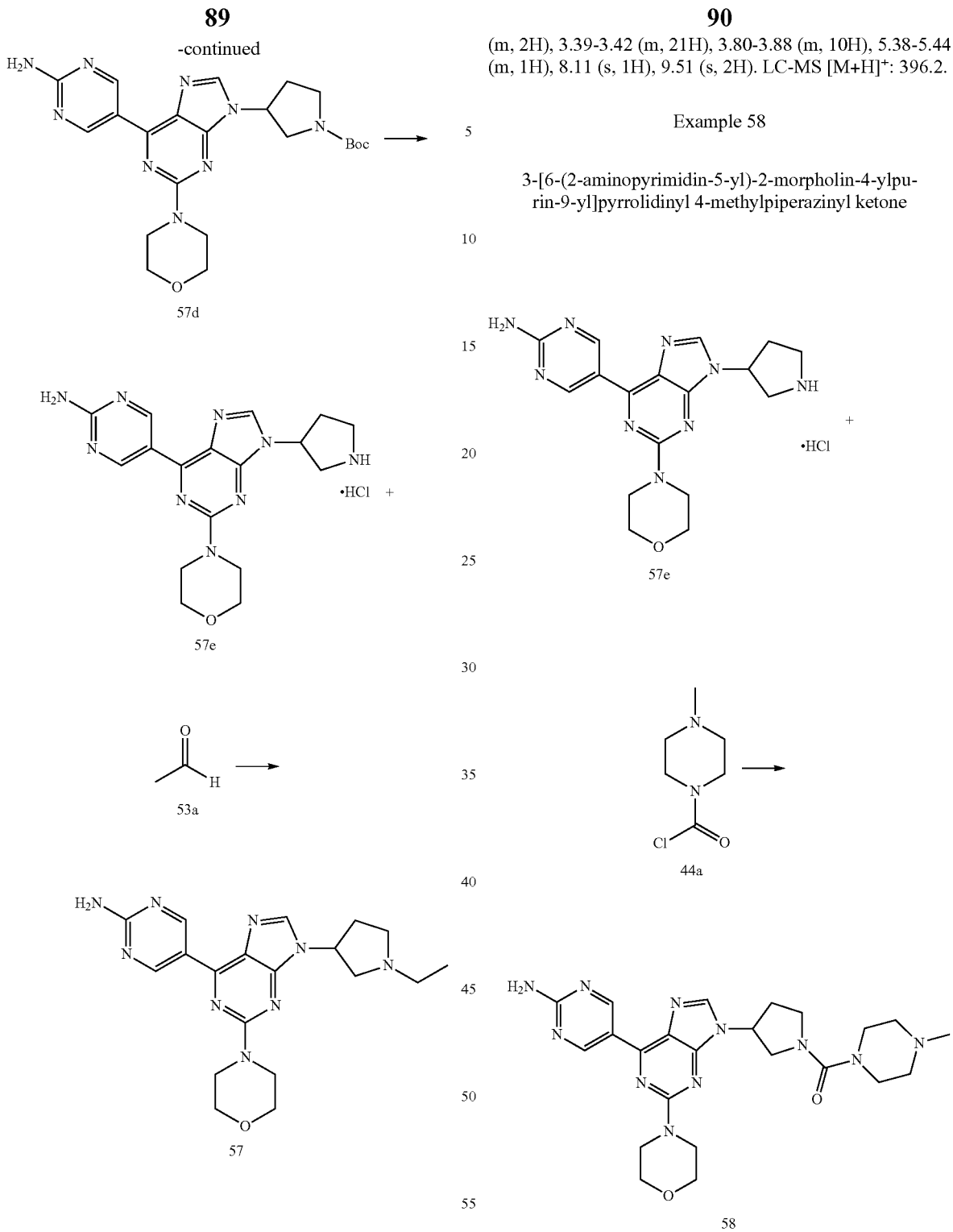

(m, 2H), 3.39-3.42 (m, 21H), 3.80-3.88 (m, 10H), 5.38-5.44 (m, 1H), 8.11 (s, 1H), 9.51 (s, 2H). LC-MS [M+H]⁺: 396.2.

Example 58

3-[6-(2-aminopyrimidin-5-yl)-2-morpholin-4-ylpurin-9-yl]pyrrolidinyl 4-methylpiperazinyl ketone Step 1: The procedure from A1 to 57d was similar to that of A1 to 23 which provided 57d (355 mg, 42.6%).

Step 2: The procedure from 57d to 57e was similar to that of 10d to 10e which provided 57e (472 mg).

Step 3: The procedure from 57e to 57 was similar to that of 41 to 53 which provided 57 (26 mg, 31.3%). 1H-NMR (300 MHz, CD$_3$OD): δ=1.28-1.32 (m, 2H), 1.41 (t, 3H), 2.69-2.74

The procedure from 57e to 58 was similar to that of 11 to 13 which provided 58 (482 mg, 97.8%). 1H-NMR (300 MHz, DMSO-d$_6$): δ=2.39-2.43 (m, 2H), 2.74 (s, 3H), 2.94-3.24 (m, 4H), 3.53-3.90 (m, 16H), 5.08 (m, 1H), 7.30 (s, 2H), 8.22 (s, 1H), 9.51 (s, 2H), 10.50 (brs, 1H). LC-MS [M+H]$^+$: 494.2.

3H), 3.51-4.06 (m, 14H), 5.04-5.20 (m, 1H), 7.30 (s, 2H), 8.21-8.26 (m, 1H), 9.51 (s, 1H). LC-MS [M+H]$^+$: 439.2.

Example 59

(2R)-2-amino-1-{3-[6-(2-aminopyrimidin-5-yl)-2-morpholin-4-ylpurin-9-yl]pyrrolidinyl}propan-1-one Example 60

(2R)-1-{3-[6-(2-aminopyrimidin-5-yl)-2-morpholin-4-ylpurin-9-yl]pyrrolidinyl}-2-hydroxypropan-1-one

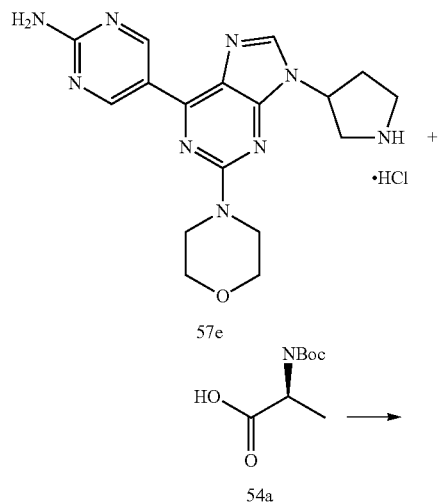
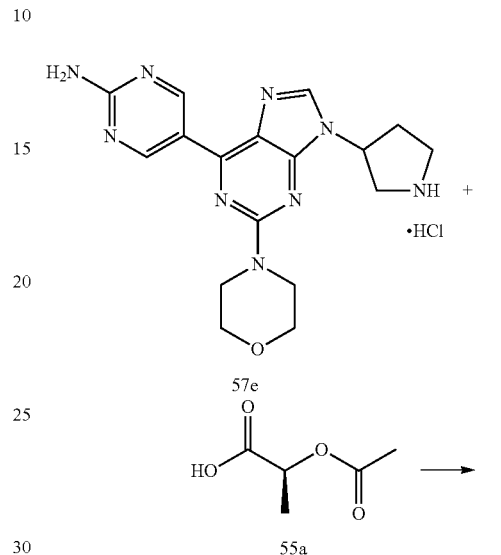
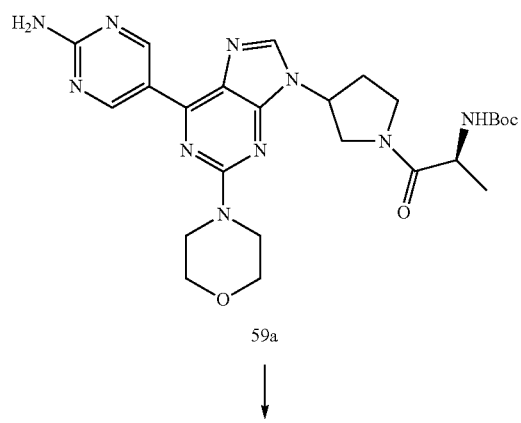
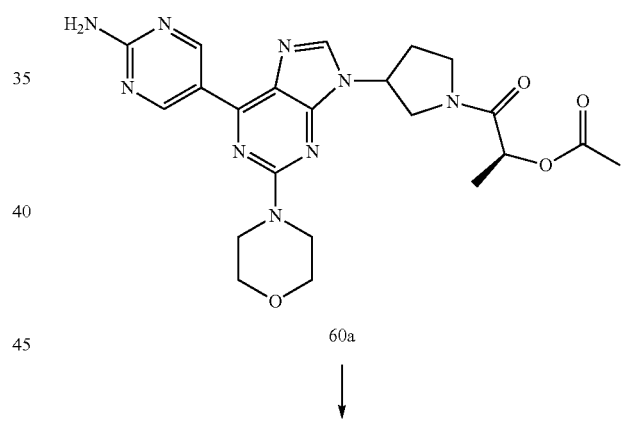
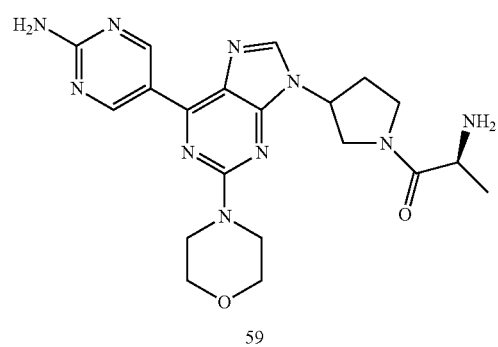
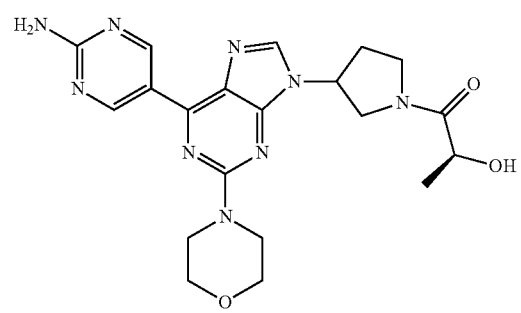

The procedure from 57e to 59 was similar to that of 41 to 54 which provided 59 (21 mg, 43.5%). 1H-NMR (300 MHz, DMSO-d$_6$): δ=1.03 (d, 1H), 1.05-1.13 (m, 2H), 2.38-2.51 (m, The procedure from 57e to 60 was similar to that of 41 to 55c which provided 60 (19 mg, 50.4%). 1H-NMR (300 MHz, DMSO-d$_6$): δ=1.15-1.23 (m, 3H), 2.39-2.46 (m, 1H), 3.51-

4.07 (m, 14H), 4.93-5.15 (m, 2H), 7.30 (s, 2H), 8.22 (d, 1H), 9.51 (s, 2H). LC-MS [M+H]+: 440.2.

Example 61

5-[2-morpholin-4-yl-9-(4-piperidylmethyl)purin-6-yl]pyrimidine-2-ylamine

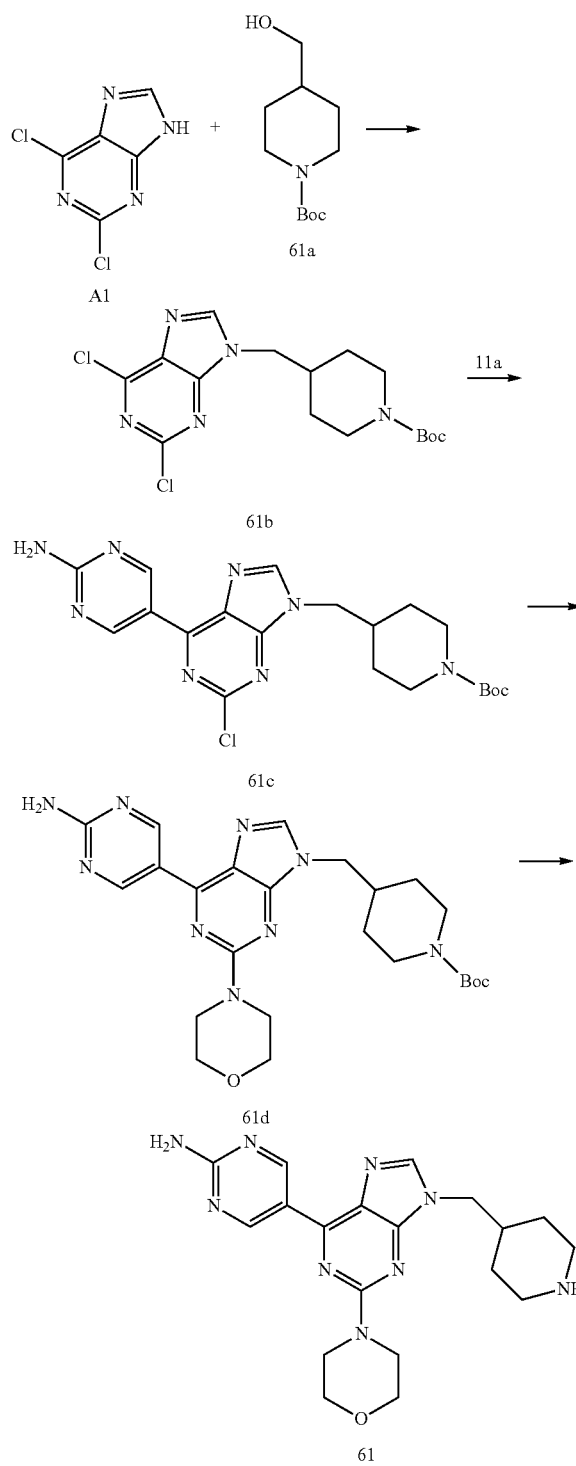

Step 1: The procedure from A1 to 61d was similar to that of A1 to 10b to 11c which provided 61d (526 mg, 33.1%).

Step 2: The procedure from 61d to 61 was similar to that of 36c to 36 which provided 61 (405 mg, 96.5%). 1H-NMR (300 MHz, DMSO-$d_6$): δ=1.03-1.16 (m, 2H), 1.23 (s, 1H), 1.42-1.46 (m, 2H), 1.93-2.01 (m, 1H), 2.36-2.43 (m, 2H), 2.89-2.93 (m, 2H), 3.71-3.78 (m, 8H), 3.99 (d, 2H), 7.28 (s, 2H), 8.20 (s, 1H), 9.51 (s, 2H). LC-MS [M+H]+: 396.2.

Example 62

{2-[6-(2-aminopyrimidin-5-yl)-2-morpholin-4-ylpurin-9-yl]ethyl}(methylsulfonyl)amine

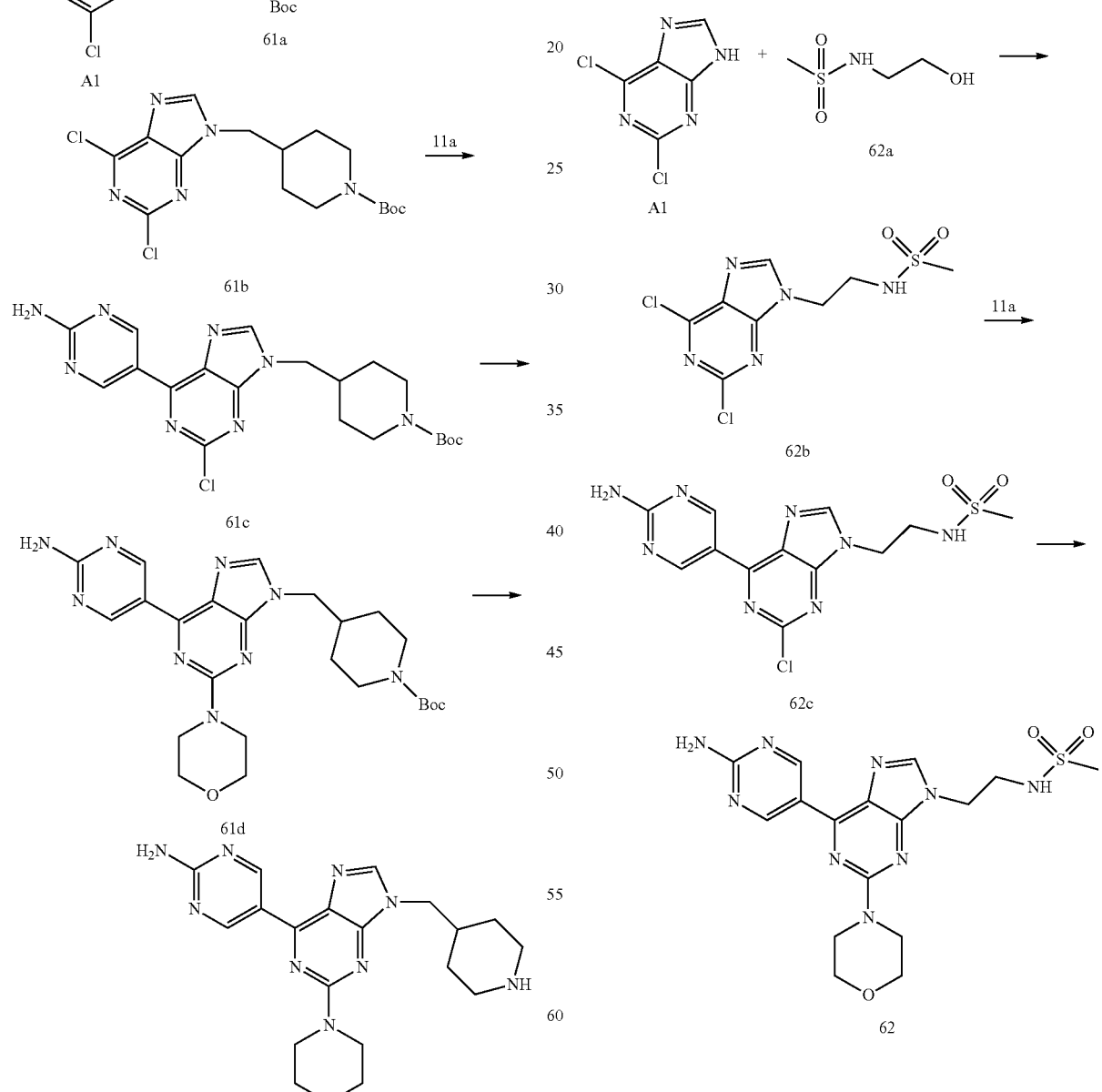

The procedure from A1 to 62 was similar to that of A1 to 10b to 11c which provided 62 (50 mg, 5.9%). 1H-NMR (300 MHz, DMSO-$d_6$): δ=2.87 (s, 3H), 3.40-3.46 (m, 2H), 3.71-

3.79 (m, 8H), 4.23 (t, 2H), 7.24-7.30 (m, 3H), 8.17 (s, 1H), 9.52 (s, 2H). LC-MS [M+H]+: 420.1.

Example 63

{2-[6-(2-aminopyrimidin-5-yl)-2-morpholin-4-ylpurin-9-yl]ethyl}methyl(methylsulfonyl)amine

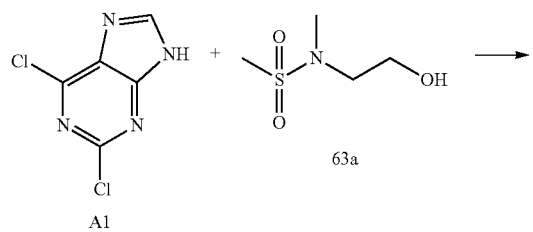

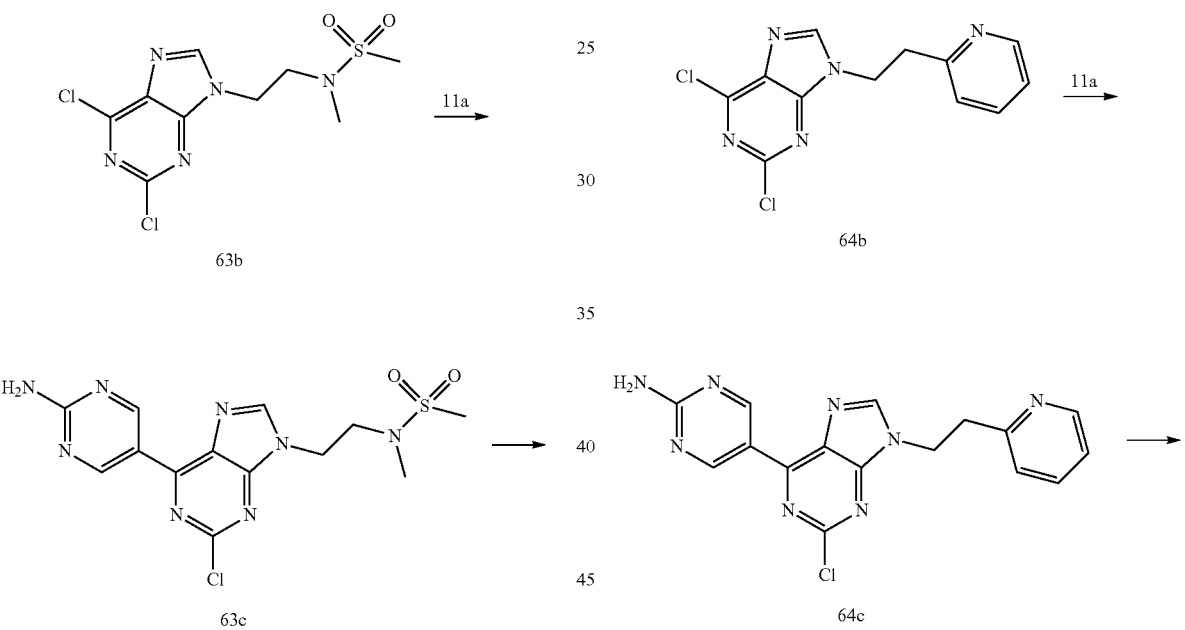

The procedure from A1 to 63 was similar to that of A1 to 10b to 11c which provided 63 (70 mg, 13.1%). 1H-NMR (300

MHz, DMSO-$d_6$): δ=2.80 (d, 6H), 3.51 (t, 2H), 3.71-3.80 (m, 8H), 4.32 (t, 2H), 7.28 (s, 2H), 8.19 (s, 1H), 9.51 (s, 2H). LC-MS [M+H]+: 434.1.

Example 64

5-[2-morpholin-4-yl-9-(2-(2-pyridyl)ethyl) purin-6-yl]pyrimidine-2-ylamine

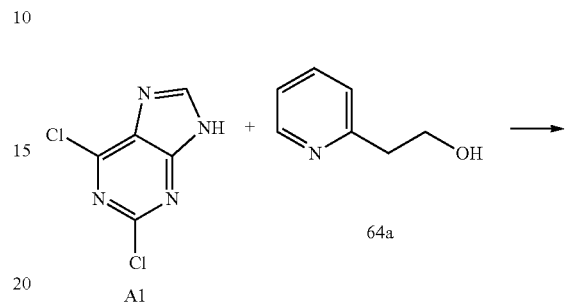

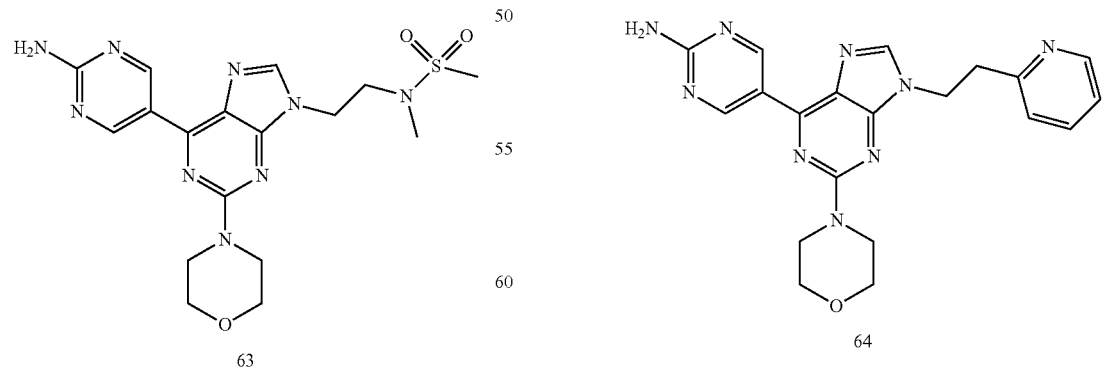

The procedure from A1 to 64 was similar to that of A1 to 10b to 11c which provided 64 (221 mg, 18.2%). 1H-NMR (300 MHz, DMSO-$d_6$): δ=3.30-3.40 (m, 2H), 3.72-3.74 (m, 8H), 4.51 (t, 2H), 7.19-7.26 (m, 4H), 7.66 (t, 1H), 8.04 (s, 1H), 8.48-8.49 (d, 1H), 9.48 (s, 2H). LC-MS [M+H]+: 404.2.
Example 65
Synthesis of 5-[2-morpholin-4-yl-9-(2-(3-pyridyl)ethyl)purin-6-yl]pyrimidine-2-ylamine
2H), 7.24-7.28 (m, 3H), 7.55-7.59 (m, 1H), 8.07 (s, 1H), 8.33 (d, 1H), 8.38 (d, 1H), 9.49 (s, 2H). LC-MS [M+H]+: 404.1.
Example 66
4-[6-(3-hydroxyphenyl)-2-morpholin-4-ylpurin-9-yl]piperidyl-4-methylpiperazinyl ketone
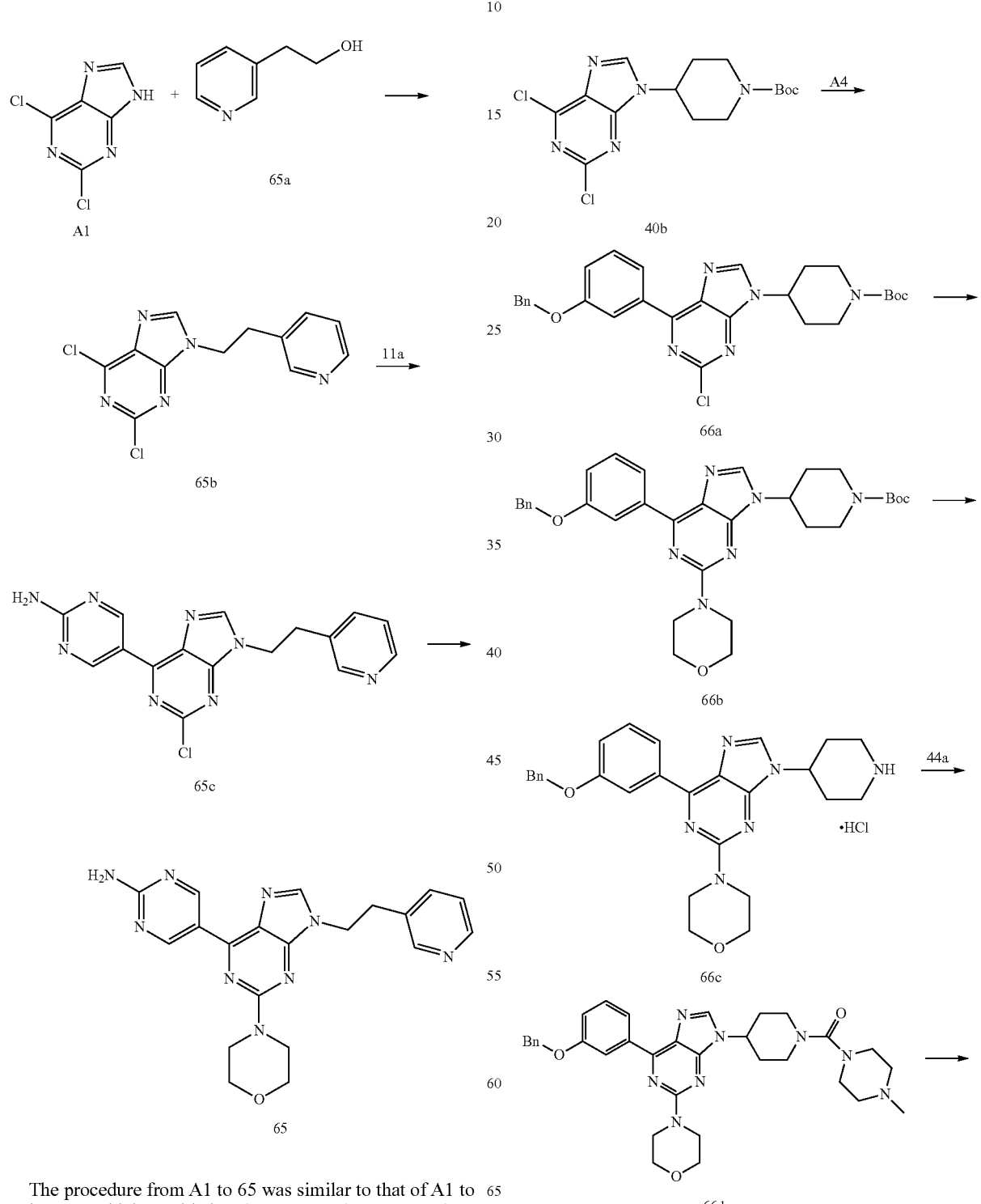
The procedure from A1 to 65 was similar to that of A1 to 10b to 11c which provided 65 (30 mg, 2.5%). 1H-NMR (300 MHz, DMSO-d$_6$): δ=3.18 (t, 2H), 3.70-3.74 (m, 8H), 4.41 (t,

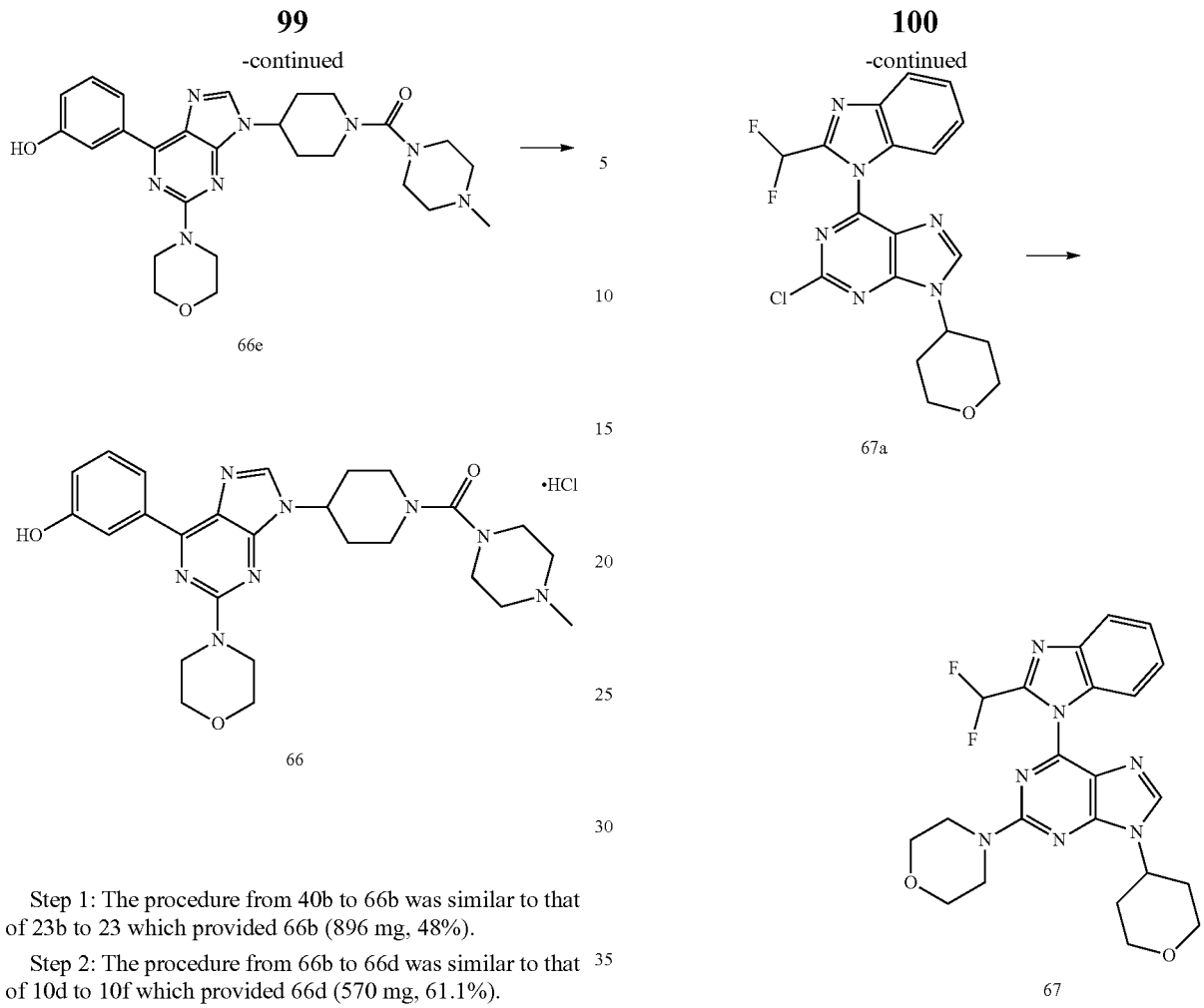

Step 1: The procedure from 40b to 66b was similar to that of 23b to 23 which provided 66b (896 mg, 48%).

Step 2: The procedure from 66b to 66d was similar to that of 10d to 10f which provided 66d (570 mg, 61.1%).

Step 3: The procedure from 66d to 66e was similar to that of A to 1 which provided 66e (304 mg, 62.8%).

Step 5: The procedure from 66e to 66 was similar to that of 33c to 33 which provided 66 (346 mg). 1H-NMR (300 MHz, DMSO-$d_6$): δ=2.00-2.18 (m, 4H), 2.77 (d, 3H), 2.98-3.06 (m, 4H), 3.20-3.45 (m, 4H), 3.64-3.81 (m, 12H), 4.57-4.64 (m, 1H), 6.91-6.94 (m, 1H), 7.33 (t, 1H), 8.19-8.24 (m, 2H), 8.38 (s, 1H), 10.83(brs, 1H). LC-MS [M+H]$^+$: 507.3.

Example 67

6-(2-Difluoromethyl-benzoimidazol-1-yl)-2-morpholin-4-yl-9-(tetrahydro-pyran-4-yl)-9H-purine

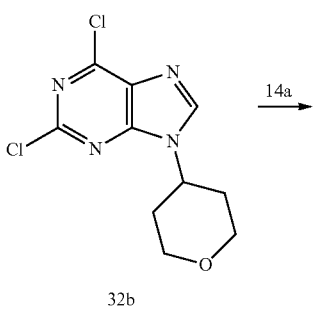

To a solution of 14a (247 mg, 1.47 mmol, 1 eq) in DMF (4 mL) was added NaH (60%, 70 mg, 1.76 mmol, 1,1.2 eq) portion-wise at 0~5° C. The resulting mixture was stirred for 30 min at r.t. Then 32b (400 mg, 1.47 mmol, 1 eq) was added to the mixture portion-wise. The reaction mixture was stirred at r.t. overnight. The solvent was removed and the residue was purified by column chromatography (PE:EA=4:1) to give 67a (360 mg, yield: 61%) as off-white solid.

HNMR (CDCl$_3$, 300 MHz):8.28(s,1H),8.01(s,1H),7.96~7.84(m, 2H),7.70~7.63(m,2H),4.88 (m,1H),4.24~4.20(m,2H), 3.71~3.63(m,2H),2.33~2.24(m,2H),2.29~2.21(m,2H).

ES-MS m/z: 405.5(M$^+$+1).

A mixture of 67a (350 mg, 0.866 mmol, 1 eq), Et$_3$N (0.18 ml, 1.30 mmol, 1.5 eq), and morpholine (75 mg,0.866 mmol, 1 eq) in EtOH (10 mL) was stirred at 70° C. overnight. The resulting solid was collected by filtration to afford compound 67 (231 mg, purity>95%, yield: 59%) as white solid.

HNMR(CDCl$_3$, 300 MHz):7.94~7.91(m,1H),7.87(s,1H), 7.75~7.71(m,1H),7.62~7.37(m,3H),4.66~4.58(m,1H), 4.23~4.17(m,2H),3.90~3.81(m,8H),3.68~3.53(m,2H), 2.33~2.24(m,2H),2.17~2.11(m,2H). ES-MS m/z: 456(M$^+$+1).

Example 68

9-sec-Butyl-6-(2-difluoromethyl-benzoimidazol-1-yl)-2-morpholin-4-yl-9H-purine

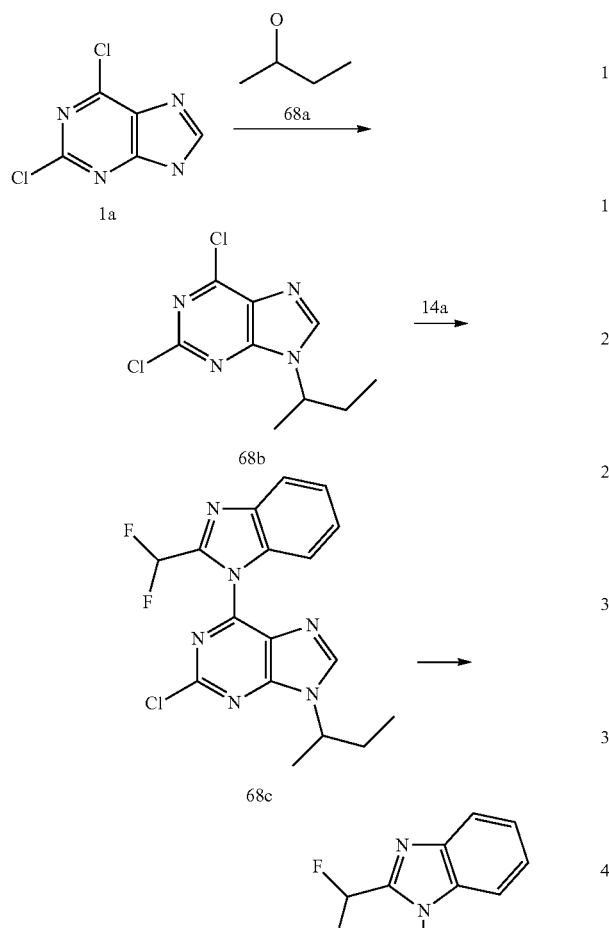

Step 1: DIAD (2.5 g, 13 mmol, 1.2 eq) was added dropwise to a solution of 68a (1 mL, 11 mmol, 1.1 eq), 1 a (2 g, 10 mmol, 1 eq) and PPh$_3$ (3.3 g, 13 mmol, 1.2 eq) in THF (20 mL) under N$_2$ at 0° C. Then the mixture was stirred at r.t. overnight. The solvent was removed and the residue was purified by column chromatography to afford 68b (1.5 g, yield: 57%).

HNMR(CDCl$_3$, 300 MHz):8.12(s,1H), 4.70(m, 1H), 2.06 (m, 2H), 1.63(d, 3H), 0.91(t, 3H).

Step 2: To a solution of 14a (300 mg, 1.8 mmol, 1 eq) in DMF (4 mL) was added NaH (60%, 75 mg, 1.8 mmol, 1 eq) at 0~5° C. The resulting mixture was stirred for 30 min at 0~5° C. and to the mixture was added 68b (459 mg, 1.8 mmol, 1 eq) portion-wise. The reaction mixture was stirred at r.t. over a weekend. The solvent was removed and the residue was purified by column chromatography (PE:EA=4:1) to give 68c (330 mg, yield: 50%) as a colorless oil. ES-MS m/z: 377 (M$^+$+1)

Step 3: A solution of 68c (330 mg, 0.85 mmol) in morpholine (4 mL) was heated to 80° C. for 1 h. After cooling, the solvent was removed and the residue was purified by column chromatography (EA:PE=1:4) to give compound 68 (150 mg, yield: 41%) as a white solid.

HNMR(CDCl3, 300 MHz): 7.93(m, 1H), 7.83(s, 1H), 7.77 (m, 1H), 7.45(m, 3H), 4.58(m, 1H), 3.89(m, 8H), 2.09(m, 2H), 1.65(d, 3H), 0.94(t, 3H).

ES-MS m/z: 428 (M$^+$+1).

Example 69

2-[6-(2-Difluoromethyl-benzoimidazol-1-yl)-2-morpholin-4-yl-purin-9-yl]-propan-1-ol

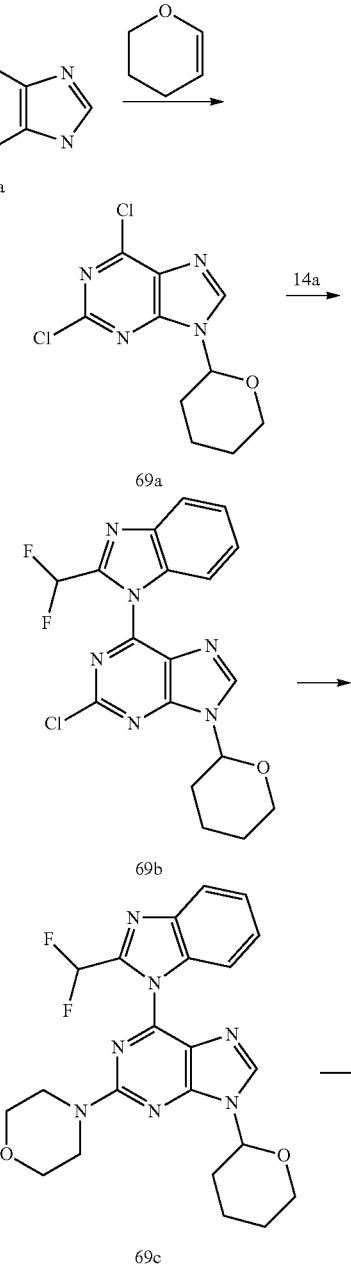

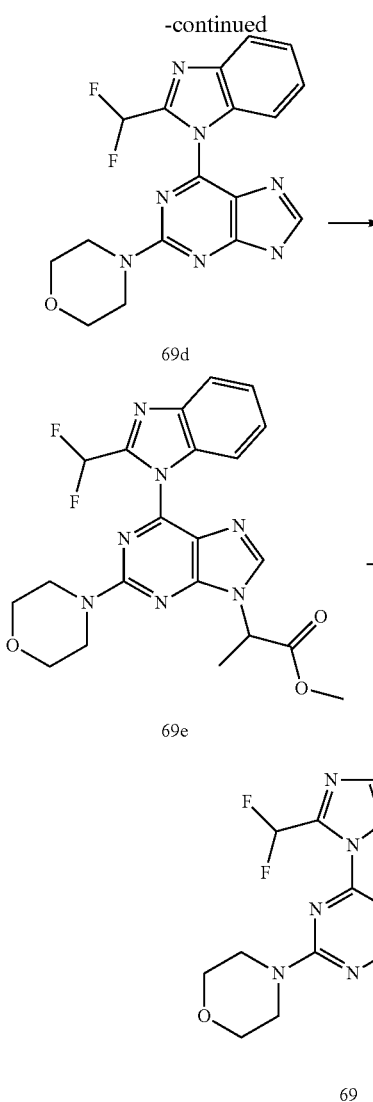

$^1$HNMR(CDCl3, 300 MHz, ppm): δ 8.02(s, 1H), 7.92(m, 1H), 7.72(m, 1H), 7.41(m, 3H), 5.67(m, 1H), 4.18(m, 1H), 3.88(m, 12H), 2.14(m, 4H), 1.80(m, 4H)

ES-MS m/z: 456(M+H$^+$).

Step 4: A mixture of 69c (3.3 g, 7.25 mmol, 1.0 eq) in HCl/EA (40 mL) was stirred at 0° C. for 30 min, and then warmed to room temperature for 1.5 h. The mixture was filtered and the yellow solid was washed with aq. NaHCO$_3$ to give 69d (2.52 g, yield: 93.7%) as a white solid.

H NMR(DMSO-d6, 300 MHz, ppm): δ8.21(s, 1H), 7.87 (m, 1H), 7.75(m, 1H), 7.41(m, 3H), 3.73(m, 12H).

ES-MS m/z: 372(M+H$^+$).

Step 5: A mixture of 69d (2.52 g, 6.79 mmol, 1 eq), K2CO3 (2.8 g, 20.37 mmol, 3 eq), methyl 2-bromopropanoate (1.7 g, 10.19 mmol, 1.5 eq), CuI (778.4 mg, 4.07 mmol, 0.6 eq) in CH$_3$CN (150 mL) was heated to reflux for 4 h. After cooling, the mixture was filtered, the filtrate was concentrated and purified by column chromatography to give 69e (1.8 g, yield: 57.9%) as a yellow solid.

ES-MS m/z: 458(M+H$^+$).

Step 6: To a suspension of LiAlH$_4$ (179.2 mg, 4.72 mmol, 1.2 eq) in THF (45 mL) was added 69e (1.8 g, 3.93 mmol, 1 eq) in THF (5 mL) at 0~5° C. and the mixture was stirred at for 1 h. The solvent was concentrated in vacuo and water was added to the residue in an ice-bath. The mixture was extracted with ethyl acetate, the water phase was filtered and extracted with ether acetate again, the organic layers were combined and dried, concentrated and purified by column chromatography to give compound 69 (1 g, yield: 59.3%) as a light red solid.

$^1$HNMR(CDCl3, 300 MHz, ppm): δ 7.92(m, 2H), 7.75-7.38(m, 4H), 4.72(m, 1H), 4.08(m, 2H), 3.84(m, 8H), 3.28(t, 1H), 1.67(d, 3H).

ES-MS m/z: 430(M+H$^+$).

Example 70

2-[6-(2-Difluoromethyl-benzoimidazol-1-yl)-2-(8-oxa-3-aza-bicyclo[3.2.1]oct-3-yl)-purin-9-yl]-propan-1-ol Step 1: A mixture of 2,6-dichloropurine (3.9 g, 20 mmol, 1 eq), TsOH.H$_2$O (117 mg, 0.61 mmol) and 2H-3,4-dihydropyran (4.6 mL, 50 mmol, 2.5 eq) in ethyl acetate was heated to 50° C. for 2 h. The mixture was concentrated and purified by column chromatography to give 69a (5.0 g, yield: 95%) as a white solid. ES-MS m/z: 273 (M+H$^+$).

Step 2: NaH (60%, 1.1 g, 45.8 mmol, 1.5 eq) was added portion-wise to a solution of compound 14a (3.4 g, 20.1 mmol, 1.1 eq) in DMF (50 mL) at 0° C. and the mixture was stirred at r.t for 45 min. Compound 69a (5.0 g, 18.3 mmol, 1 eq) was added to the mixture. The mixture was stirred at r.t. over a weekend. Water was added and the mixture was extracted with ethyl acetate, the organic layer was washed with water for 3 times, dried, concentrated and purified by column chromatography to give 69b (3.4 g, yield: 45.8%) as a white solid.

$^1$H NMR(CDCl3, 300 MHz, ppm): δ 10.23(s, 1H), 7.72(d, 1H), 7.54(d, 1H)

ES-MS m/z: 321(M+H$^+$).

Step 3: A mixture of 69b (3 g, 7.43 mmol, 1 eq), Et$_3$N (1.54 mL, 1.5 eq) and morpholine (0.78 g, 1.2 eq) in ethanol(150 mL) was heated to 70° C. overnight. The solvent was removed in vacuo and water was added, the resulting precipitate was collected and washed with ethanol to give 69c (3.3 g, yield: 97.6%).

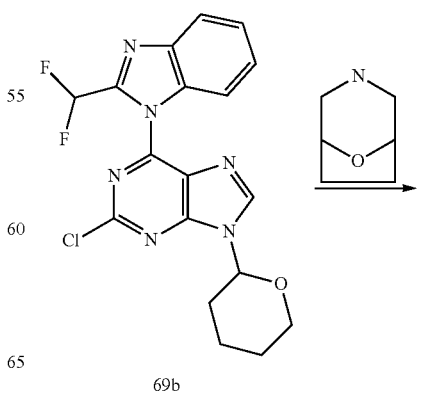

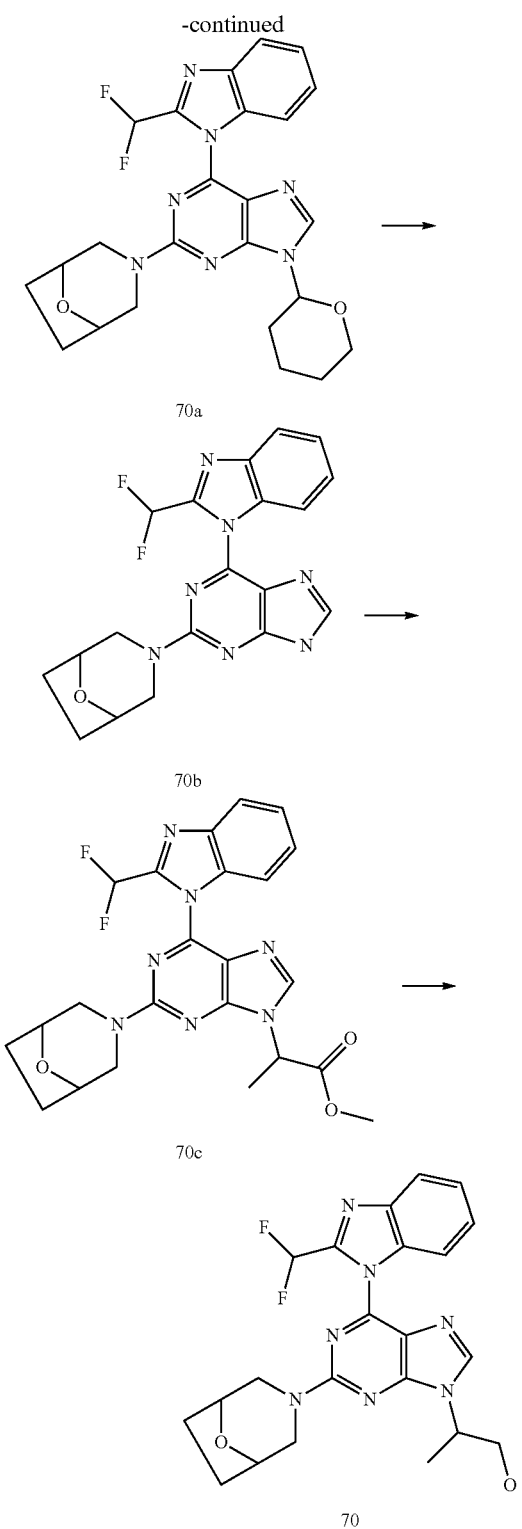

Step 1: A mixture of 69b (202 mg, 0.5 mmol, 1 eq), 8-oxa-3-azabicyclo[3.2.1]octane.HCl (85 mg, 0.57 mmol, 1.14 eq) and $Cs_2CO_3$ (489 mg, 1.5 mmol, 3 eq) in DMF (6 mL) was stirred at 80° C. for 2 hr. The mixture was poured into ice-water, the resulting solid was collected by filtration and washed with water to give compound 70a (170 mg, yield: 70%) as a white solid.

ES-MS m/z: 482(M+H$^+$).

Step 2: A mixture of 70a (80 mg, 0.17 mmol, 1.0 eq) in HCl/EA (3 mL) was stirred at 0° C. for 30 min. The mixture was adjusted pH to 8~9 with aq. $NaHCO_3$ and extracted with EA 3 times. The combined organic layers were dried, filtered and concentrated to give 70b (54 mg, yield: 81.8%).

ES-MS m/z: 398(M+H$^+$)

Step 3: A mixture of 70b (54 mg, 0.13 mmol, 1 eq), $K_2CO_3$ (56.3 mg, 0.39 mmol, 3 eq), methyl 2-bromopropanoate (34.1 mg, 0.20 mmol, 1.5 eq), CuI (15.6 mg, 0.08 mmol, 0.6 eq) in $CH_3CN$ (5 mL) was heated to reflux for overnight. After cooling, the mixture was filtered, the filtrate was concentrated and purified by prep-TLC to give 70c (29 mg, yield: 44.2%).

ES-MS m/z: 484(M+H$^+$)

Step 4: To a suspension of $LiAlH_4$ (5 mg, 0.12 mmol, 2.0 eq) in THF (5 mL) was added 70c (29 mg, 0.06 mmol, 1 eq) in THF (0.5 mL) at 0~5° C. and the mixture was stirred at the same temperature for 1 h. The solvent was concentrated in vacuo and water was added to the residue in an ice-bath. The mixture was extracted with ethyl acetate 3 times, the combined organic layers were dried, concentrated and purified by prep-TLC to give compound 70 (7 mg, yield: 26%).

$^1$HNMR(CDCl3, 300 MHz, ppm): δ 7.91(m, 2H), 7.75~7.38(m, 4H), 4.74(m, 1H), 4.51(m, 2H), 4.22(m, 2H), 4.05(m, 2H), 3.32(m, 2H), 1.97(m, 2H), 1.81(m, 2H), 1.67(d, 3H).

ES-MS m/z: 456(M+H$^+$).

Biochemical Assay (Example)

Assays were performed as described in Fabian et al. (2005) Nature Biotechnology, vol. 23, p. 329 and in Karaman et al. (2008) Nature Biotechnology, vol. 26, p. 127.

Kinase assays. For most assays, kinase-tagged T7 phage strains were grown in parallel in 24-well blocks in an *E. coli* host derived from the BL21 strain. *E. coli* were grown to log-phase and infected with T7 phage from a frozen stock (multiplicity of infection ~0.1) and incubated with shaking at 32° C. until lysis (~90 minutes). The lysates were centrifuged (6,000×g) and filtered (0.2 mm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17× PBS, 0.05% Tween 20, 6 mM DTT). Test compounds were prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with wash buffer (1× PBS, 0.05% Tween 20). The beads were then re-suspended in elution buffer (1× PBS, 0.05% Tween 20, 0.5 mM non-biotinylated affinity ligand) and incubated at room temperature with shaking for 30 minutes. The kinase concentration in the eluates was measured by qPCR.

Compounds were tested using the above assay at Ambit Biosciences (San Diego, Calif., USA). Generally, benzoimidazolyl-containing compounds of Formulae (II) and (III) showed surprisingly potent and selective inhibition against PI3Kδ (IC$_{50}$ less than 30 nM), but less inhibitory activity against other isoforms (>100 nM against PI3Kα, β, γ). Examples 14 and 28 showed surprisingly potent and selective inhibition against PI3Kδ ($IC_{50}$ less than 30 nM), but less inhibitory activity against other isoforms (>100 nM against PI3Kα, β, γ).

Scintillation Proximity Assay (SPA) for p110α, p110β, p110γ, and PI3K C2β

GST-tagged bovine p110α, GST-tagged human p110β, His-tagged p110γ, and Glu-tagged PI3K C2β are expressed in an Sf9/Baculovirus system and purified as fusion proteins. The test compounds are dissolved in DMSO (0.5 μL) and each enzyme is mixed in 25 μL of buffer solution (p110α, β, γ assay: 20 mM Tris-HCl (pH 7.4), 160 mM NaCl, 2 mM dithiothreitol, 30 mM $MgCl_2$, 0.4 mM EDTA, 0.4 mM EGTA; PI3K C2β assay:

20 mM Tris-HCl (pH 7.4), 160 mM NaCl, 2 mM dithiothreitol, 5 mM $MgCl_2$, 15 mM $CaCl_2$, 0.4 mM EDTA). Then, 25 μL of 5 mM Tris-HCl supplemented with 1 μg PI (Sigma), 0.125 μCi [γ-$^{33}$P]ATP (Amersham Pharmacia), and 2 μM non-radiolabeled ATP (Sigma) are added to the mixture to initiate the reaction. After allowing the reaction to proceed at room temperature for 120 min, 0.2 mg of wheat germ agglutinin-coated SPA beads (Amersham) in 150 μL PBS is added. The mixture is left to stand for 5 min and then centrifuged at 300 g for 2 min. Radioactivity is measured using TopCount (Packard).

The Z'-LYTE® biochemical assay for mTor The mTor kinase activity was assessed using the Z'-LYTE® biochemical assay of Invitrogen Corp. (Madison, Wis., USA). Example 28 did not significantly inhibit mTor at up to 1 μM.

Cellular Assay:
Proliferation Assays

Cells (A375, HeLa, A549, MCF7, and MCF7 ADR-res) are cultured in DMEM with 10% fetal bovine serum and streptomycin/penicillin. Solutions of the test compounds (1 μL) are spotted onto a 96-well culture plate, followed by addition of cells ($1 \times 10^4$) in 100 μL. After 46-h incubation, 10 μL of Alamar blue reagent is added to each well. After 2-h, the excitation/emission wavelengths at 544/590 nm are measured using Fluostar.

We claim:
1. The compound of formula IIc:

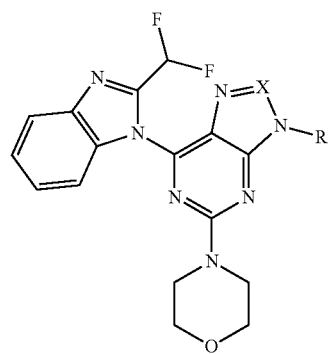

IIc wherein X is N or CR'; R, R' are independently hydrogen, alkyl, cycloalkyl, or heterocyclo, each optionally substituted with $Z_1$, $Z_2$ and $Z_3$;

$Z_1$, $Z_2$ and $Z_3$ are each independently;
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

(ii) a group (i) which is substituted by one or more groups selected from alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl; or (iii) a group (i) or (ii) which is substituted by one or more of the following groups (2) to (13);
(2) —OH or —$OZ_{16}$;
(3) —SH or —$SZ_{16}$;
(4) —$C(O)_2H$, $C(O)_qZ_{16}$, —$C(O)NZ_{17}Z_{18}$, —$C(O)C(O)NZ_{17}Z_{18}$, or —O—$C(O)_q$—$Z_{16}$, where each q is independently 1 or 2;
(5) —$SO_3H$, —$S(O)_qZ_{16}$, or —$S(O)_qNZ_{17}Z_{18}$;
(6) halo;
(7) cyano;
(8) nitro;
(9) —$Z_4$—$NZ_{17}Z_{18}$;
(10) —$Z_4$—$N(Z_{18})$—$Z_5$—$NZ_{19}Z_{20}$;
(11) oxo;
(12) —O—$C(O)$—$Z_{16}$;
(13) any two of $Z_1$, $Z_2$, and $Z_3$ may together be alkylene, alkenylene, aryl, heteroaryl, or heterocyclo completing a 3- to 8-membered saturated or unsaturated ring together with the atoms to which they are attached $Z_4$ and $Z_5$ are each independently
(1) a single bond;
(2) —$Z_{11}$—$S(O)_q$—$Z_{12}$—;
(3) —$Z_{11}$—$C(O)$—$Z_{12}$—;
(4) —$Z_{11}$—O—$Z_{12}$—;
(5) —$Z_{11}$—S—$Z_{12}$—;
(6) —$Z_{11}$—O—$C(O)$—$Z_{12}$—; or
(7) —$Z_{11}$—$C(O)$—O—$Z_{12}$;

$Z_{11}$ and $Z_{12}$ are each independently
(1) a single bond;
(2) alkylene;
(3) alkenylene; or
(4) alkynylene;

each $Z_{16}$ is independently alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl, each optionally substituted with one or more of the following groups:
(1) hydrogen;
(2) —OH or —$OZ_{21}$;
(3) —SH or —$SZ_{21}$;
(4) —$C(O)_2H$, $C(O)_qZ_{21}$, —$C(O)NZ_{17}Z_{18}$, —$C(O)C(O)NZ_{17}Z_{18}$, or —O—$C(O)_qZ_{21}$, where each q is independently 1 or 2;
(5) —$SO_3H$, —$S(O)_qZ_{21}$, or —$S(O)_qNZ_{17}Z_{18}$;
(6) halo;
(7) cyano;
(8) nitro;
(9) —$Z_4$—$NZ_{17}Z_{18}$;
(10) —$Z_4$—$N(Z_{18})$—$Z_5$—$NZ_{19}Z_{20}$;
(11) oxo; or
(12) —O—$C(O)$—$Z_{21}$;

each $Z_{17}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{18}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{19}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{20}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{21}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{22}$ is independently,
(1) hydrogen;
(2) —OH or —$OZ_{21}$;
(3) —SH or —$SZ_{21}$;
(4) —$C(O)_2H$, $C(O)_qZ_{21}$, —$C(O)NZ_{21}Z_{21}$, —$C(O)C(O)NZ_{21}Z_{21}$, or —O—$C(O)_qZ_{21}$, where q is 1 or 2;
(5) —$SO_3H$, —$S(O)_qZ_{21}$, or —$S(O)_qNZ_{21}Z_{21}$;
(6) halo;
(7) cyano;
(8) nitro;
(9) —$Z_4$—$NZ_{21}Z_{21}$;
(10) —$Z_4$—$N(Z_{21})$—$Z_5$—$NZ_{21}Z_{21}$;
(11) oxo; or
(12) —O—C(O)—$Z_{21}$;

where $Z_{17}$, $Z_{18}$, $Z_{19}$ or $Z_{20}$, may be substituted with 1, 2, or 3 independent $Z_{22}$;

where $Z_{17}$ and $Z_{18}$, or $Z_{19}$ and $Z_{20}$, together with the nitrogen atom to which they are attached may be a heterocycle which is unsubstituted or substituted with 1, 2, or 3 independent $Z_{22}$; and where any two of $Z_{18}$, $Z_{19}$ or $Z_{20}$ together with the nitrogen atoms to which they are attached may be a 3- to 12-membered saturated or unsaturated mono-, bi-, or tri- heterocyclic ring which is unsubstituted or substituted with 1, 2, or 3 independent $Z_{22}$.

2. The compound of claim 1, wherein X is CH.

3. The compound of claim 1, wherein the compound is one of

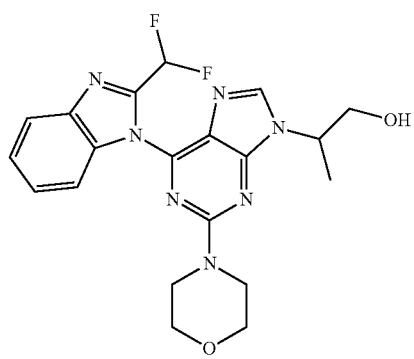

g

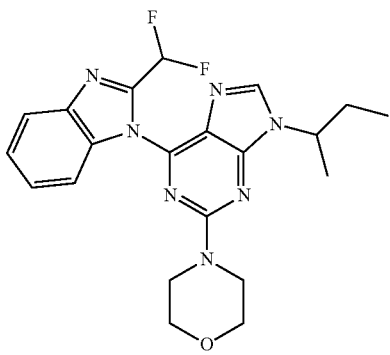

h

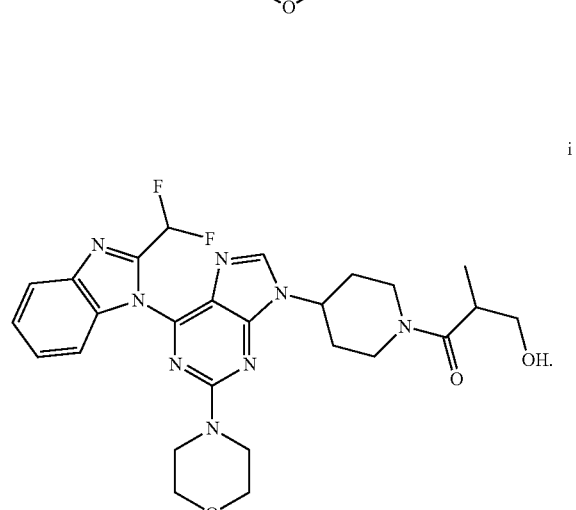

i

4. The compound of claim 1, wherein the compound is one of 6-(2-Difluoromethyl-benzoimidazol-1-yl)-9-[2-(4-methanesulfonyl-piperazin-1-yl)-ethyl]-2-morpholin-4-yl-9H-purine;

2-{6-[2-(difluoromethyl)benzimidazol-1-yl]-2-morpholin-4-ylpurin-9-yl} ethan-1-ol;

6-(2-difluoromethyl-benzoimidazol-1-yl)-2-morpholin-4-yl-9-(tetrahydro-pyran-4-yl)-9H-purine;

9-sec-butyl-6-(2-difluoromethyl-benzoimidazol-1-yl)-2-morpholin-4-yl-9-purine;

2-[6(2-difluorotnethyl-benzoimidazol-1-yl)-2-morpholin-4-yl-purin-9-yl]-propan-1-ol.

* * * * *